(12) United States Patent
Gougoutas et al.

(10) Patent No.: US 9,453,039 B2
(45) Date of Patent: *Sep. 27, 2016

(54) CRYSTAL STRUCTURES OF SGLT2 INHIBITORS AND PROCESSES FOR PREPARING SAME

(71) Applicant: AstraZeneca AB, Sodertalje (SE)

(72) Inventors: Jack Z. Gougoutas, Princeton, NJ (US); Hildegard Lobinger, Princeton, NJ (US); Srividya Ramakrishnan, Princeton, NJ (US); Prashant P. Deshpande, Princeton, NJ (US); Jeffrey T. Bien, Princeton, NJ (US); Chiajen Lai, Princeton, NJ (US); Chenchi Wang, Princeton, NJ (US); Peter Riebel, Princeton, NJ (US); John Anthony Grosso, Princeton, NJ (US); Alexandra A. Nirschl, Princeton, NJ (US); Janak Singh, Princeton, NJ (US); John D. DiMarco, Princeton, NJ (US)

(73) Assignee: AstraZeneca AB, Sodertalje (SE)

( * ) Notice: Subject to any disclaimer, the term of this patent is extended or adjusted under 35 U.S.C. 154(b) by 292 days.

This patent is subject to a terminal disclaimer.

(21) Appl. No.: 13/938,763

(22) Filed: Jul. 10, 2013

(65) Prior Publication Data
US 2013/0303467 A1 Nov. 14, 2013

Related U.S. Application Data

(62) Division of application No. 13/049,712, filed on Mar. 16, 2011, now Pat. No. 8,501,698, which is a division of application No. 11/765,481, filed on Jun. 20, 2007, now Pat. No. 7,919,598.

(60) Provisional application No. 60/817,118, filed on Jun. 28, 2006.

(51) Int. Cl.
*C07H 15/207* (2006.01)
*A61K 31/7034* (2006.01)
*A61K 45/06* (2006.01)
*C07H 7/04* (2006.01)

(52) U.S. Cl.
CPC ......... *C07H 15/207* (2013.01); *A61K 31/7034* (2013.01); *A61K 45/06* (2013.01); *C07H 7/04* (2013.01)

(58) Field of Classification Search
CPC ... C07H 15/207; C07H 7/04; A61K 31/7034
See application file for complete search history.

(56) References Cited

U.S. PATENT DOCUMENTS

| | | | |
|---|---|---|---|
| 6,414,126 B1 | 7/2002 | Ellsworth et al. | |
| 6,515,117 B2 | 2/2003 | Ellsworth et al. | |
| 6,774,112 B2 | 8/2004 | Gougoutas | |
| 2006/0063722 A1 | 3/2006 | Washburn et al. | |

(Continued)

FOREIGN PATENT DOCUMENTS

| | | |
|---|---|---|
| EP | 0997472 | 5/2000 |
| WO | WO 01/27128 | 4/2001 |

(Continued)

OTHER PUBLICATIONS

Mansfield et al., Clin. Pharmacokinet, 2004, 43(5), p. 287-290.*

(Continued)

*Primary Examiner* — Jonathan S Lau
(74) *Attorney, Agent, or Firm* — Terence J. Bogie

(57) ABSTRACT

The present invention relates to physical crystal structures of a compound of the formula I:

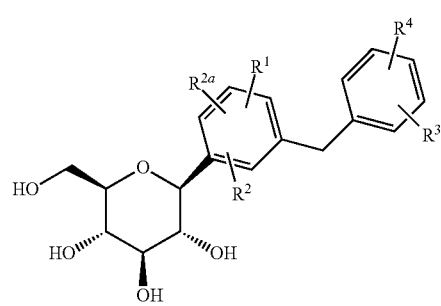

wherein $R^1$, $R^2$, $R^{2a}$, $R^3$ and $R^4$ are as defined herein, especially

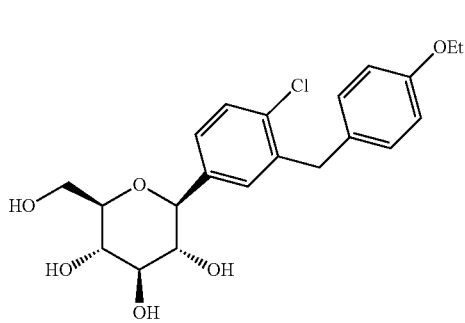

pharmaceutical compositions containing structures of compound I or II, processes for preparing same, intermediates used in preparing same, and methods of treating diseases such as diabetes using such structures.

7 Claims, 22 Drawing Sheets

(56) References Cited

U.S. PATENT DOCUMENTS

2006/0122126 A1    6/2006    Imamura et al.
2007/0015841 A1    1/2007    Tawa et al.

FOREIGN PATENT DOCUMENTS

WO    WO 02/083066    10/2002
WO    WO 2004/063209    7/2004

OTHER PUBLICATIONS

Oswald et al., Crystallography Reviews, 2004, 10(1), p. 57-66.*
Slides from an oral presentation given at Princeton University on Sep. 4, 2008.
Wei Meng et al., Discovery of Dapagliflozin: A Potent, Selective Renal Sodium-Dependent Glucose Cotransporter 2 (SGLT2) Inhibitor for the Treatment of Type 2 Diabetes, J. Med. Chem. 2008, pp. 1145-1149, vol. 51.
Prashant P. Deshpande et al., Remarkable beta-selectivity in the Synthesis of beta-1-C-Arylglucosides: Stereoselective Reduction of Acetyl-Protected Methyl 1-C-Arylglucosides without Acetoxy-Group Participation, J.Org. Chem. 2007, pp. 9746-9749, vol. 72.
International Search Report, European Patent Office, mailed Oct. 31, 2007.
Anthony G. M. Barrett et al., Total Synthesis of the Antifungal Agent Papulacandin D, J. Chem. Soc., Chem. Commun., 1995, pp. 1147-1148.
Anthony G. M. Barrett et al., Total Synthesis and Structural Elucidation of the Antifungal Agent Papulacandin D, J. Org. Chem., 1996, pp. 1082-1100, vol. 61.
Vincente Lecomte et al., Improved Addition of Phenyllithium to Hindered Ketones by the use of Non-polar Media, Tetrahedron Letters, 2002, pp. 3463-3465, vol. 43.
Vincente Lecomte et al., Improved Addition of Organolithium Reagents to Hindered and/or Enolisable Ketones, Tetrahedron, 2003, pp. 2169-2176, vol. 59.
Greene, T.W. et al., "Protective Groups in Organic Synthesis", Third Edition, John Wiley & Sons, Inc. (1999).
Johannson, G. et al, "Growth Hormone Treatment of Abdominally Obese Men Reduces Abdominal Fat Mass Glucose and Lipoprotein Metabolism and Reduces Diastolic Blood Pressure", Journal of Clinical Endocrinology and Metabolism, vol. 82, No. 3, pp. 727-734 (1997).
Kuribayashi, T. et al., "AgOTfa/SnC14: A Powerful New Promoter Combination in the Aryl C-Glycosidation of a Diverse Range of Sugar Acetates and Aromatic Substrates", Tetrahedron Letters vol. 39, pp. 4537-4540, (1998).
Kuribayashi, T. et al, "C-Glycosylated Diphenylmethanes and Benzophenones: The Stille Coupling Reaction of C-Glycosylated Aryl Tins With Benzyl Bromides and Acid Chlorides", J.Carbohydrate Chemistry, 18(4), pp. 393-401, (1999).
Vippagunta et al. Advanced Drug Delivery Reviews, 2001, 48, p. 3-26.
Morris et al. Advanced Drug Delivery Reviews, 2001, 48, p. 91-114.
Seddon et al. Crystal Engineering: the design and application of functional solids, 1999, Kluwer Academic Publishers, p. 69-78.
Definition of solvate, The Free Online Dictionary, http://www.thefreedictionary.com/solvate, accessed online on Jul. 21, 2009.
Brittain, H. G. ed., "Polymorphism in Pharmaceutical Solids," Marcel Dekker, Inc., p. 183-223.
Davidovich, et al., American Pharmaceutical Review, 2004, 7(1), p. 10, 12, 14, 16 and 100.

* cited by examiner

Powder X-ray diffraction patterns of (R)-PG Ib

¹³C NMR CPMAS spectrum for (S)-PG crystalline structure Ia (SC-3 form)

$^{13}$C NMR CPMAS spectrum for (R)-PG 1b

TGA curve of (R)-PG Ib

DSC thermogram of (S)-PG Ia (SC-3 form)

Powder X-ray diffraction pattern of 1,4-butyne-diol solvate If

Powder X-ray diffraction pattern of dimethanol solvate Ig

Melting point of crystals from DSC: 77.5°C
The second endotherm at 250°C is due to decomposition of the compound.

DSC thermogram of 1,4-butyne-diol solvate If

DSC thermogram of dimethanol solvate Ig

PXRD of N-1 1:2 complex Ih

PXRD of N-1 of 1:1 L-proline complex Ii

PXRD pattern of H.5-2 Ij

TGA of N-1 of 1:2 drug:L-proline Ih

TGA of N-1 of 1:1 drug:L-proline Ii

TGA curve of hemihydrate of 1:1 L-proline complex H.5-2 Ij

DSC of N-1 of 1:2 drug:L-proline Ih

DSC thermogram of H.5-2 Ij

CRYSTAL STRUCTURES OF SGLT2 INHIBITORS AND PROCESSES FOR PREPARING SAME

This application is a divisional of U.S. patent application Ser. No. 13/049,712, filed on Mar. 16, 2011, the priority of which under 35 U.S.C. §120 is hereby claimed. U.S. patent application Ser. No. 13/049,712 is a divisional of U.S. patent application Ser. No. 11/765,481, filed on Jun. 20, 2007, the priority of which under 35 U.S.C. §120 is hereby claimed. U.S. patent application Ser. No. 11/765,481 claims priority to U.S. Provisional Patent Application Ser. No. No. 60/817,118, filed on Jun. 28, 2006, the priority of which under 35 U.S.C. §119 is hereby claimed. Each of the above-referenced applications is hereby incorporated herein by reference in its entirety.

FIELD OF THE INVENTION

The present invention relates to free acid polymorphic crystal structures of SGLT2 Inhibitors, pharmaceutical compositions thereof, process for preparing such crystal structures, and methods of treating disorders, such as diabetes, therewith.

BACKGROUND OF THE INVENTION

Approximately 100 million people worldwide suffer from type II diabetes (NIDDM), which is characterized by hyperglycemia due to excessive hepatic glucose production and peripheral insulin resistance, the root causes for which are as yet unknown. Consistent control of plasma glucose levels in diabetes patients may offset the development of diabetic complications and beta cell failure seen in advanced disease.

Plasma glucose is normally filtered in the kidney in the glomerulus and actively reabsorbed in the proximal tubule. Ninety percent of glucose reuptake in the kidney occurs in the epithelial cells of the early S1 segment of the renal cortical proximal tubule. SGLT2, a 672 amino acid protein containing 14 membrane-spanning segments that is predominantly expressed in the early S1 segment of the renal proximal tubules, is likely to be the major transporter responsible for this reuptake. The substrate specificity, sodium dependence, and localization of SGLT2 are consistent with the properties of the high capacity, low affinity, sodium-dependent glucose transporter previously characterized in human cortical kidney proximal tubules. In addition, hybrid depletion studies implicate SGLT2 as the predominant $Na^+$/glucose cotransporter in the S1 segment of the proximal tubule, since virtually all Na-dependent glucose transport activity encoded in mRNA from rat kidney cortex is inhibited by an antisense oligonucleotide specific to rat SGLT2. In humans, mutations in SGLT2 have been associated with familial forms of renal glucosuria, providing further evidence of the primary role of SGLT2 in renal glucose reabsorption. In such patients, renal morphology and renal function is otherwise normal. Inhibition of SGLT2 would be predicted to reduce plasma glucose levels via enhanced glucose excretion in diabetic patients.

Selective inhibition of SGLT2 in diabetic patients could normalize plasma glucose by enhancing the excretion of glucose in the urine, thereby improving insulin sensitivity, and delaying the development of diabetic complications, in the absence of significant gastrointestinal side effects.

SUMMARY OF THE INVENTION

One aspect of the invention relates to crystal structures of a compound of the formula I

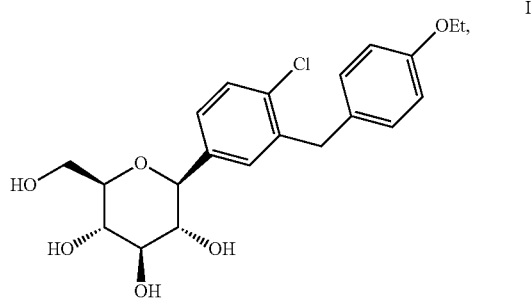

pharmaceutical compositions containing crystal structures of compound I, including the (S)-propylene glycol ((S)-PG) structure Ia which is form SC-3

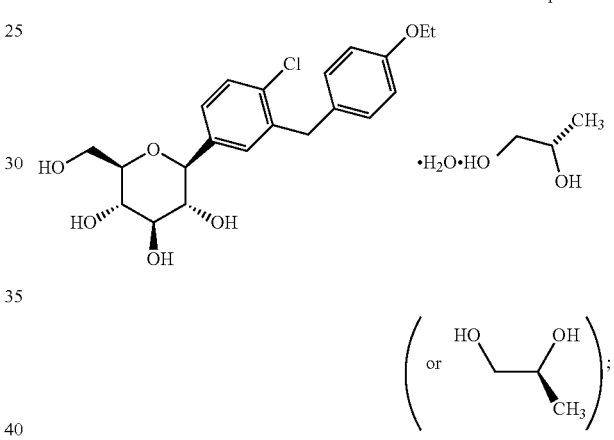

Compound Ia the (R)-propylene glycol ((R)-PG) structure Ib which is form SD-3

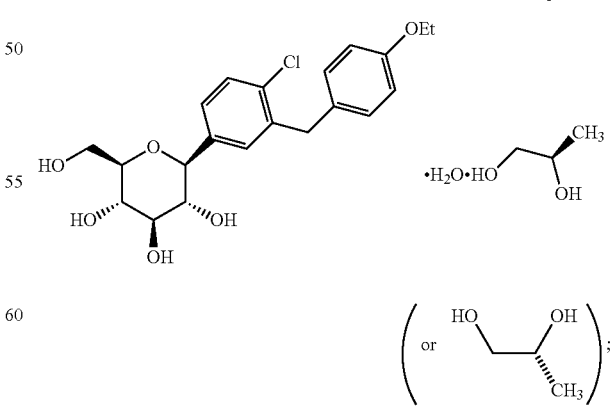

Compound Ib the ethanol or mono-ethanol dihydrate structure Ic which is form SA-1

Compound Ic

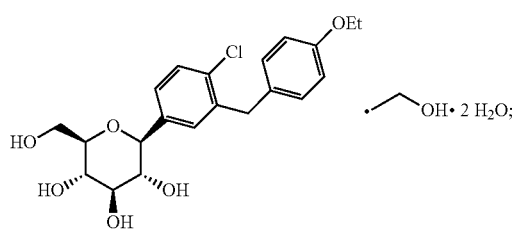

the ethylene glycol structure Id which is form SB-1

Compound Id

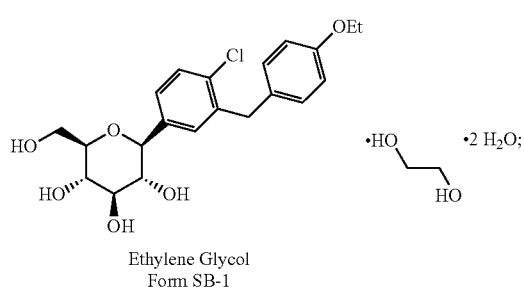

Ethylene Glycol
Form SB-1 and
the ethylene glycol structure Ie which is form SB-2

Compound Ie

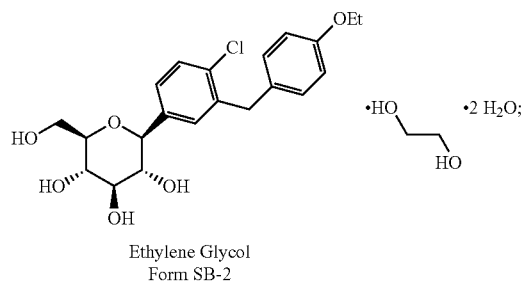

Ethylene Glycol
Form SB-2 processes for preparing such crystal structures;
the 1:2 crystalline complex with L-proline structure Ih which is form 3

Compound Ih

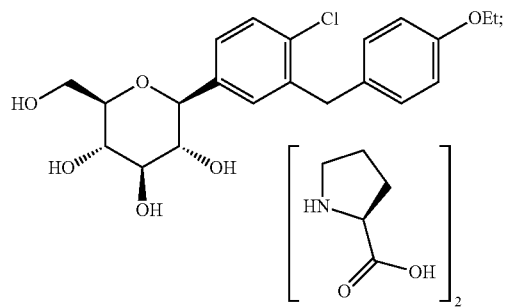

the 1:1 crystalline complex with L-proline structure Ii which is form 6

Compound Ii

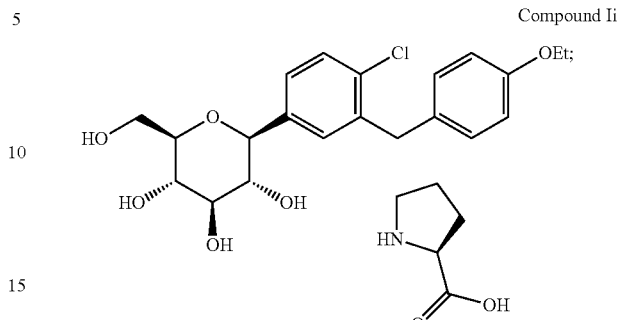

the hemihydrate of the 1:1 crystalline complex with L-proline structure Ij which is form H.5-2

Compound Ij

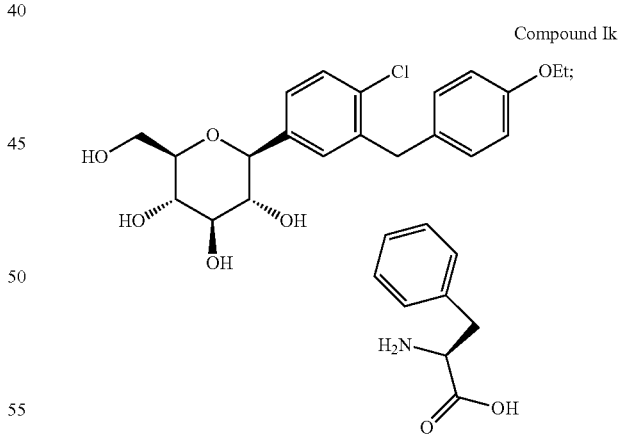

and
the 1:1 crystalline complex with L-phenylalanine structure Ik which is form 2

Compound Ik and methods of treating diabetes and related diseases using the crystal structures of the compound I, compound Ia, compound Ib, compound Ih, compound Ii, compound Ij and compound Ik, and compound II as defined herein.

The compound of formula I in the form of a non-crystalline solid is disclosed in U.S. Pat. No. 6,515,117, the disclosure of which in its entirety is incorporated herein by reference.

In addition, in another aspect of the invention, a crystalline of compound If which has the structure

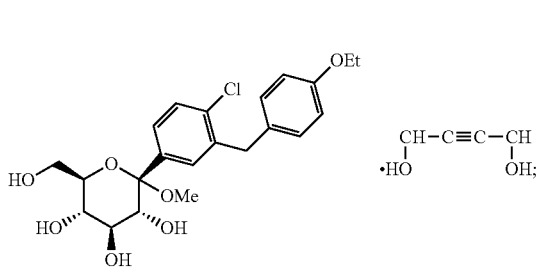

If

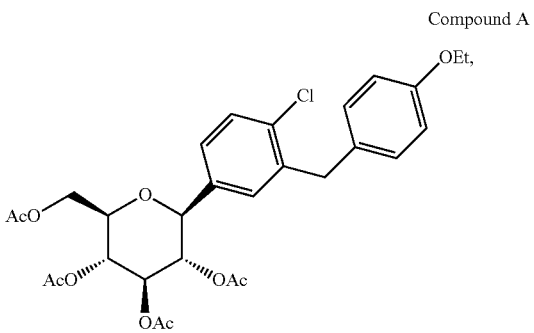 [SMILES: CCOc1ccc(Cc2cc([C@@H]3O[C@H](COC(C)=O)[C@@H](OC(C)=O)[C@H](OC(C)=O)[C@H]3OC(C)=O)ccc2Cl)cc1]

Compound A (also referred to as the "1,4-butyne-diol solvate" or "butynediol solvate"); and a process for preparing such crystal structure and using such crystal structure to prepare crystalline compound Ia (S)-PG are also provided.

In still another aspect of the present invention, a crystalline compound Ig which has the structure treating compound A with an alcohol solvent such as methanol or ethanol, and aqueous base such as sodium hydroxide, and water, if necessary, under an inert atmosphere, and elevated temperature, if necessary, adding an acid such as hydrochloric acid to neutralize the reaction mixture, to form compound I of the structure Ig

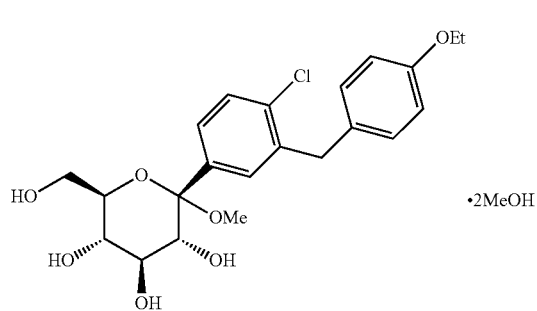

Compound I

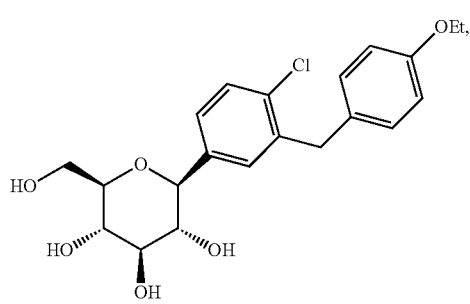

I also referred to as the "dimethanol solvate", and a process for preparing the dimethanol solvate Ig and using Ig to prepare crystalline compound Ia (S)-PG are also provided.

The dimethanol solvate Ig and the 1,4-butyne-diol solvate If may be used as intermediates in the preparation of crystalline compound of formula I of the invention.

In yet another aspect of the present invention, a process for the preparation of the crystalline compound (S)-PG of the structure Ia (SC-3 form) is provided and treating the reaction mixture containing compound I with an organic solvent such as methyl t-butyl ether, an alkyl acetate such as ethyl acetate, methyl acetate, isopropyl acetate, or butyl acetate, and (S)-propylene glycol, optionally adding seeds of (S)-PG compound Ia (SC-3) to the mixture, to form (S)-PG compound Ia (SC-3 form).

In still another aspect of the present invention, a process for preparing the crystalline compound (R)-PG of the structure Ib (SD-3 form)

Ib

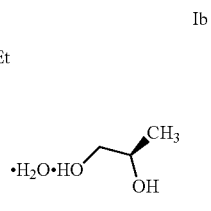

(R)-propylene glycol

Compound Ia

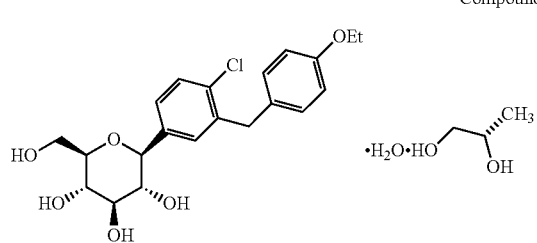

which includes the steps of providing a compound A (prepared as described in U.S. application Ser. No. 10/745,075 filed Dec. 23, 2003, Examples 17 to 20), of the structure is provided which is similar to the process for preparing (S)-PG (SC-3 form) Ia described above except that (R)-propylene glycol is employed in place of (S)-propylene glycol.

In still another aspect of the invention, a novel process is provided for preparing compound Ia

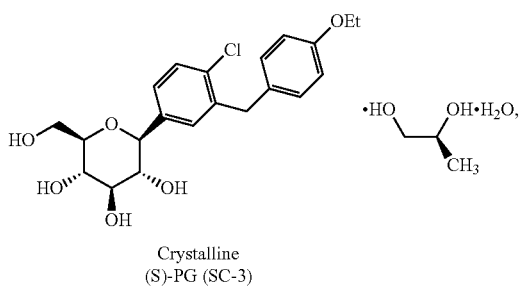

Crystalline
(S)-PG (SC-3)

which includes the step of reducing a compound B of the structure

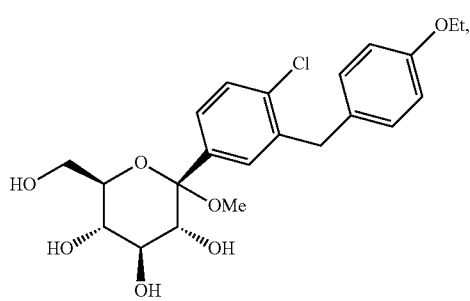

to remove the methoxy group by treating compound B (prepared as described in U.S. application Ser. No. 10/745,075 filed Dec. 23, 2003, Example 17), or a crystalline solvate such as the dimethanol solvate Ig or the 1,4-butynediol solvate (If), with a reducing agent, such as triethylsilyl hydride and an activating group which is a Lewis acid such as $BF_3 \cdot Et_2O$ or $BF_3 \cdot 2CH_3COOH$, preferably $BF_3 \cdot 2CH_3COOH$, and an organic solvent such as $CH_3CN$, and added water, separating out the compound of the structure I

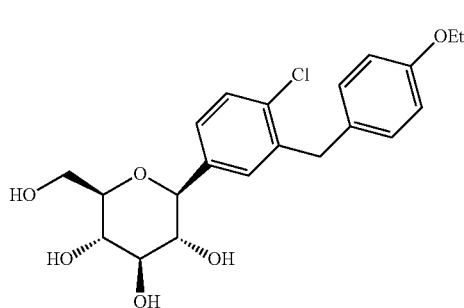

and treating compound I with (S)-propylene glycol in the presence of a solvent such as t-butylmethyl ether, optionally with seeds of compound Ia ((S)-PG), to form a crystal slurry of compound Ia ((S)-PG) and separating out compound Ia ((S)-PG).

The above process of the invention is a one-pot operation which minimizes the production of intermediates, resulting in improved yield and priority of the final crystalline compound Ia.

The crystalline compound Ia which is also referred to as the (S)-propylene glycol solvate of compound I is a novel crystalline structure and is part of the present invention.

The compound of formula B (amorphous form) is disclosed in U.S. application Ser. No. 10/745,075 filed Dec. 23, 2003, the disclosure of which in its entirety is incorporated herein by reference.

In another aspect of the present invention, a process is provided for preparing the mono-EtOH-dihydrate (ethanol or EtOH structure) form SA-1 having the structure Ic

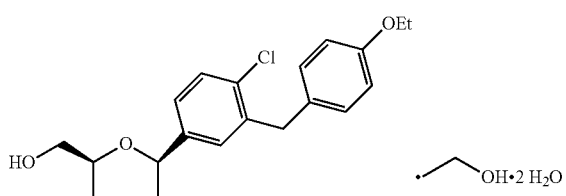

which includes the steps of dissolving compound I in ethanol and cooling the solution to −20° C. to form crystals of formula Ic form SA-1.

Compound I may be prepared by dissolving compound A in ethanol by preferably heating to a boil to form an oily product which is compound I.

In yet another embodiment of the invention, a process is provided for forming the ethylene glycol dihydrate structure of formula Id

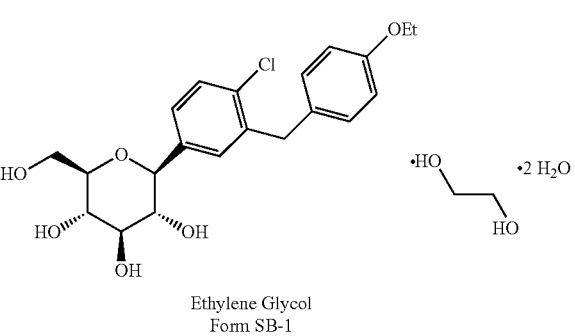

Ethylene Glycol
Form SB-1 which includes the steps of dissolving compound I in aqueous ethylene glycol preferably with heating, optionally, upon cooling, adding seeds of the (S)-propylene glycol crystal form SC-3 (Ia) to the above solution, and recovering crystals of ethylene glycol dihydrate form SB-1 (Id).

In an additional embodiment of the invention, a process is provided for forming the ethylene glycol dihydrate structure form SB-2

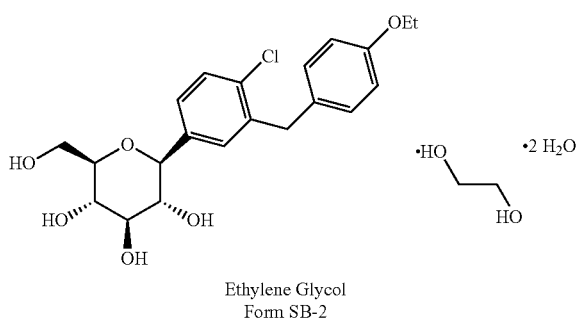

Ethylene Glycol
Form SB-2 which includes the steps of:

dissolving compound I in aqueous ethylene glycol, preferably with heating;

optionally, upon cooling, adding seeds of the mono-EtOH-dihydrate crystal form SA-1 (Ic) to the above solution; and recovering crystals of ethylene glycol dihydrate form SB-2 (Ie).

In yet another embodiment of the present invention, a process is provided for preparing the crystalline 1,4-butyne-diol solvate If

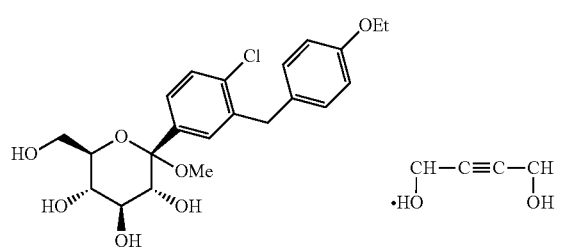

which includes the steps of dissolving the base compound B

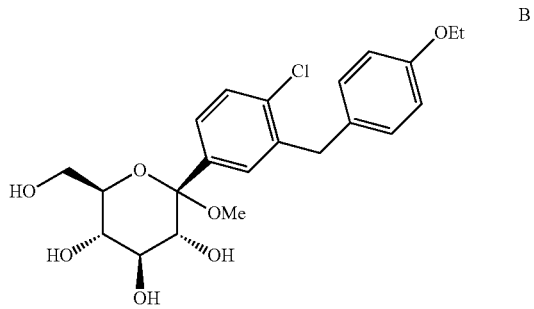 [SMILES: CCOc1ccc(Cc2cc([C@]3(OC)O[C@H](CO)[C@@H](O)[C@H](O)[C@H]3O)ccc2Cl)cc1]

in an alkyl acetate such as ethyl acetate, propyl acetate or butyl acetate or an alcohol such as isopropanol or butanol, or water, adding 2-butyne-1,4-diol to the solution of compound B, heating the resulting mixture until the diol dissolves, cooling the mixture, and recovering crystals of 1,4-butyne-diol solvate If. Toluene or heptane may be employed as an antisolvent when the solvate If is crystallized in an alkyl acetate.

The 1,4-butyne-diol solvate If can be isolated and used to prepare compound I or compound Ia in a continuous process or batch process as described hereinafter.

In addition, in another aspect of the present invention, a process for preparing the crystalline dimethanol solvate Ig is provided

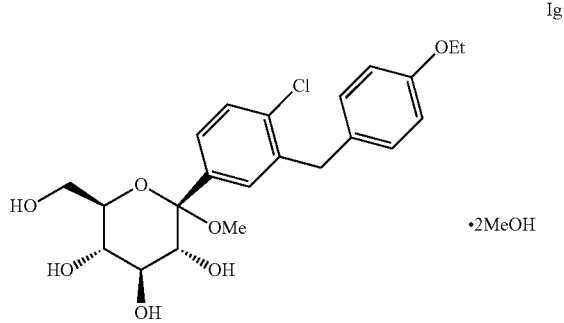 [SMILES: CCOc1ccc(Cc2cc([C@]3(OC)O[C@H](CO)[C@@H](O)[C@H](O)[C@H]3O)ccc2Cl)cc1]

wherein the base compound B

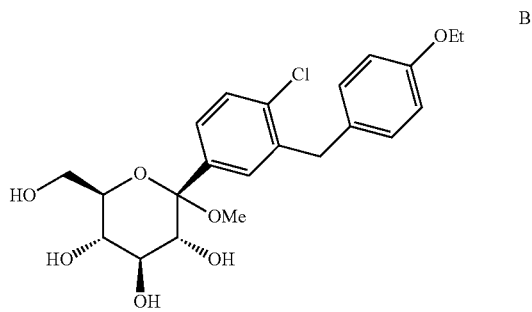 [SMILES: CCOc1ccc(Cc2cc([C@]3(OC)O[C@H](CO)[C@@H](O)[C@H](O)[C@H]3O)ccc2Cl)cc1]

is treated with methanol to form the crystalline dimethanol solvate Ig.

Still further in accordance with the invention, a process is provided for preparing the crystalline dimethanol solvate Ig wherein the base compound B is dissolved in a mixture of methanol/toluene or in a mixture of methanol/toluene/heptane, or in a mixture of methanol/toluene/ethyl acetate or other alkyl acetate, with seeding with seeds of dimethanol solvate Ig.

The dimethanol solvate Ig and the 1,4-butyne-diol solvate If may be used to prepare crystalline compound Ia as described herein.

In yet another aspect of the present invention, a process for the preparation of the crystalline 1:2 complex with L-proline of the structure Ih (form 3) is provided

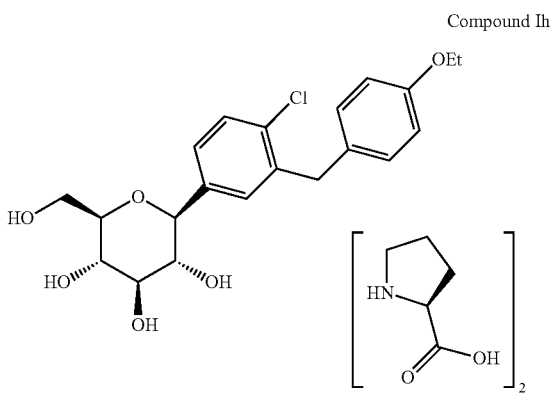

which includes the steps of providing compound I of the structure

Compound I

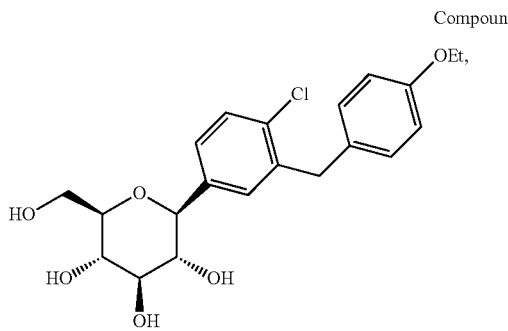

forming a solution of L-proline in water and an alcohol solvent such as methanol, ethanol or isopropanol heated to a temperature within the range from about 70 to about 95° C., treating compound I in an alcohol solvent such as methanol, ethanol, or isopropanol, with the heated solution of L-proline (containing two times the number of moles of L-proline as compound I), and cooling the resulting solution to about room temperature to form compound Ih.

In still another aspect of the present invention, a process for preparing the crystalline compound 1:1 complex with L proline of the structure Ii (form 6) is provided Compound Ii

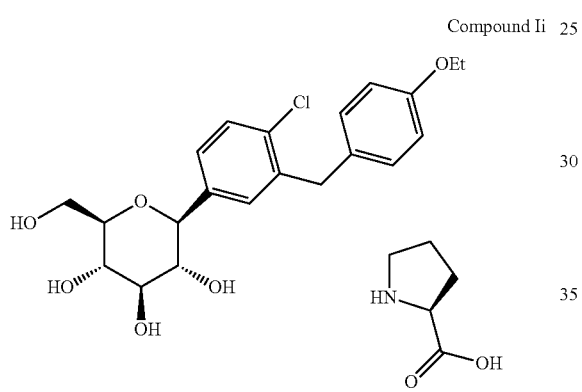

which includes the steps of providing compound I, treating a solution of compound I in an alcohol solvent such as ethanol or methanol with a boiling solution of L-proline in an alcohol/water solvent such as ethanol/water (employing about five times as much compound I as L-proline), and cooling the resulting mixture (for example to from about −10 to about −25° C.) to form compound Ii.

In still another aspect of the present invention, a process for the preparation of the crystalline hemihydrate of the 1:1 complex with L-proline of the structure Ij (form H.5-2) which has the structure Compound Ij

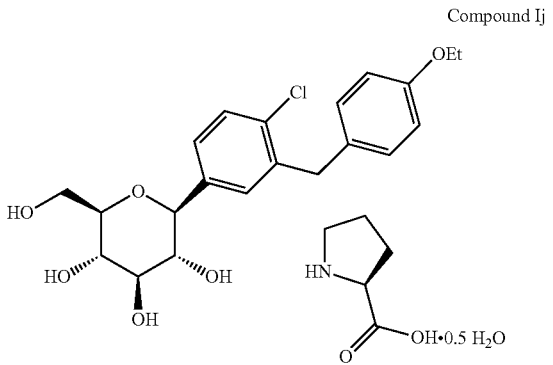

is provided which includes the steps of providing seed crystals of the 1:1 complex with L-proline (structure Ii, form 6), mixing the seed crystals Ii, form 6 with a cooled solution of (−10 to −25° C.) of L-proline and compound I in an alcohol/water solvent, and cooling the resulting mixture at a temperature from about −10 to −25° C. to form the hemihydrate structure Ij (form H.5-2).

In yet another aspect of the present invention, a process for preparing the 1:1 crystalline complex with L-phenylalanine structure Ik form 2

Compound Ik

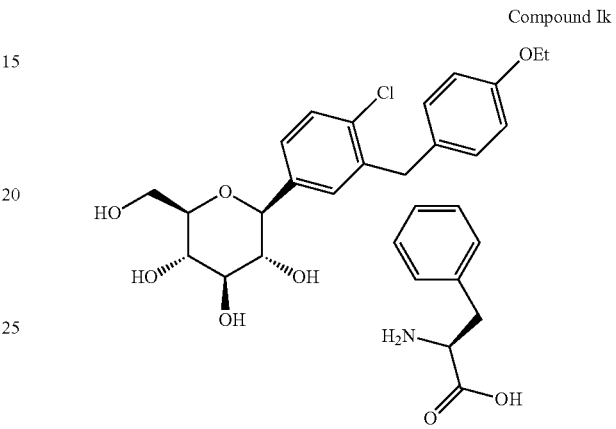

is provided, which includes the steps of forming a solution of L-phenylalanine in water heated at from about 75 to about 85° C., mixing the L-phenylalanine solution with compound I, heating the resulting solution to from about 75 to about 85° C., and allowing the resulting solution to cool to room temperature to form compound Ik.

Another aspect of the invention relates to crystal structures of a compound of the formula II

II

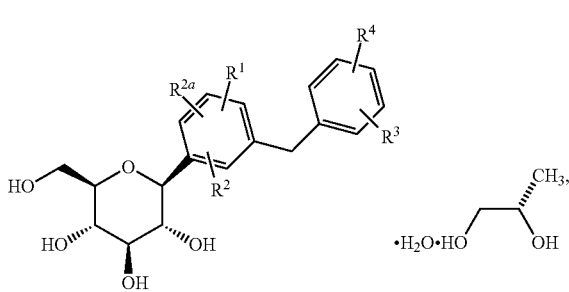

which is also referred to as the (S)-propylene glycol ((S)-PG) crystalline structure II, wherein:

$R^1$, $R^2$ and $R^{2a}$ are independently hydrogen, OH, $OR^5$, alkyl, —$OCHF_2$, —$OCF_3$, —$SR^{5a}$ or halogen;

$R^3$ and $R^4$ are independently hydrogen, OH, $OR^{5b}$, alkyl, alkenyl, alkynyl, cycloalkyl, $CF_3$, —$OCHF_2$, —$OCF_3$, halogen, —$CONR^6R^{6a}$, —$CO_2R^{5c}$, —$CO_2H$, —$COR^{6b}$, —CH(OH)$R^{6c}$, —CH($OR^{5d}$)$R^{6d}$, —CN, —$NHCOR^{5e}$, —$NHSO_2R^{5f}$, —$NHSO_2$Aryl, —$SR^{5g}$, —$SOR^{5h}$, —$SO_2R^{5i}$, —$SO_2$Aryl, or a five, six or seven membered heterocycle which may contain 1 or 4 heteroatoms in the ring which are N, O, S, SO, and/or $SO_2$, or $R^3$ and $R^4$ together with the carbons to which they are attached form an annelated five, six or seven membered carbocycle or heterocycle which may contain 1 to 4 heteroatoms in the ring which are N, O, S, SO, and/or SO$_2$;

R$^5$, R$^{5a}$, R$^{5b}$, R$^{5c}$, R$^{5d}$, R$^{5e}$, R$^{5f}$, R$^{5g}$, R$^{5h}$ and R$^{5i}$ are independently alkyl; and R$^6$, R$^{6a}$, R$^{6b}$, R$^{6c}$ and R$^{5d}$ are independently hydrogen, alkyl, aryl, alkylaryl or cycloalkyl, or R$^6$ and R$^{6a}$ together with the nitrogen to which they are attached form an annelated five, six or seven membered heterocycle which may contain 1 to 4 heteroatoms in the ring which are N, O, S, SO, and/or SO$_2$.

In addition, in accordance with the invention, pharmaceutical compositions containing a crystal structure of compound II and processes for preparing such crystal structure II are also provided.

Still another aspect of the invention relates to crystal structures of a compound of the formula III

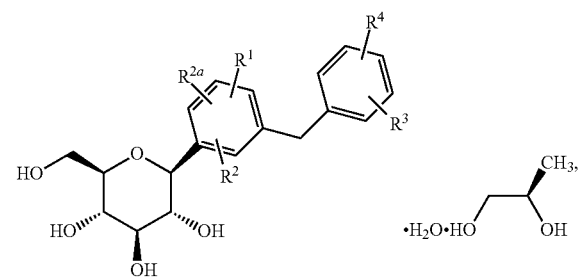

which is also referred to as the (R)-propylene glycol ((R)-PG) crystalline structure III, wherein R$^1$, R$^2$ and R$^{2a}$ are independently hydrogen, OH, OR$^5$, alkyl, —OCHF$_2$, —OCF$_3$, —SR$^{5a}$ or halogen;

R$^3$ and R$^4$ are independently hydrogen, OH, OR$^{5b}$, alkyl, alkenyl, alkynyl, cycloalkyl, CF$_3$, —OCHF$_2$, —OCF$_3$, halogen, —CONR$^6$R$^{6a}$, —CO$_2$R$^{5c}$, —CO$_2$H, —COR$^{6b}$, —CH(OH)R$^{6c}$, —CH(OR$^{5d}$)R$^{6d}$, —CN, —NHCOR$^{5e}$, —NHSO$_2$R$^{5f}$, —NHSO$_2$Aryl, —SR$^{5g}$, —SOR$^{5h}$, —SO$_2$R$^{5i}$, —SO$_2$Aryl, or a five, six or seven membered heterocycle which may contain 1 to 4 heteroatoms in the ring which are N, O, S, SO, and/or SO$_2$, or R$^3$ and R$^4$ together with the carbons to which they are attached form an annelated five, six or seven membered carbocycle or heterocycle which may contain 1 to 4 heteroatoms in the ring which are N, O, S, SO, and/or SO$_2$;

R$^5$, R$^{5a}$, R$^{5b}$, R$^{5c}$, R$^{5d}$, R$^{5e}$, R$^{5f}$, R$^{5g}$, R$^{5h}$ and R$^{5i}$ are independently alkyl; and R$^6$, R$^{6a}$, R$^{6b}$, R$^{6c}$ and R$^{5d}$ are independently hydrogen, alkyl, aryl, alkylaryl or cycloalkyl, or R$^6$ and R$^{6a}$ together with the nitrogen to which they are attached form an annelated five, six or seven membered heterocycle which may contain 1 to 4 heteroatoms in the ring which are N, O, S, SO, and/or SO$_2$.

In addition, in accordance with the invention, pharmaceutical compositions containing crystal structure of compound III and to processes for preparing such crystal structure III are also provided.

In yet another aspect of the present invention, a process for the preparation of the crystalline compound (S)-PG of the structure II is provided which includes the steps of providing a compound C (including where R$^3$ or R$^4$ is alkenyl or alkynyl, all of which may be prepared using procedures as described in U.S. application Ser. No. 10/745,075 filed Dec. 23, 2003, Examples 17 to 20), of the structure

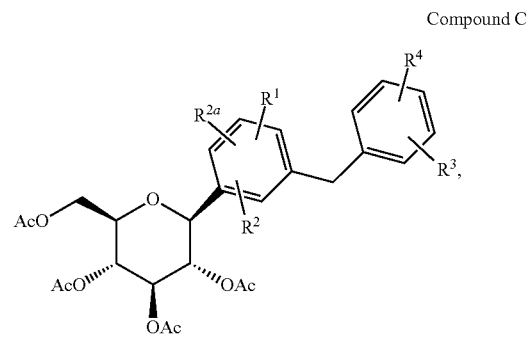

wherein R$^1$, R$^2$, R$^{2a}$, R$^3$ and R$^4$ are as described above;

treating compound C with an alcohol solvent such as methanol, and aqueous base such as sodium hydroxide, and water, if necessary, under an inert atmosphere, and elevated temperature to form compound D of the structure

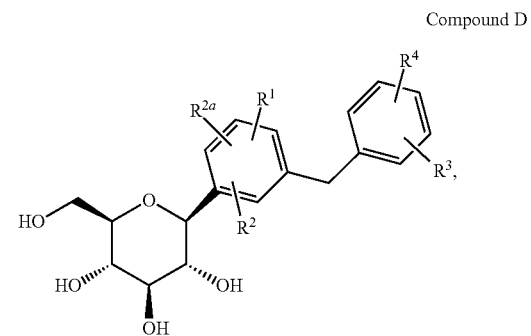

and treating the reaction mixture containing compound D with an organic solvent such as methyl t-butyl ether, an alkyl acetate such as ethyl acetate, methyl acetate, isopropyl acetate, or butyl acetate, and (S)-propylene glycol, optionally adding seeds of (S)-PG compound II to the mixture, to form (S)-PG compound II.

In still another aspect of the present invention, a process for preparing the crystalline compound (R)-PG of the structure III

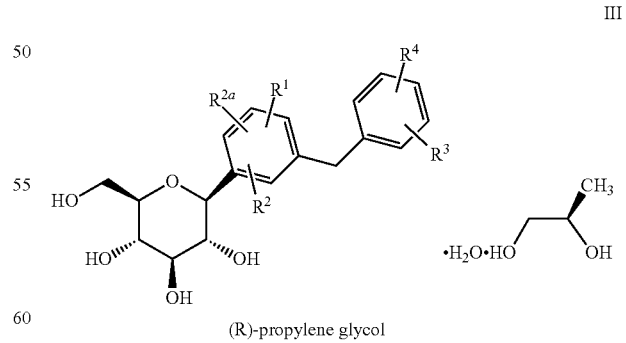

is provided which is similar to the process for preparing (S)-PG II described above except that (R)-propylene glycol is employed in place of (S)-propylene glycol.

In still another aspect of the invention, a novel process is provided for preparing compound II

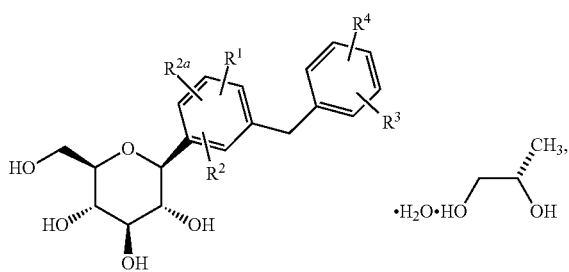

which includes the step of reducing a compound E of the structure

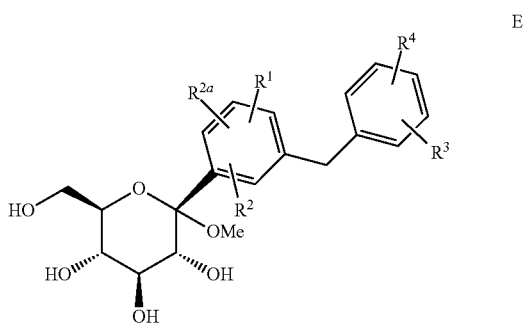

(which is disclosed in U.S. application Ser. No. 10/745,075 filed Dec. 23, 2003) to remove the methoxy group by treating compound E with a reducing agent, such as triethylsilyl hydride and an activating group which is a Lewis acid such as $BF_3 \cdot Et_2O$, and an organic solvent such as $CH_3CN$, and water, separating out the compound of the structure D and treating compound D with (S)-propylene glycol in the presence of a solvent such as t-butylmethyl ether, optionally with seeds of compound II ((S)-PG), to form a crystal slurry of compound II ((S)-PG) and separating out compound II ((S)-PG).

The above process of the invention is a one-pot operation which minimizes the production of intermediates.

BRIEF DESCRIPTION OF THE FIGURES

The invention is illustrated by reference to the accompanying drawings described below.

DETAILED DESCRIPTION OF THE INVENTION

Figure 1:
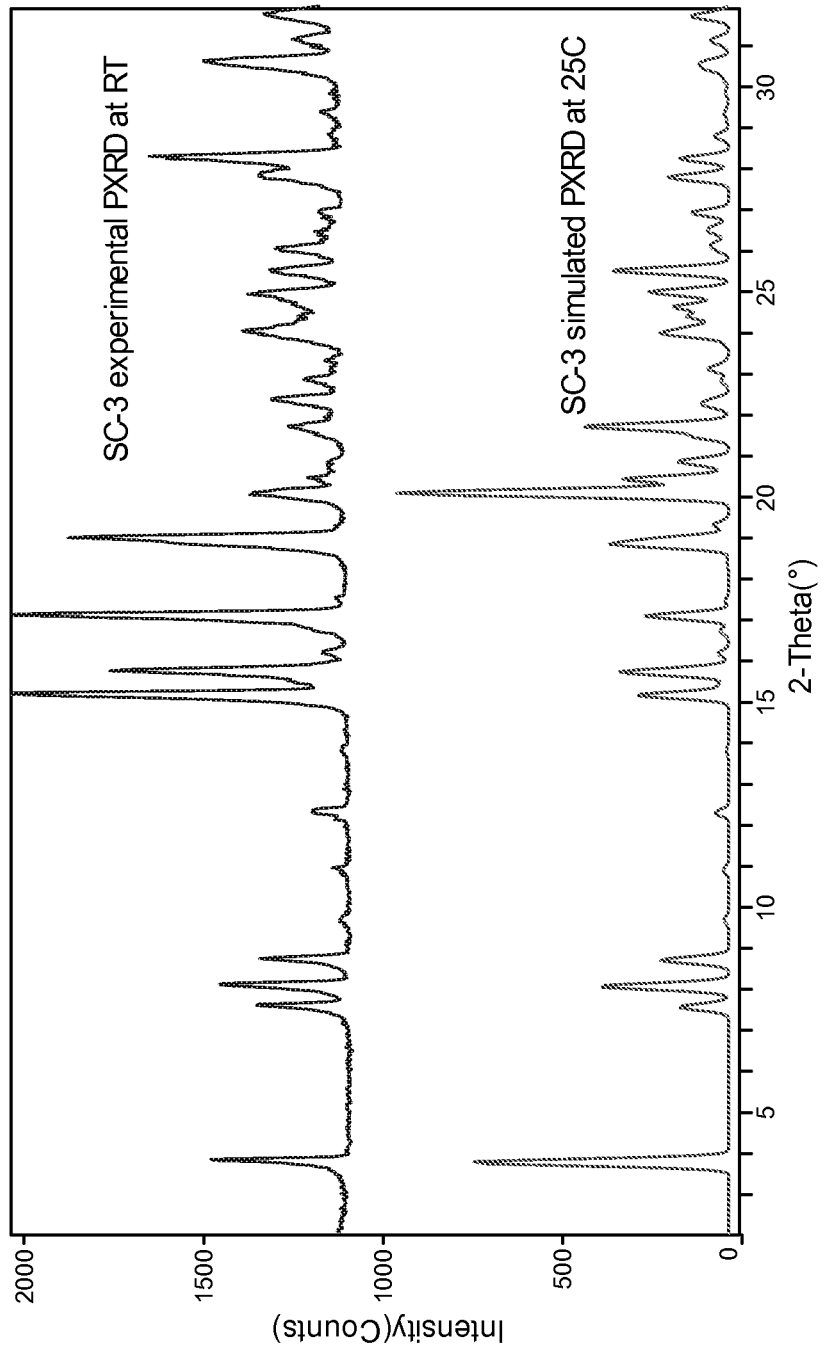
FIG. 1 shows calculated (simulated at 25° C.) and observed (experimental at room temperature) powder X-ray diffraction patterns of the (S)-PG crystalline structure Ia, SC-3 form.

The present invention provides, at least in part, crystalline structures of compound I as a novel material.

The term "pharmaceutically acceptable", as used herein, refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. In certain preferred embodiments, the crystalline structures of compound I of the invention is in substantially pure form. The term "substantially pure", as used herein, means a compound having a purity greater than about 90% including, for example, about 91%, about 92%, about 93%, about 94%, about 95%, about 96%, about 97%, about 98%, about 99%, and about 100%.

The ability of a compound to exist in different crystal structures is known as polymorphism. As used herein "polymorph" refers to crystalline forms having the same chemical composition but different spatial arrangements of the molecules, atoms, and/or ions forming the crystal. While polymorphs have the same chemical composition, they differ in packing and geometrical arrangement, and may exhibit different physical properties such as melting point, shape, color, density, hardness, deformability, stability, dissolution, and the like. Depending on their temperature-stability relationship, two polymorphs may be either monotropic or enantiotropic. For a monotropic system, the relative stability between the two solid phases remains unchanged as the temperature is changed. In contrast, in an enantiotropic system there exists a transition temperature at which the stability of the two phases reverse. (Theory and Origin of Polymorphism in "Polymorphism in Pharmaceutical Solids" (1999) ISBN:)-8247-0237).

Samples of the crystalline structures of the invention may be provided with substantially pure phase homogeneity, indicating the presence of a dominant amount of a single crystalline structure and optionally minor amounts of one or more other crystalline structures. The presence of more than one crystalline structure of the invention in a sample may be determined by techniques such as powder X-ray diffraction (PXRD) or solid state nuclear magnetic resonance spectroscopy (SSNMR). For example, the presence of extra peaks in the comparison of an experimentally measured PXRD pattern (observed) with a simulated PXRD pattern (calculated) may indicate more than one crystalline structure in the sample. The simulated PXRD may be calculated from single crystal X-ray data. (see Smith, D. K., "A FORTRAN Program for Calculating X-Ray Powder Diffraction Patterns," Lawrence Radiation Laboratory, Livermore, Calif., UCRL-7196, April 1963; see also Yin. S., Scaringe, R. P., DiMarco, J., Galella, M. and Gougoutas, J. Z., American Pharmaceutical Review, 2003, 6, 2, 80). Preferably, the crystalline structure has substantially pure phase homogeneity as indicated by less than 10%, preferably less than 5%, and more preferably less than 2% of the total peak area in the experimentally measured PXRD pattern arising from the extra peaks that are absent from the simulated PXRD pattern. Most preferred is a crystalline structure of the invention having substantially pure phase homogeneity with less than 1% of the total peak area in the experimentally measured PXRD pattern arising from the extra peaks that are absent from the simulated PXRD pattern.

The various crystalline structures of the invention described herein may be distinguishable from one another through the use of various analytical techniques known to one of ordinary skill in the art. Such techniques include, but are not limited to, solid state nuclear magnetic resonance (SSNMR) spectroscopy, X-ray powder diffraction (PXRD), differential scanning calorimetry (DSC), and/or thermogravimetric analysis (TGA).

Preparation of Crystal Structures

The crystalline structures of the invention may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline structures from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (counter solvents) to the solvent mixture. High throughput crystallization techniques may be employed to prepare crystalline structures, including polymorphs.

Crystals of drugs, including polymorphs, methods of preparation, and characterization of drug crystals are discussed in Solid-State Chemistry of Drugs, S. R. Byrn, R. R. Pfeiffer, and J. G. Stowell, $2^{nd}$ Edition, SSCI, West Lafayette, Ind., 1999.

Seed crystals may be added to any crystallization mixture to promote crystallization. As will be clear to the skilled artisan, seeding is used as a means of controlling growth of a particular crystalline structure or as a means of controlling the particle size distribution of the crystalline product. Accordingly, calculation of the amount of seeds needed depends on the size of the seed available and the desired size of an average product particle as described, for example, in "Programmed cooling of batch crystallizers," J. W. Mullin and J. Nyvlt, Chemical Engineering Science, 1971, 26, 369-377. In general, seeds of small size are needed to effectively control the growth of crystals in the batch. Seeds of small size may be generated by sieving, milling, or micronizing of larger crystals, or by micro-crystallization of solutions. Care should be taken that milling or micronizing of crystals does not result in any change in crystallinity from the desired crystal structure (i.e. change to amorphous or to another polymorph).

As used herein, the term "room temperature" or "RT" denotes an ambient temperature from 20 to 25° C. (68-77° F.).

In general, in preparing crystalline compound Ia as described below, solvent(s) will be employed to enable formation of the crystalline compound Ia, preferably having a bulk density as described below.

The crystalline compound of the structure Ia (S-PG) SC-3 of the invention prepared according to the following telescoped reaction as shown in Scheme I.

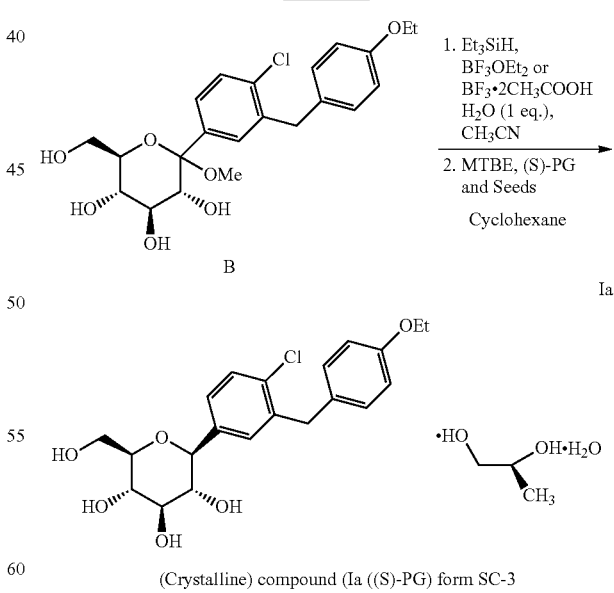

As seen in Scheme I, compound B or If or Ig (collectively referred to as compound B) wherein compound B in the form of an amorphous solid or crystalline solid (If or Ig) is treated with a reducing agent such as a silyl hydride, preferably an alkylsilyl hydride, more preferably triethylsilane (or triethylsilyl hydride), in the presence of an activating group which is a Lewis acid, such as BCl₃.Me₂S, BBr₃, BF₃OEt₂, BCl₃, or BF₃.2CH₃COOH, preferably BF₃OEt₂ or BF₃.2CH₃COOH and an organic solvent such as CH₃CN, CH₃CN/toluene or CH₃CN/dichloromethane, methylene chloride or water, at a temperature within the range from about −15 to about 25° C., preferably from about 5 to about 10° C., to reduce compound B and form the corresponding base compound I

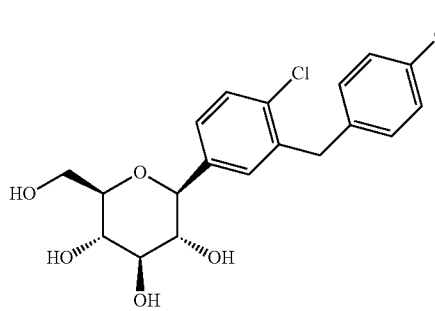

which is separated from the reaction mixture and treated with (S)-propylene glycol ((S)-PG) and an organic solvent such as an alkyl acetate as set out hereinbefore, preferably isopropyl acetate, or t-butyl methyl ether (MTBE), and optionally seeds of compound ((S)-PG) Ia (molar ratio of seeds Ia:compound B within the range from about 0.1 to about 10%, preferably from about 0.5% to about 3%), to form a crystal slurry of compound ((S)-PG) Ia and separating out crystalline compound ((S)-PG) Ia from the crystal slurry.

In carrying out the above telescoped reaction of Scheme I, the silyl reducing agent will be employed in a molar ratio to compound B within the range from about 1.2:1 to about 4.5:1, preferably from about 2:1 to about 4:1, while the activating group (Lewis acid) will be employed in a molar ratio to the silyl reducing agent within the range from about 1.2:1 to about 4.5:1, preferably from about 2:1 to about 4:1. (S)-propylene glycol ((S)-PG) will be employed in a molar ratio to compound B within the range from about 0.9:1 to about 1.5:1, preferably from about 0.98:1 to about 1.2:1; water will be employed in a molar ratio to the (S)-PG within the range from about 0.95:1 to about 5:1, preferably from about 0.99:1 to about 2:1.

The crystalline compound of the structure Ia ((S)-PG) form SC-3 of the invention may also be prepared according to the reaction Scheme II set out below.

SCHEME II

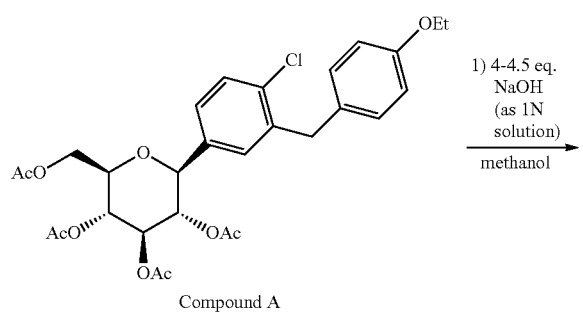

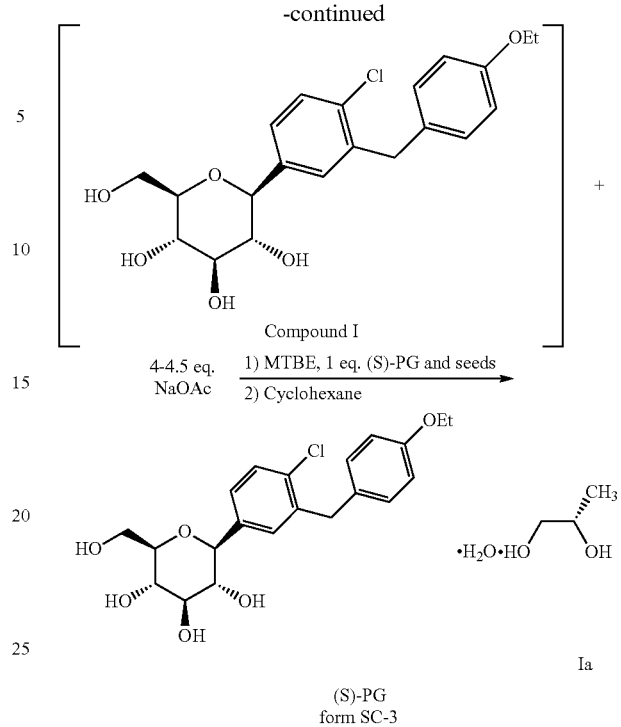

wherein compound A is treated with an alcohol solvent such as methanol, ethanol or isopropyl alcohol, preferably methanol, water and aqueous base such as an alkali metal hydroxide such as NaOH, KOH or LiOH, preferably NaOH, preferably under an inert atmosphere such as nitrogen, at an elevated temperature within the range from about 50 to about 85° C., preferably from about 60 to about 80° C. to form compound I.

The aqueous base will be employed in a molar ratio of compound A within the range from about 3.5:1 to about 5.5:1, preferably from about 3:1 to about 5:1.

The reaction mixture containing compound I is treated with an organic solvent such as methyl-butyl ether (MTBE) or an alkyl acetate as described above, preferably isopropyl acetate, or MTBE, to separate out compound I which is treated with (S)-propylene glycol to form a thick slurry containing crystalline product Ia (S)-PG, form SC-3. Optionally, seeds of compound ((S)-PG) Ia are added to the reaction mixture. The crystalline compound Ia is separated from the slurry employing conventional procedures, for example, the slurry of compound Ia is treated with an organic solvent such as cyclohexane, iso-octane or methyl cyclohexane, preferably cyclohexane, and crystalline compound Ia is recovered.

In carrying out the formation of compound Ia, the (S)-PG is employed in a molar ratio to compound I with the range from about 0.9:1 to about 1.5:1, preferably from about 0.98:1 to about 1.2:1.

As indicated herein before, the (R)-propylene glycol solvate Ib of compound I may be prepared in a manner similar to the corresponding (S)-propylene glycol solvate Ia except that (R)-propylene glycol is used in place of (S)-propylene glycol.

The process of the invention for preparing the mono-EtOH-dihydrate (ethanol or EtOH/structure) form SA-1 (compound Ic) is shown in Scheme III below.

SCHEME III

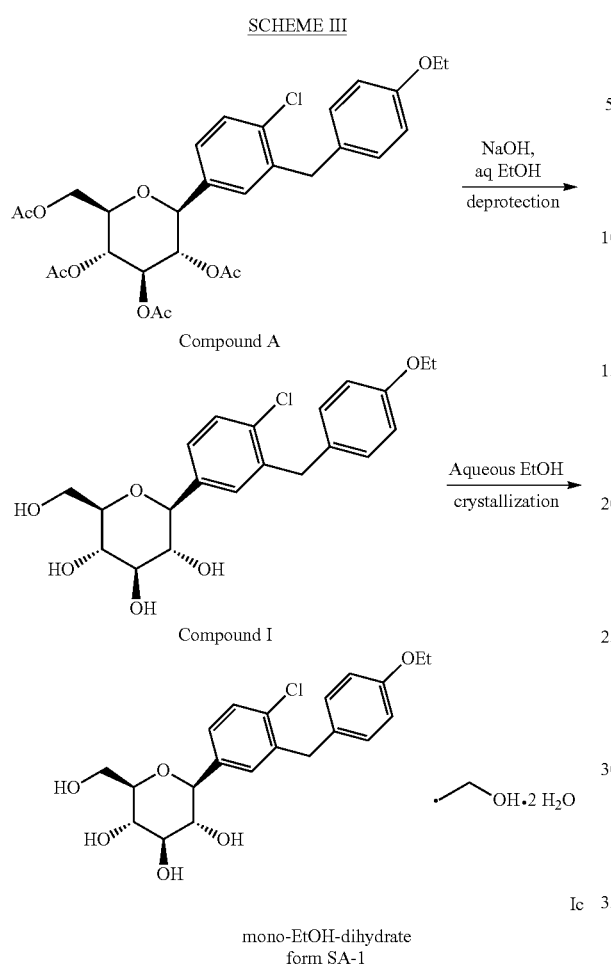

wherein compound A is dissolved in ethanol by heating to a boil then adding water in volume ratio to the ethanol within the range from about 1:1 to about 3:1, preferably from about 1.5:1 to about 2.5:1. Ethanol is added and the mixture cooled to a temperature with the range from about −10° C. to about −30° C., preferably from about −15° C. to about −25° C. Compound Ic is recovered as crystals of the mono-EtOH-dihydrate.

The process of the invention for preparing the ethylene glycol dihydrate structures form SB-1 and form SB-2 (compounds Id and Ie, respectively), is carried out as follows.

Compound Id form SB-1 is prepared by dissolving compound A in aqueous ethylene glycol (water:ethylene glycol from about 1:1 to about 0.4:1, preferably from about 0.7:1 to about 0.5:1), by heating at a temperature within the range from about 35 to about 55° C., preferably from about 40 to about 50° C., for about 1.5 to about 2 hours, preferably from about 0.30 min to about 1 hours. The mixture is cooled to a temperature within the range from about 10 to about 22° C., preferably from about 14 to about 16° C., and seeds of the mono-EtOH-dihydrate crystals Ic or ethylene glycol dihydrate crystals form SB-1 Id are added in a molar ratio to compound A within the range from about 0.1 to about 10%, preferably from about 0.5 to about 3%, to form the ethylene glycol dihydrate crystal form SB-1 Id.

In accordance with the present invention, the ethylene glycol dihydrate crystal form SB-2 Ie is formed by dissolving compound A in aqueous ethylene glycol (water:ethylene glycol from about 1:1 to about 0.4:1, preferably from about 0.7:1 to about 0.5:1), by heating at a temperature within the range from about 35 to about 55° C., preferably from about 40 to about 50° C., for about 1.5 to about 2 hours, preferably from about 0.30 min to about 1 hour. The mixture is cooled to a temperature within the range from about 10 to about 30° C., preferably from about 20 to about 25° C., and seeds of the ethylene glycol dihydrate crystals form SB-2 Ie are added in a molar ratio to compound A within the range from about 0.1 to about 10%, preferably from about 0.5 to about 3%, to form the ethylene glycol dihydrate crystal form SB-2 Ie.

The process of the invention for preparing the crystalline form of compound B, that is If, is carried out in accordance with Scheme IV set out below.

The crystalline 1,4-butyne-diol solvate If of the invention is prepared according to the following reaction Scheme IV.

SCHEME IV

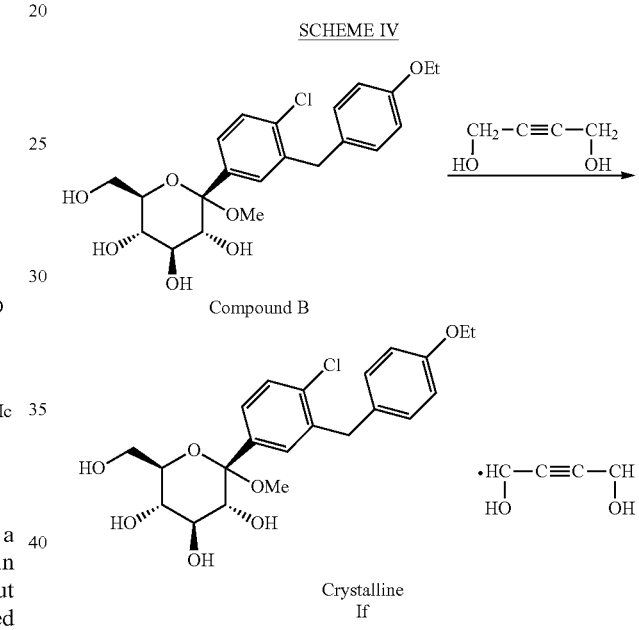

wherein non-crystalline compound B (which may be prepared as described in U.S. patent application Ser. No. 10/745,075 filed Dec. 23, 2003 or in U.S. Pat. No. 6,515,117), preferably in substantially pure form (for example 50 to 100% pure), is mixed with toluene/alkyl acetate (such as ethyl acetate), and the mixture heated to a temperature within the range from about 50 to about 70° C., preferably from about 55 to about 65° C., 2-butyne-1,4-diol is added and heated as above until the diol dissolves, seeds of compound If are added, and the mixture cooled to form crystals of compound If.

In an alternative process for preparing crystalline compound If, compound B is dissolved in an alkyl acetate (such as butyl acetate) or an alkyl acetate/heptane (0.5:1 to 1.5:1) mixture at an elevated temperature within the range from about 50 to about 70° C., preferably from about 55 to about 65° C., 1,4-butyne-diol is added, and the mixture is cooled to room temperature to form crystals of compound If.

In a preferred embodiment, compound If is crystallized from a mixture of compound B and toluene/alkyl acetate (preferably ethyl acetate) containing a volume ratio of toluene to alkyl acetate within the range from about 1:1 to about 19:1, preferably from about 4:1 to about 9:1. The mixture of toluene/alkyl acetate will include sufficient toluene to provide a molar ratio with compound B within the range from about 40:1 to about 90:1, preferably from about 60:1 to about 80:1, so as to enable formation of the 1,4-butyne-diol solvate If.

The crystallization to form 1,4-butyne-diol solvate If may be more easily effectuated employing seed crystals of compound If in an amount from about 0.1 to about 10%, preferably from about 0.5 to about 3% based on the weight of starting compound B.

In another preferred embodiment, compound If (which may or may not be purified) is crystallized from a mixture of compound B and alkyl acetate/heptane (preferably butyl acetate/toluene) optionally with seeding with seeds of crystalline compound If employing from about 0.1 to about 10%, preferably from about 0.5 to about 3% seeds of If based on the weight of starting compound B. The alkyl acetate will be employed in a volume ratio with heptane within the range from about 0.5:1 to about 2:1, preferably from about 1:1 to about 1:1.5.

The crystalline 1,4-butyne-diol solvate If may also be prepared in a continuous process as shown in Scheme IVA.

The synthesis of solvate If involves two sequential steps with compound E and compound D: (1) Lithiation of compound E to generate a lithiated intermediate G, and (2) coupling of the lithiated intermediate G with compound D.

SCHEME IVA

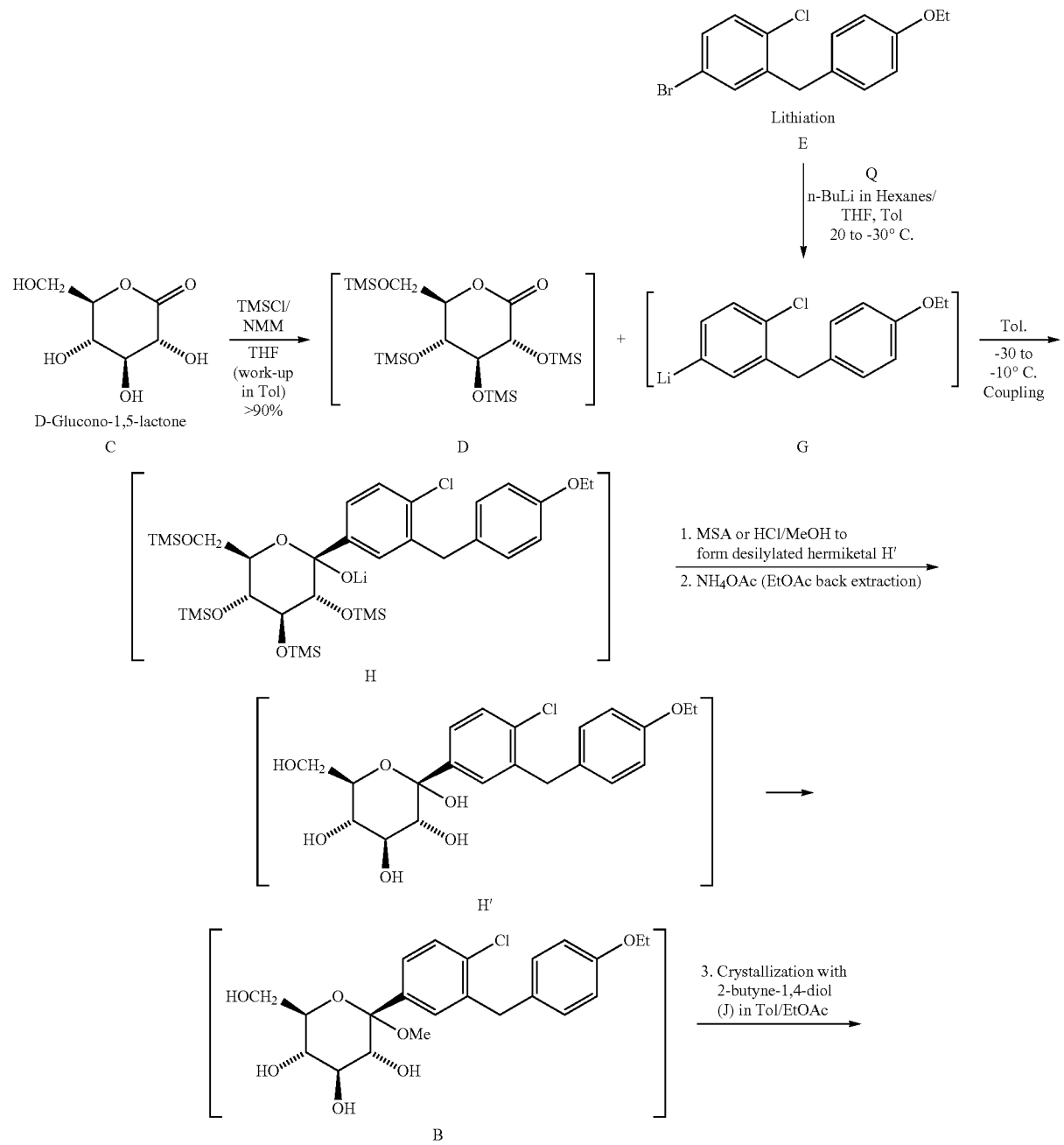

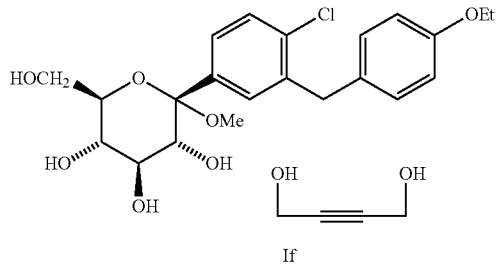

If

Figure 22:
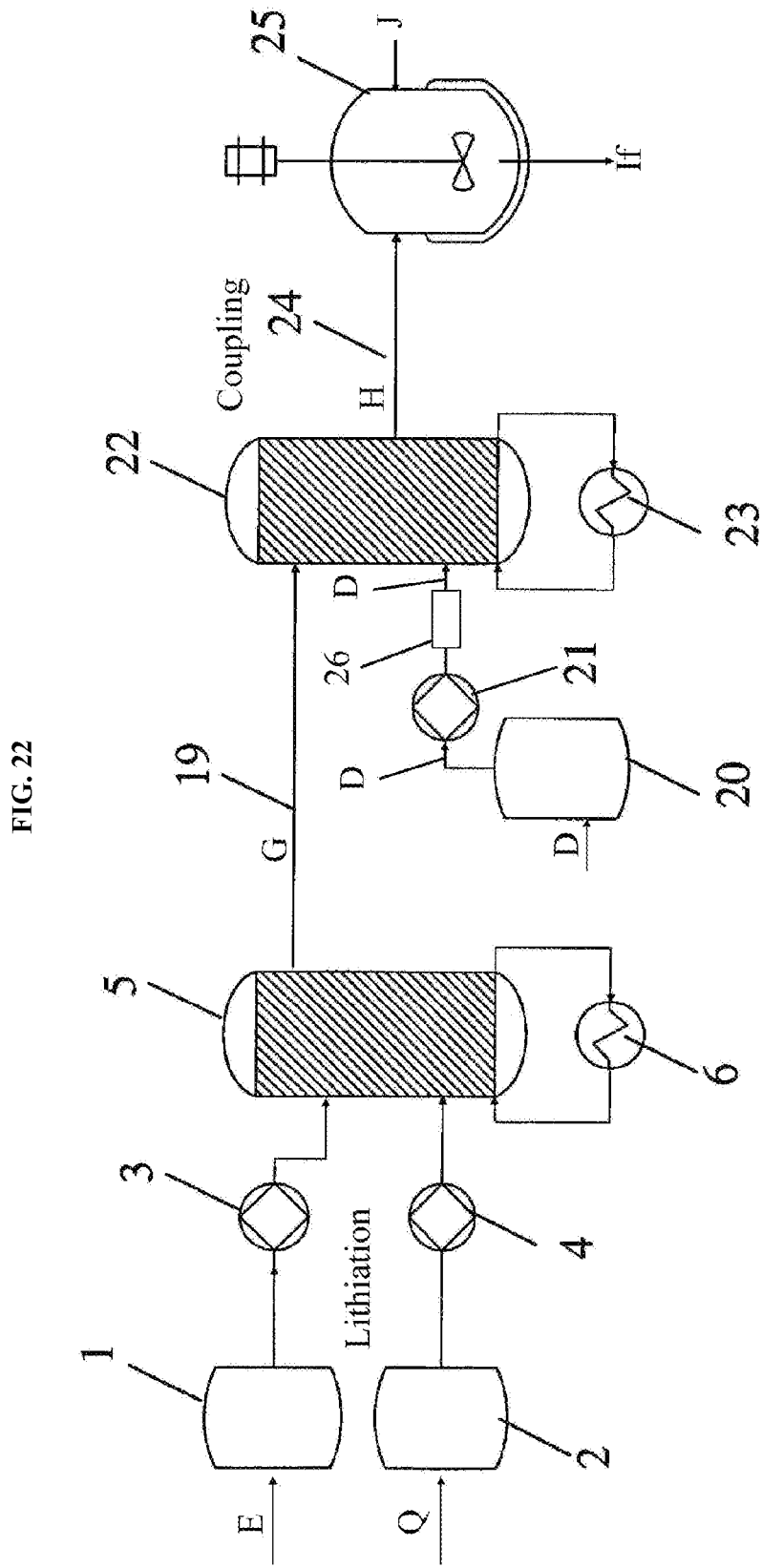
FIG. 22 is a schematic representation of a continuous reaction set-up.

Referring now to FIG. 22, a schematic process flow diagram (similar to that disclosed in U.S. Pat. No. 7,164,015 which is incorporated herein by reference), is shown. In this embodiment, the entire process for preparing compound If as shown in Scheme IVA is performed under non-cryogenic conditions. An aromatic reactant E having a group suitable for Li and halogen exchange is stored in a first vessel 1 at room temperature. A lithium reagent Q is fed into a second vessel 2, also at room temperature. The aromatic reactant E and the lithium reagent Q are transferred from the vessels 1 and 2 via pumps 3 and 4, respectively, to a first jacketed static mixer 5. The temperature of a reaction to produce a lithiated anion species is regulated at from about −30° C. to about 20° C., in the first mixer 5 by a chiller 6.

The lithiated anion species G thus formed is fed directly from the first mixer 5 to a second static mixer 22 along a conventional transfer line 19. A carbonyl substituted reactant D is fed into a third vessel 20 at room temperature and is transferred via pump 21 through chiller 26 where it is chilled to a temperature within the range from about −10 to about −30° C., and then passed to the second jacketed static mixer 22. A reaction to produce a glycoside product H is regulated in the second mixer 22 by a second chiller 23.

Further processing under glycosidation conditions occurs where H is fed into a conventional reactor 25 where it is treated with acid in an alcohol solvent, preferably MSA/MeOH or HCl/MeOH, to form H' (desilylated hemiketal) which further converts to glycoside B. Further additional work-up and back extraction and crystallization with 2-butyne-1,4-diol (J) in toluene/EtOAc produces crystalline product If. The reactor 25 may be maintained at room or other non-cryogenic temperature during the course of any subsequent reactions.

The lithium reagent used is desirably an organo lithium reagent. Suitable organo lithium reagents include n-BuLi, s-BuLi and t-BuLi. Others will be apparent to those having ordinary skill in the art.

After completion of the reaction, the desired product If can be isolated and purified according to techniques widely known in the field of organic chemistry (e.g. precipitation, solvent extraction, recrystallization, and chromatography). The deprotected compound If may itself be a useful intermediate or end product. The compound If may be further reacted to obtain pharmaceutically acceptable acid addition or base salts thereof using methods that will be known to those having ordinary skill in the art.

Temperature and reaction time are two important parameters in the continuous process design shown in Scheme IVA: the lithiation can be operated continuously from −30° C. (or lower) up to 20° C. (or higher), preferably from about −17° to about −10° C., with minutes to seconds of reaction time. For the subsequent coupling reaction, the stream of lithiated derivative G is further mixed with the compound D stream (the third feed) in a mixer. The mixed flow can be then sent to a flow reactor if extra reaction time is needed for completion. The coupling reaction can be operated continuously at higher temperatures from −30° C. to −10° C. (or higher), preferably from about −30° to about −20° C., with minutes to seconds of reaction time. The coupling stream is then sent to a batch reactor for further reactions as described herein. With continuous processing, both lithiation and coupling reactions can be well integrated and operated at higher temperatures utilizing smaller flow reactors with efficient temperature control, compared with cryogenic batch reactors on scale.

The operating temperature of continuous lithiation in the above process can be as high as 20° C. (not limited to), preferably −17 to −10° C., while generating >95 RAP, of the desired lithiated intermediate G.

In the coupling reaction, the coupling product from the above process at −20° C. to −30° C., preferably ranged in 70-79 RAP.

Compound If may be employed to prepare crystalline intermediate A as shown in Scheme IVB.

SCHEME IVB
Preparation of Intermediate A

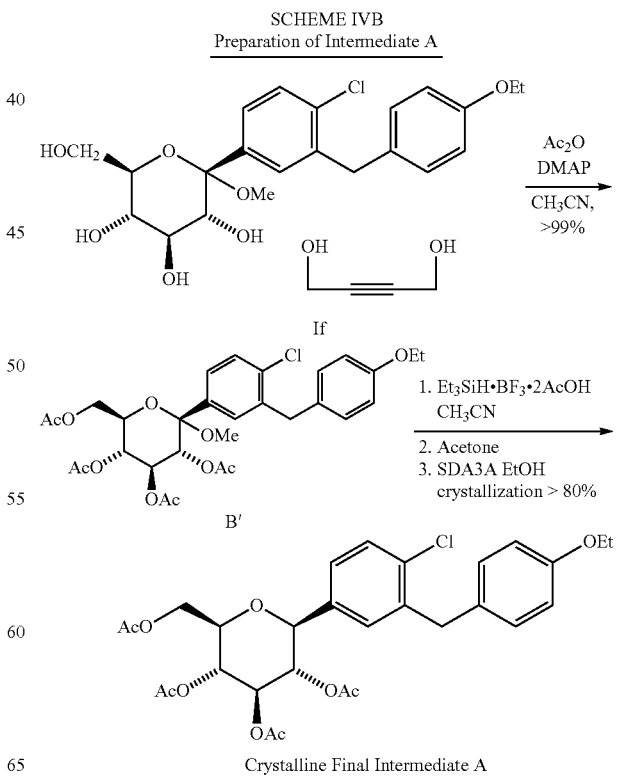

Crystalline Final Intermediate A

Referring to Scheme IVB, solid compound If, solid DMAP, liquid acetonitrile, and liquid acetic anhydride are heated to a temperature within the range from about 70 to about 85° C. and held until reaction is complete.

The batch is cooled (e.g. 5° C.). Triethylsilane and boron trifluoride acetic acid complex or other Lewis acid (as described with respect to Scheme I) are added to the reaction mixture. After completion of the reaction, acetone or other solvent is added. The batch is warmed (for example from about 20 to about 30° C.) and held until triethylsilane is consumed. Aqueous $NH_4OAc$ is added and the batch is mixed, and allowed to settle until upper and lower phases form. Batch volume of product in the rich upper phase is reduced by distilling off acetonitrile to minimum agitation. SDA3A Ethanol is added at elevated temperature (>60° C.).

The product A crystallizes out by cooling or cooling with seeding (5 wt % based on compound If wet-milled, nitrogen jet milled, or a previous batch).

The product is recrystallized as either a wet or dry cake from SDA3A ethanol.

The crystalline dimethanol solvate Ig of the invention is prepared according to the following reaction Scheme V.

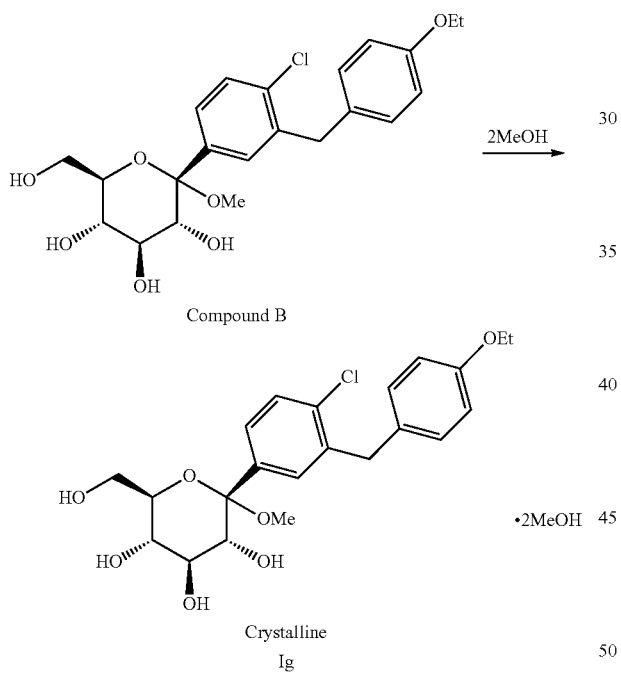

wherein non-crystalline compound B (which may be prepared as described in U.S. patent application Ser. No. 10/745,075 filed Dec. 23, 2003 or in U.S. Pat. No. 6,515,117), preferably in substantially pure form (50 to 100% pure), is dissolved in methanol, a mixture of methanol/toluene, or a mixture of methanol/toluene/heptane, a mixture of methanol/methyl t-butyl ether (MTBE)/heptane, or a mixture of methanol/toluene/ethyl acetate or other alkyl acetate with stirring, to form a white slurry containing crystalline dimethanol solvate Ig. The crystalline dimethanol solvate Ig may be recovered from the slurry using conventional procedures, such as filtration.

The above process may be carried out at room temperature, although elevated temperatures of up to about 20-25° C. may be employed to enhance crystallization.

In a preferred embodiment, compound Ig is crystallized from a mixture of methanol/toluene containing a volume ratio of methanol to toluene within the range from about 6:1 to about 1:1, preferably from about 3:1 to about 5:1. The mixture of methanol/toluene will include sufficient methanol to provide a molar ratio with compound B within the range from about 80:1 to about 10:1, preferably from about 40:1 to about 20:1, so as to enable formation of the dimethanol solvate Ig.

The crystallization to form dimethanol solvate Ig may be more easily effectuated employing seed crystals of compound Ig in an amount from about 0.1 to about 10%, preferably from about 0.5 to about 3% based on the weight of starting compound B.

In another preferred embodiment, compound Ig (which may or may not be purified) is crystallized from a mixture of methanol/toluene/heptane with seeding with seeds of crystalline compound Ig employing from about 0.1 to about 10%, preferably from about 0.5 to about 3% based on the weight of starting compound B. The methanol will be employed in a volume ratio with toluene within the range from about 1:0.5 to about 1:6, preferably from about 1:1.5 to about 1:2.5, and a volume ratio of heptane:toluene within the range from about 2:1 to about 0.5:1, preferably from about 1.3:1 to about 0.5:1.

The crystalline complex 1:2 L-proline Ih of the invention is prepared according to the following reaction Scheme VI.

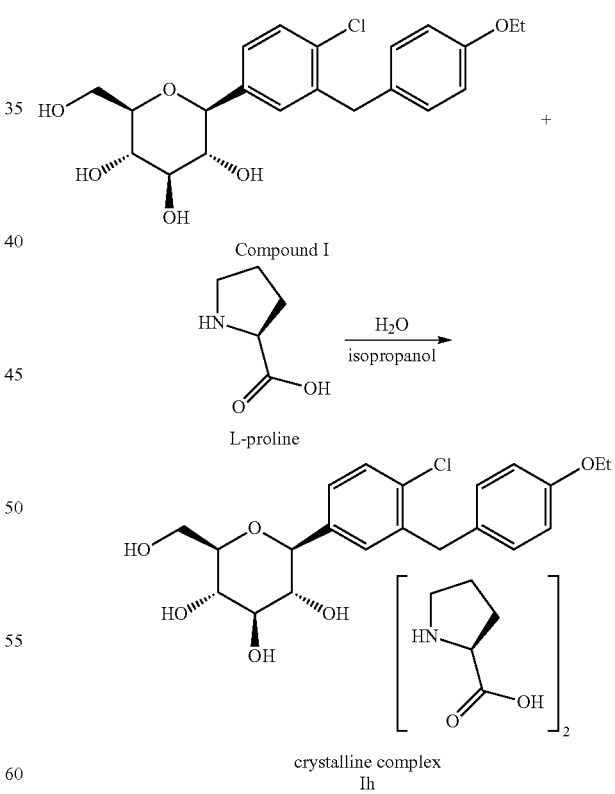

wherein a solution of L-proline in water is heated to a temperature within the range from about 70 to about 90° C. and an alcohol solvent such as methanol, ethanol or isopropyl alcohol, preferably isopropyl alcohol, is added. A solution of compound I is added to the above L-proline solution (which is stirred), wherein compound I is employed in a molar ratio to L-proline of about 0.5:1. The solution is cooled slowly to room temperature during which time solids form. The solution is filtered to remove solids which are washed with alcohol solvent. The solids are dried and recovered in the form of a white solid which is the 1:2 L-proline crystalline complex Ih, form 3, N-1.

The crystalline 1:1 L-proline complex Ii of the invention is prepared according to the following reaction Scheme VII.

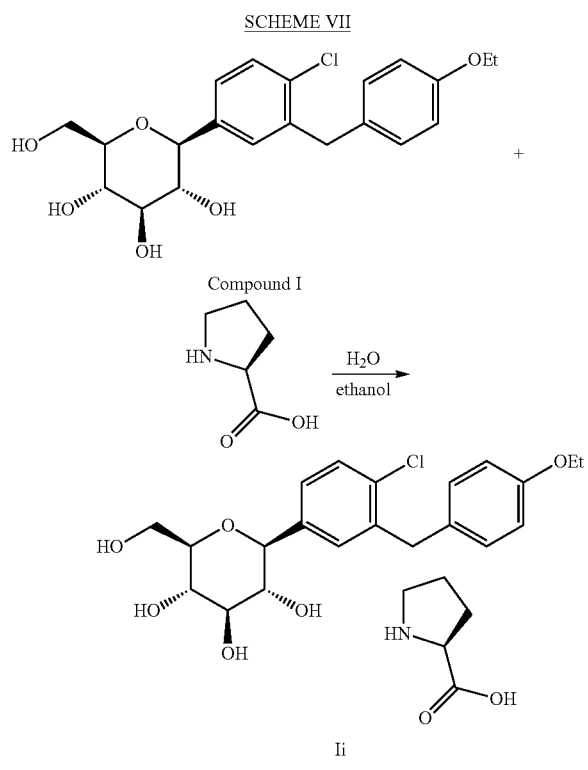

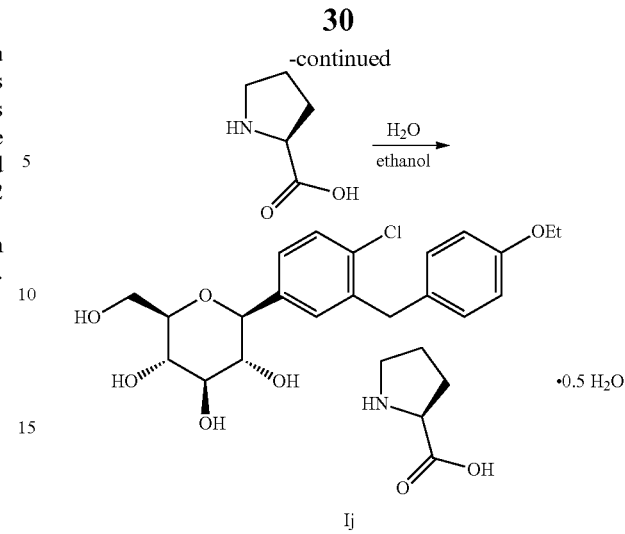

wherein a solution of L-proline and compound I (4.34 g, 10 mmol) in ethanol/water is heated to 70° C. to give a clear solution. The resulting solution is cooled from −20 to −25° C. and seed crystals of 1:1 complex with L-proline Ii are added. After 3 days at −20° C., solids are collected via filtration, and the filter cake is washed with cold (−20° C.) ethanol. The resulting solids are suspended and recovered as a white crystalline solid Ij, H0.5-2 employing conventional procedures.

The crystalline L-phenylalanine complex Ik of the invention is prepared according to the following reaction Scheme IX.

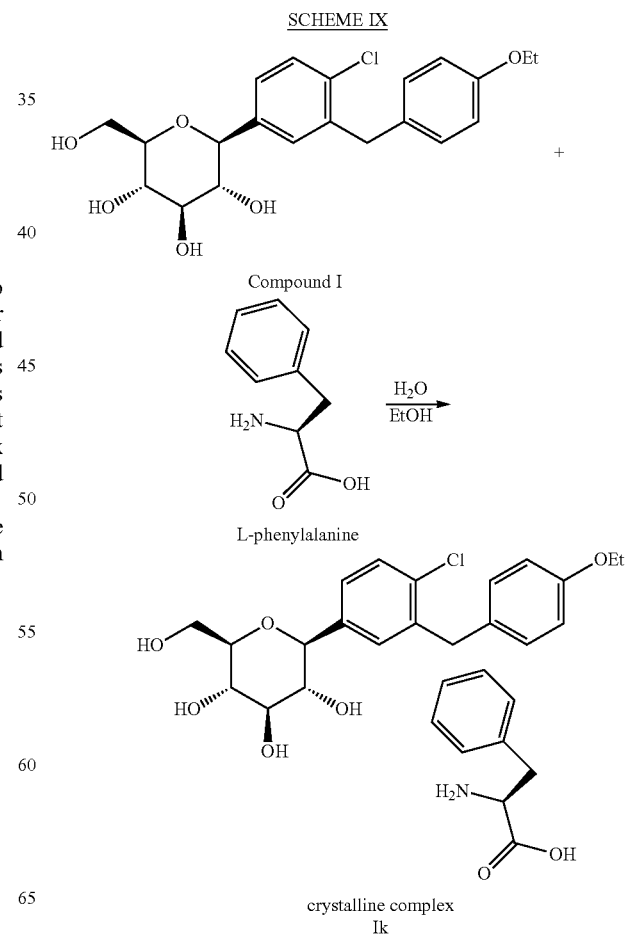

A solution of L-proline in ethanol/water is heated to boiling and a solution of compound I in ethanol or other alcohol solvent is added. The resulting solution is cooled from −10 to −25° C. at which time solids form, which solids are the 1:1 crystalline complex with L-proline Ii which is recovered employing convention procedures. In carrying out the above procedure for preparing the 1:1 L-proline complex Ii, the L-proline is employed in a molar ratio to compound I within the range from about 1:4 to about 1:6.

The crystalline L-proline hemihydrate complex Ij of the invention is prepared according to the following reaction Scheme VIII.

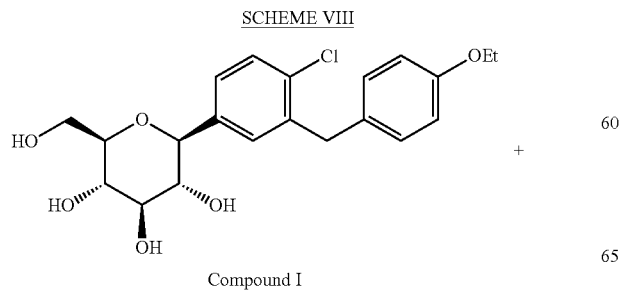

L-phenylalanine is dissolved in water with heating. The resulting solution is filtered and added to an ethanol (or other alcohol) solution containing compound I. The resulting solution is heated at from 70 to 90° C. and allowed to cool slowly to room temperature (crystal formation is observed at 55° C.). The solution is subjected to conventional recovery procedures. The L-phenylalanine complex Ik is recovered as a white solid identified as 1:1 complex of compound I with L-Phe.

The following examples are provided to describe the invention in further detail. These examples, which set forth the best mode presently contemplated for carrying out the invention, are intended to illustrate and not to limit the invention.

The preparation of compounds of formula I is generally described in U.S. Pat. No. 6,414,126, and specifically described in Scheme 1 and Example 1 of U.S. Pat. Nos. 5,515,117. 6,414,126, and 5,515,117 incorporated by reference herein in their entirety. Stable forms of compounds of formula (I) can be crystallized as solvates (e.g., hydrates).

EXAMPLES

Preparation of Crystal Structures

Example 1

Preparation of (S)-Propylene Glycol ((S)-PG) Structure—Form SC-3—Formula Ia

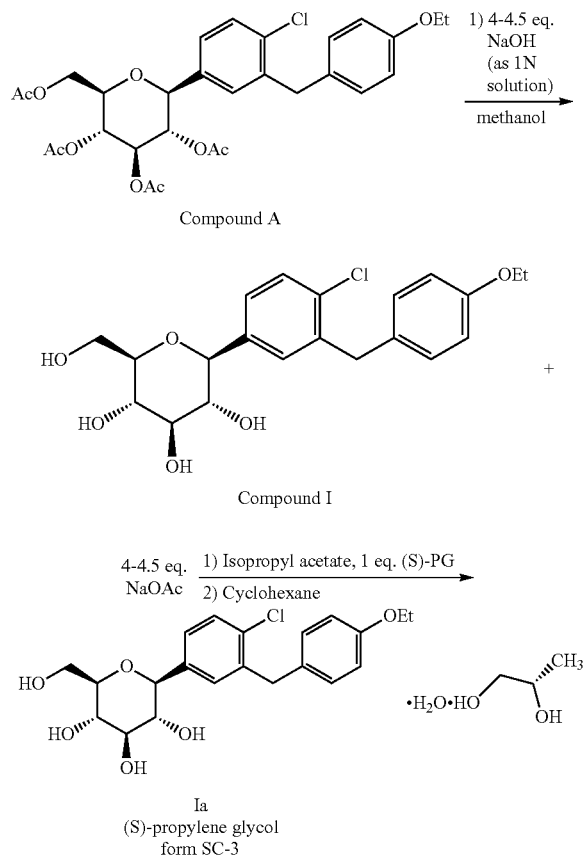

Compound A can be prepared as described in Example 1, Part E of U.S. Pat. No. 6,515,117.

A 10-L glass reactor equipped with a thermocouple and a nitrogen inlet was charged with MeOH (1.25 L), deionized water (3.6 L) followed by 50% aqueous NaOH (205.9 ml, 3.899 mol). The residual solution of NaOH in the measuring cylinder was transferred with water (94 ml) to the reaction vessel. Compound A (503.11 g, 0.872 mol) was added and the mixture was stirred and heated to ~68° C. over 1.5 h. After 1 h, the circulation bath temperature was lowered from 80 to 70° C.; internal temperature became 65° C. After a total of 3 h HPLC[1] indicated completion of reaction, Compound I AP ~99.5. After the mixture was cooled to 25° C., isopropyl acetate (2.5 L) was added. The mixture was stirred for 10 minutes and then the aqueous layer was separated (pH=12.5) and organic layer was washed with water (1 L). During this wash the pH of the biphasic system was adjusted to 6.0 with conc. HCl (5.0 ml) and then the aqueous layer was separated.[2] The organic layer was collected in a separate vessel. The reactor was washed with water (2 L), MeOH (2 L) and flushed with nitrogen gas. The wet solution of compound B was recharged into the reactor and (S)-propylene glycol ((S)-PG) (67.03 g, 0.872 mole) was introduced. Optionally, seed crystals of (S)-PG Ia may be added at this stage. Instantaneous crystallization produced a thick slurry. After stirring for 1 h, cyclohexane (2.5 L) was added rapidly over 10 minutes and the stirring was continued for 21 h. The product was filtered through a filter paper (Whatman #5, Buchner funnel 24" diameter). The filtration was rapid and took about 15 minutes. The filter cake was washed with a mixture (1:1) of MTBE/cyclohexane (2×1 L) and dried under suction for 0.5 h. The solid was transferred to a pyrex tray and dried under vacuum (25 mm Hg) in an oven at 25-30° C. for two days till water analysis by KF corresponded to monohydrate (3.6 wt. %). The (S)-PG product Ia was obtained (0.425 kg, yield 97%) as a snow white solid, HPLC[3] AP 99.7.

[1] BRUKER AXS. Inc., 5465 East Cheryl Parkway Madison, Wis. 53711 U.S.A.
[2] Otwinowski, Z. & Minor, W. (1997) in *Macromolecular Crystallography*, eds. Carter, W. C. Jr & Sweet, R. M. (Academic, NY), Vol. 276, pp. 307-326
[3] Collect Data collection and processing user interface: Collect: Data collection software, R. Hooft, Nonius B. V., 1998

Seed crystals may be prepared by dissolving compound I in a solvent such as MTBE and treating the resulting solution with (S)-propylene glycol and proceeding as described above without the use of seeding.

[1]HPLC: Column: YMC ODS-A (C-18) S3, 4.6×50 mm. Solvent A: 0.2% aq. $H_3PO_4$. Solvent B: 90% $CH_3CN$/10% $H_2O$ Start % B=0, final % B=100 Gradient time 8 min; hold time 3 min. Integration stop time 11.0 min. Flow rate 2.5 ml/min. UV wave length 220 nm.

[2]Neutralization before phase split was done to prevent contamination of the product with NaOH. (S)-PG structure prepared without neutralization was slightly basic [pH 8.3 of a suspension sonicated in water (~20 mg/ml)].

[3]HPLC method: Mobile Phase A: 0.05% TFA in $H_2O$. Mobile Phase B: 0.05% TFA in CAN. Column: YMC Hydrosphere 4.6×150 (3µ). Gradient: 30-90% B over 45 minutes, hold 5 minutes; back to 30% B and re-equilibrate for 10 min. Wavelength: 220 nm. Injection Volume: 10 µl. Temperature: Ambient

Example 1A

(S)-Propylene Glycol ((S)-PG) Structure—Form SC-3—Formula Ia

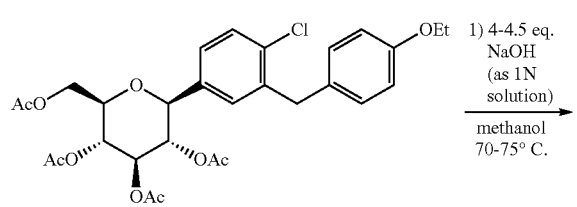

Compound A
C$_{29}$H$_{33}$ClO$_{10}$
Exact Mass: 576.18
Mol. Wt.: 577.02
C, 60.36; H, 5.76; Cl, 6.14; O, 27.73

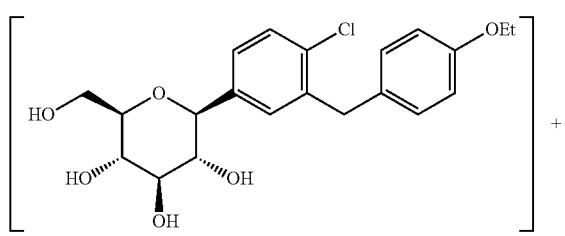

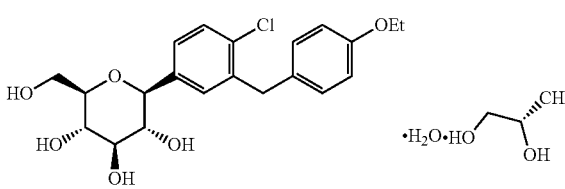

I
C$_{24}$H$_{35}$ClO$_9$
Exact Mass: 502.20
Mol. Wt.: 502.98
C, 57.31; H, 7.01; Cl, 7.05; O, 28.63

Procedure 20 g of compound A was charged to a reactor at ambient temperature and pressure. 30 mL Methanol and 49.75 mL 3N NaOH were added to the reactor and the reaction mixture was heated to 80° C. or reflux, and held about 2-3 hours for reaction completion <0.5 AP. The batch was cooled to 20° C. and neutralized to pH 6.0-7.5 using con. HCl or 1N acetic acid (requires ~1 mL/gm input).

Extraction

The product was extracted from the reaction mixture into 100 mL isopropyl acetate, the aqueous phase was split away and the organic phase washed with water until conductivity <10 mS (~4 mL/gm input). The aqueous phase was split away.

Crystallization 2.8 g (1.05 eq) (S)-(+)-1,2 Propanediol was added to the reaction mixture. The batch was seeded with 0.1 g compound I seed. 160 mL Cyclohexane was added and the batch cooled to from room temperature to 5° C. The batch was allowed to stir at from room temperature to 5° C. at least 1 hour before isolation.

Isolation and Drying

Each load of isolated cake was washed with 50/50 by volume isopropyl acetate/cyclohexane mixture. The cake was dried at 30° C. in a vacuum oven under full vacuum. (Cake is dry when KF=3.6%-4.1%).

Yield=84% (uncorrected)

Typical purity=99.81AP

Typical PG content=15.1-15.8% by GC

Example 2

Preparation of (R)-Propylene Glycol Structure—Ib

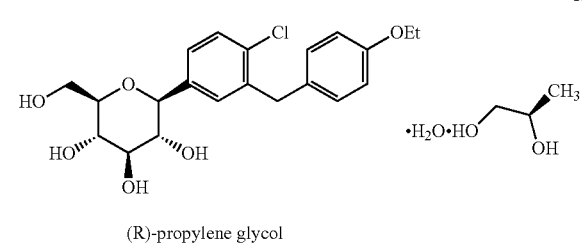

(R)-propylene glycol

The (R)-propylene glycol structure was prepared using the same process as described above for the (S)-propylene glycol structure Ia (Example 1) except that (R)-propylene glycol was used in place of (S)-propylene glycol.

Example 3

Preparation of Mono-EtOH-Dihydrate (Ethanol or EtOH Structure)—Form SA-1—Formula Ic

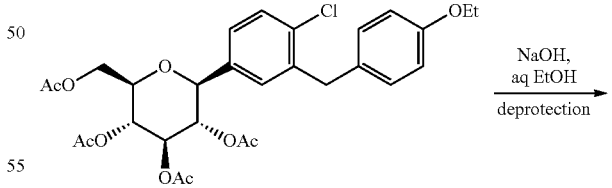

Compound A

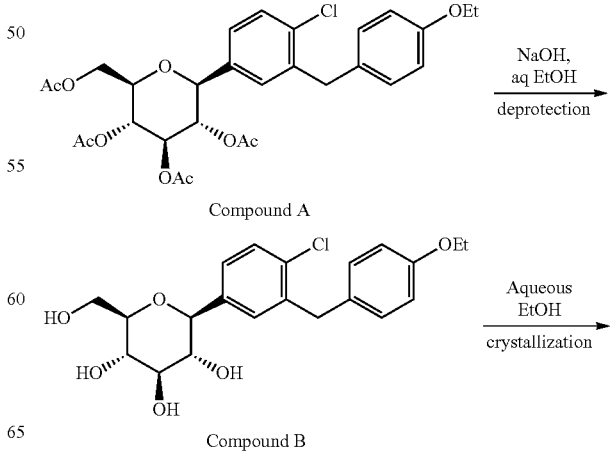

Compound B

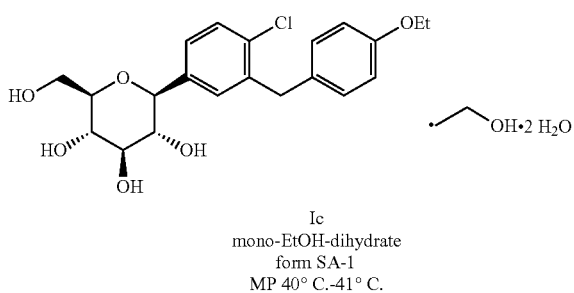

Ic
mono-EtOH-dihydrate
form SA-1
MP 40° C.-41° C.

Compound A (1.0 g) was dissolved in EtOH (3.0 ml) by heating to a boil and the solution was diluted with water (7 ml). 1 ml EtOH was added and the mixture was divided in three portions for crystallization at 20° C., 5° C. and −20° C. After cooling to −10 to −20° C., crystals were formed which have M.P. 40-41° C.

Examples 4 and 5

Preparation of Ethylene Glycol Structure Forms SB-1 and SB-2—Formulation Id and Ie, Respectively

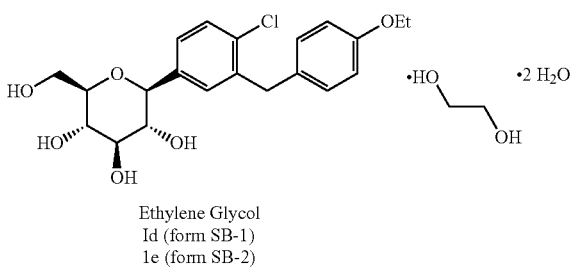

Ethylene Glycol
Id (form SB-1)
Ie (form SB-2)

To obtain the polymorphic form of the ethylene glycol dihydrate crystal form SB-1 Id, compound A (0.5 gm) was dissolved in aqueous ethylene glycol (0.3 mL water: 0.5 ml ethylene glycol) by heating at 45° C. for 30 min. Upon cooling to room temperature, seeds of the SB-1 (10 mg) were added. The reaction mixture was stirred for 16 hrs, to provide white crystalline solid. The crystals were filtered, washed with water and dried. To obtain the polymorphic form of the ethylene glycol dihydrate seed crystals form SB-1 Id, compound A was dissolved in aqueous ethylene glycol (S)-propylene glycol crystal form SC-3 Ia were added to obtain the ethylene glycol dihydrate crystal form SB-1 Id (Example 4). These crystals were filtered and washed with excess water.

To obtain the polymorphic form of the ethylene glycol dihydrate crystal form SB-2 Ie (Example 5), Compound A was dissolved in aqueous ethylene glycol by heating. Upon cooling, seeds of the mono-EtOH-dihydrate crystal form SA-1, Ic were added to obtain the ethylene glycol dihydrate crystal form SB-2 Ie (Example 5). These crystals were filtered and washed with excess water.

$^1$H NMR for forms SB-1 and SB-2: $^1$H NMR (400 MHz, DMSO) δ 1.29 (t, 3H, J=6.98 Hz, —CH3) 3.15 (m, 4H,), 3.33 (bs, 6H, —CH2), 3.42 (m, 3H), 3.6 (bdd, J=11.4 Hz, 1H), 3.9 (bm, 5H, H-1, -2CH$_2$), 4.43 (t, 1H, J=7.4 Hz, OH), 4.86 (d, 1H, J=2.4, OH), 4.95 (q, 1H, —OH), 6.82 (d, 2H, J=11.47 Hz, Ar—H), 7.8 (d, 2H, J=11.4 Hz, Ar—H), 7.22 (dd, 1H, J=2.5 Hz, J=11.4 Hz, Ar—H), 7.35 (t, 2H, J=10.96, Ar—H; $^{13}$C NMR (400 MHz, DMSO) δ 12.49, 59.16, 60.61, 60.69, 68.10, 72.51, 76.11, 78.51, 79.02, 112.09, 125.16, 126.47, 127.38, 128.61, 129.02, 129.73, 135.62, 137.48, 154.70.

Example 6

Preparation of (S)-PG Solvate Form SC-3 Ia

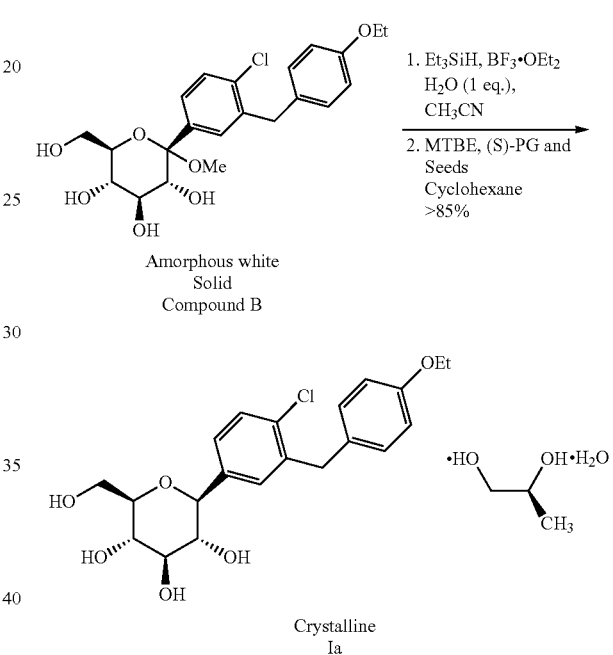

To acetonitrile (12 mL), at batch temperature of 8-10° C. under nitrogen atmosphere, was charged borontrifluoride diethyletherate (2.3 mL, 18.4 mmol) and water (0.82 mL, 4.6 mmol). After holding the above mixture for about 1 hour, triethylsilane (3 mL, 18.4 mmol) was added. The resulting mixture was held for about 1 hour, and then compound B (prepared as described in Example 17) in 10 mL acetonitrile was added. The batch was held at 5 to 10° C. On completion of the reaction as determined by HPLC, the reaction mixture was quenched with aqueous ammonium acetate (24 mL; 85 g) in 200 mL water. The phases were separated and product rich organic phase was dried over sodium sulfate. The product rich organic phase was concentrated under reduced pressure.

Water (13 mg, 0.7 mmol, based on 0.3 g crude compound B input), (S)-propylene glycol (56 mg, 0.7 mmol), t-butyl-methyl ether (5 mL, ~17 mL/g compound B input), compound Ia seeds (~20 mg) were mixed and held for 1 hr., to form a crystal slurry. Cyclohexane (10 mL, 33 mL/g compound B (input)) was added. The crystalline product (Ia) was isolated by filtration (4-5%) and dried in vacuo at 20-25° C.

Example 7

Preparation of Crystalline MeOH Solvate Ig

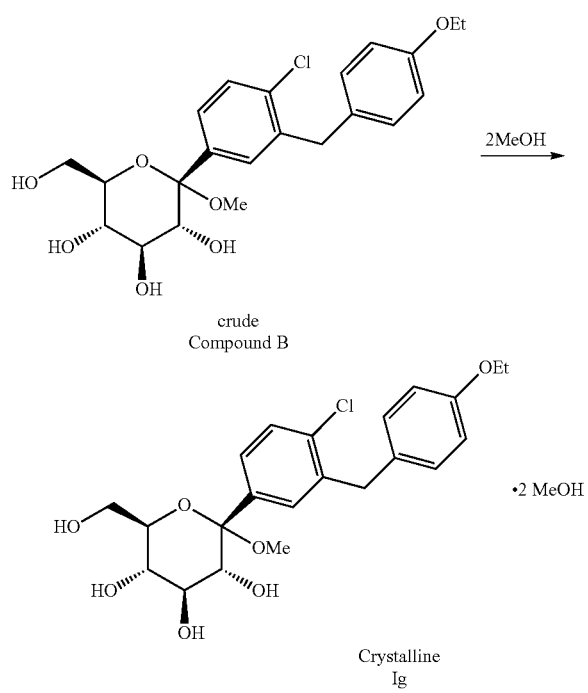

Crystals of methanol solvate Ig were obtained by dissolving pure compound B in methanol and stirring at room temperature. A white slurry formed after a few days, and was found to be crystalline methanol solvate Ig.

The so formed crystalline di-MeOH solvate Ig may be used in place of compound B in the preparation of crystalline compound Ia as described in Example 6.

Example 8

Preparation of Crystalline Di-MeOH Solvate Ig from Unpurified Compound B in 80/20 Methanol/Toluene Using Seeds 6 g of compound B (HPLC AP approximately 80%) was dissolved in 15 mL of 80/20 methanol/toluene.

Seeds (about 1% of starting compound B) of compound Ig crystals were added and the mixture was cooled to form a slurry containing crystals.

The slurry was stirred for 6 hours before isolating.

The wet cake was found to be crystalline methanol solvate If but loses crystallinity if left open for a few hours.

Example 9

Preparation of Crystalline Di-MeOH Solvate Ig from Unpurified Compound B in Methanol/Toluene/Heptane Using Seeds 2.5 g of compound B (91.5%) was added to a scintillation vial with a magnetic stir-bar.

4 mL toluene was added to dissolve the compound Ia.

2 mL methanol was added. Next, seeds of compound Ig crystals (about 1%) were added.

4 mL heptane was added over 30 minutes and the mixture was stirred for 12 hours. Wet cake was isolated on a Buchner funnel. The wet cake was found to be crystalline methanol solvate Ig. It was dried under vacuum at 30° C. The resultant powder lost crystallinity.

Figure 10:
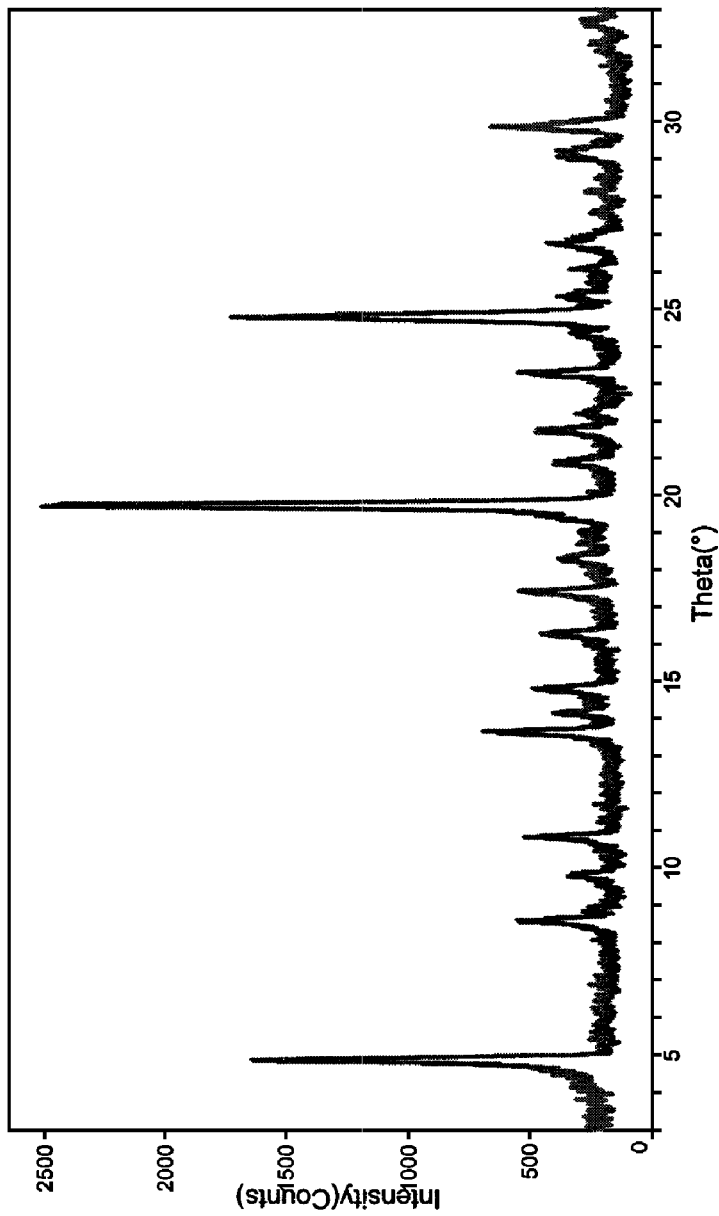
FIG. 10 shows an observed (experimental at room temperature) powder X-ray diffraction pattern of the dimethanol solvate crystalline structure Ig.

Yield=1.7 g=74.5% (corrected). Characterization XRD pattern of crystals: FIG. 10.

The so formed crystalline MeOH solvate Ig may be used in place of compound B in the preparation of crystalline compound Ia as described in Example 6.

Example 10

Preparation of Crystalline 1,4-Butyne-diol Solvate If from Compound B in Toluene/Ethyl Acetate Using Seeds 1,4-Butyne-diol solvate can be crystallized in an alkyl acetate (e.g. ethyl, propyl or butyl acetate), alcohol (e.g. isopropanol, butanol) or even water. Toluene and heptane act as anti-solvents when crystallized in alkyl acetate.

50 g (90.3 weight %) Compound B was dissolved in 675 mL toluene. The solution was heated to 60° C. and 75 mL ethyl acetate added. 1.5 eq 2-butyne-1,4-diol (=13.3 g) was added and the mixture held at 60° C. until the butyne diol dissolved. The solution was cooled to 55° C. and 0.1% seeds (50 mg) of 1,4-butyne-diol compound If was added. The mixture was held for 1 hour at 55° C. Compound If started crystallizing. The mixture was cooled to 25° C. over 6 hours. The resulting slurry was stirred for 3 hours before isolating (mother liquor conc was <3 mg/mL), filtered and washed with 180 mL toluene+20 mL ethyl acetate, and dried under vacuum at 45° C. to yield crystals of 1,4-butyne-diol solvate If.

HPLC AP=99.5%. Potency=80.7 weight % (Expected potency=83.6% for 1:1 solvate). Yield=95%.

Example 11

Preparation of Crystalline 1,4-Butyne-diol Solvate If from Compound B in Butyl Acetate/Heptane 0.5 g Compound B (91 weight %) was dissolved in 3.5 mL butyl acetate+3.5 mL heptane at 60° C. 1.5 eq 2-Butyne-1,4-diol was added and the mixture cooled to room temperature. The resulting slurry was stirred for 12 hours, filtered and washed with 1 mL 1:1 butyl acetate:heptane, and dried under vacuum at 50° C. to yield crystals of 1,4-butyne-diol solvate If. Potency=85.1%. Yield=90%.

The 1,4-butyne-diol solvate If may be employed in place of compound B and employing the Lewis acid $BF_3 \cdot 2CH_3COOH$ in place of $BF_3 \cdot OEt_2$ to form the crystalline compound Ia.

Example 12

Preparation of 1:2 Crystalline Complex with L-Proline—Structure Ih, Form 3

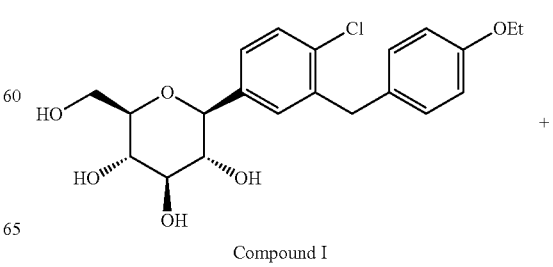

Compound I

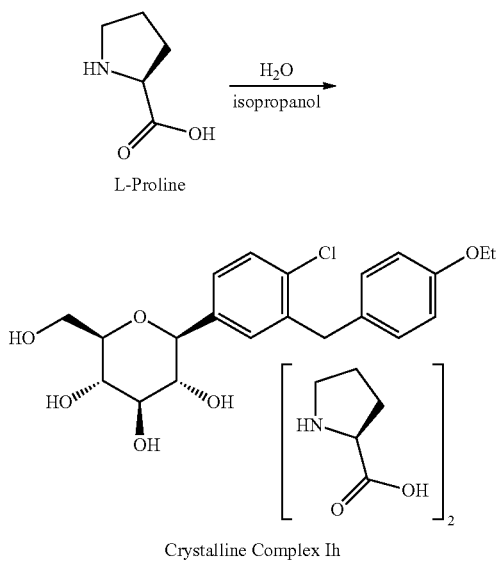

L-Proline

Crystalline Complex Ih

A solution of L-proline (11.5 g, 100 mmol) in 10 mL of water was heated to 80° C. and 100 mL and isopropanol was added. To the rapidly stirred solution of L-proline was added a room temperature solution of compound I (21.4 g, 50 mmol) in 100 mL of isopropanol. Solids formed, and the solution was cooled slowly to room temperature. The solution was filtered and the resulting solids were washed with isopropanol followed by hexanes. The solids were dried under vacuum oven to give 30.4 g of a white solid containing compound I as a 1:2 crystalline complex with L-proline (structure Ih, form 3).

Example 13

Preparation of 1:1 Crystalline Complex with L-Proline—Structure Ii, Form 6

Crystalline Complex Ii

A solution of L-proline (0.23 g, 0.2 mmol) in 1.1 mL of 90% ethanol/water was briefly heated to boiling and a solution of compound I (0.4 g, 1 mmol) in 4 mL of ethanol was added. The resulting solution was cooled to −20° C. for 2 h during which time solids formed. The solution was stored at room temperature for 2 days. The vessel was centrifuged and the supernatant was removed. The remaining solids were washed in 1 mL of MTBE, and the solids were dried under vacuum to give 0.025 g of a white solid containing compound I in a 1:1 crystalline complex with L-proline (structure Ii, form 6).

Example 14

Preparation of Crystalline Form H.5-2 of L-Proline Compound I Hemihydrate—Structure Ij

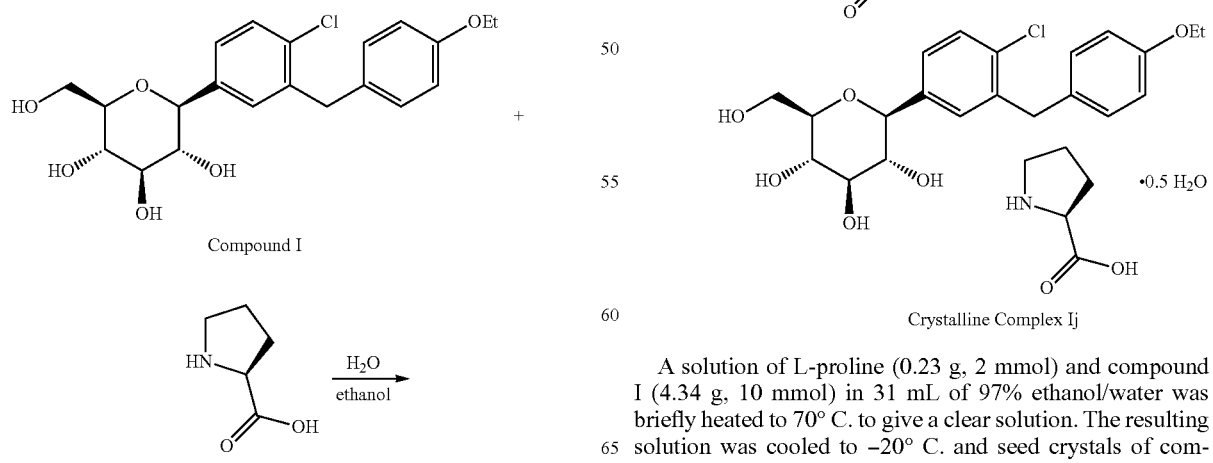

Crystalline Complex Ij

A solution of L-proline (0.23 g, 2 mmol) and compound I (4.34 g, 10 mmol) in 31 mL of 97% ethanol/water was briefly heated to 70° C. to give a clear solution. The resulting solution was cooled to −20° C. and seed crystals of compound I 1:1 complex with L-proline structure Ii form 6 were added. After 3 days at −20° C., solids were collected via filtration, and the filter cake was washed with cold (−20° C.) ethanol. The resulting solids were suspended in 5 mL of heptane, followed by filtration and washing with heptane to give 0.3 g of a white solid. The material (0.02 g) was further crystallized from 20/1 EtOH/H₂O with slow evaporation of solvent and slight heating/cooling to grow larger X-ray quality crystals containing a ratio of 4 molecules of compound I, 4 molecules of L-proline and 2 molecules of water per unit cell, hemihydrate of 1:1 complex with L-proline (structure Ij form H.5-2).

Example 15

Preparation of 1:1 Crystalline Complex with L-Phenylalanine—Structure Ik, Form 2

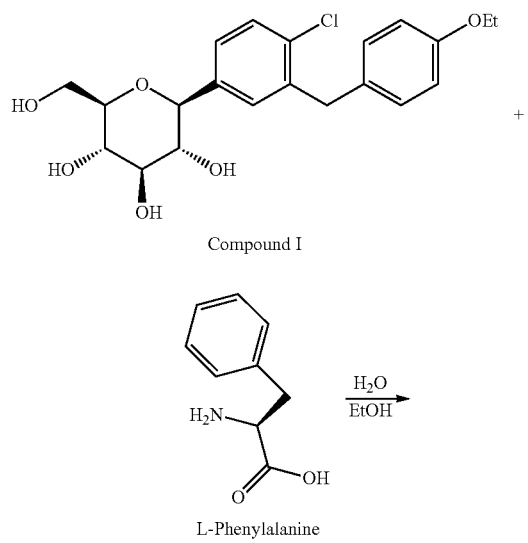

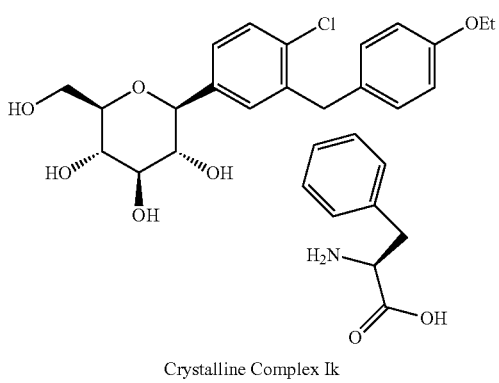

Crystalline Complex Ik

L-phenylalanine (424 mg, 2.56 mmol) was dissolved in 6 mL of water at 80° C. The resulting solution was filtered and added to an ethanol solution (6.5 mL) containing 1 gram of compound I (2.36 mmol). The resulting solution was heated to 80° C. and allowed to cool slowly to room temperature (crystal formation was first observed at 55° C.). The solution was stored at 4° C. The solution was filtered and the crystals were washed with 20% water/ethanol to give a complex of L-Phe:compound I. This material was further recrystallized from 10 mL of 50% water/ethanol as above to give 910 mg of a white solid identified as 1:1.3 complex of compound I with L-Phe (64%) structure Ik, form 2 as determined by $^1$H NMR integration.

Example 16

Preparation of Compound If Via Continuous Lithiation and Coupling Reactions

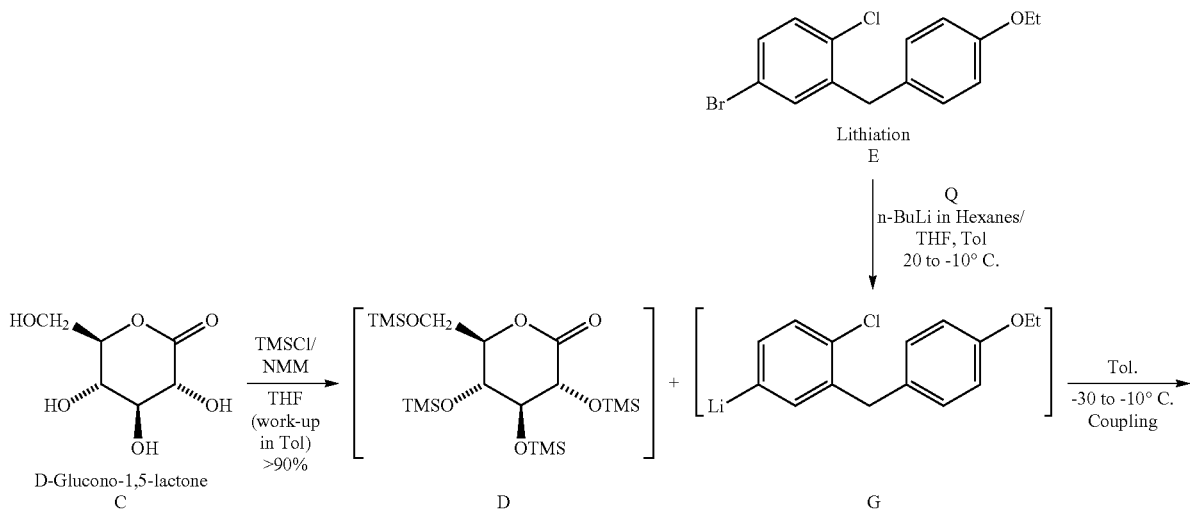

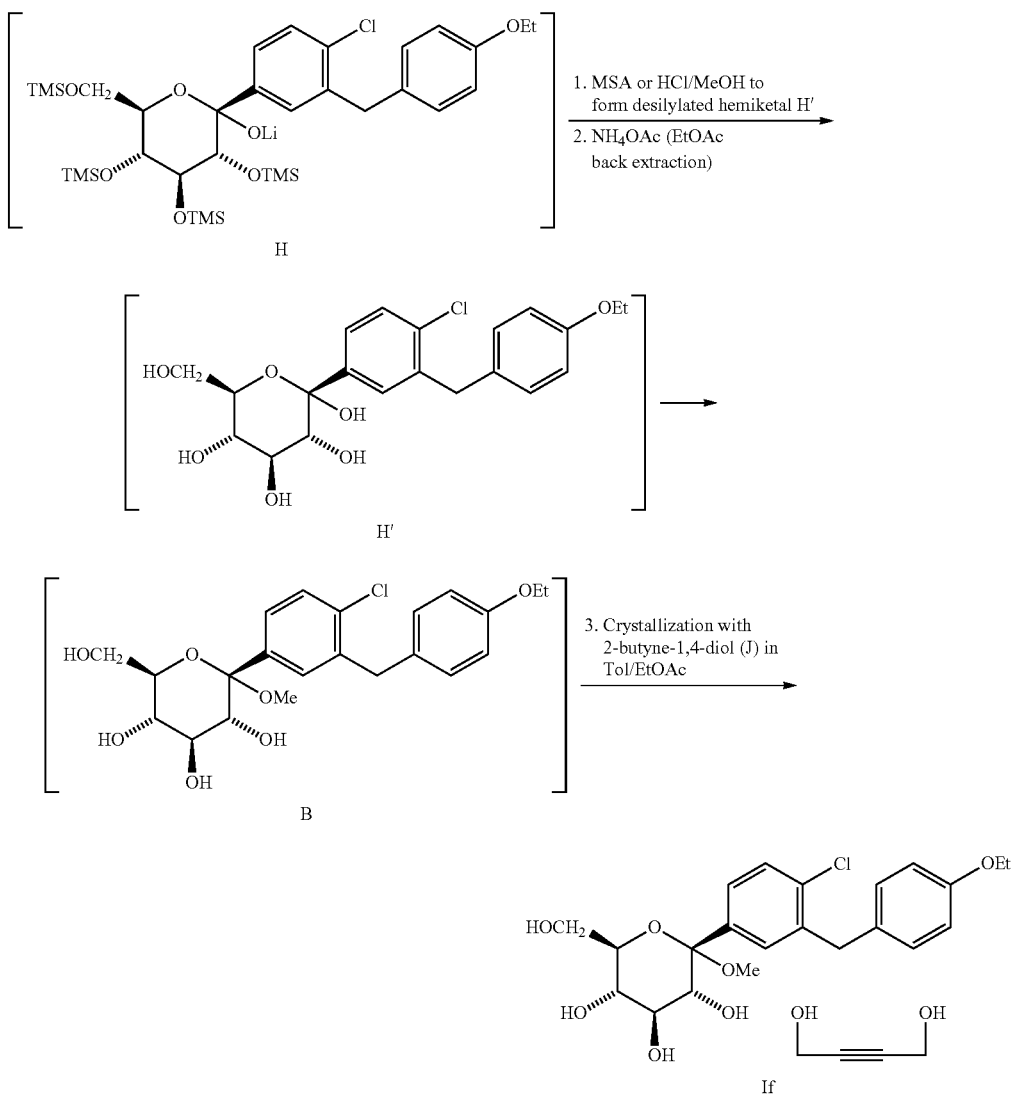

A reaction scheme similar to that shown in Scheme IVA and FIG. 22 was employed.

A −30° C. chiller for the lithiation reactor 5 (jacketed static mixer 5) was set up.

A −30° C. chiller for the coupling reactor 22 (jacketed static mixer 22) and a pre-cooling heat exchanger (not shown in FIG. 22) for the compound D/toluene feed was set up.

Continuous Lithiation

The two feeds of E/THF/toluene (2.74 ml/min) and Q, namely, n-BuLi in hexane (0.41 ml/min), were mixed and combined through jacketed static mixer 5 (−30° C.).

Before pumping the D/toluene feed, toluene (2.96 ml/min) was sent into the system as a make-up flow to maintain the overall flow constant at 6.1 ml/min.

Samples at the outlet of the lithiation static mixer 5 for HPLC analysis were collected. Samples were taken before (a) the onset of the coupling reaction, and (b) after the collection of the reaction mixture into the MSA-MeOH reactor.

Continuous Coupling Reaction

The D/toluene feed (2.96 ml/min) was pre-cooled via a heat exchanger before mixing with the lithiation stream.

The two streams namely G and D were mixed and combined through a jacketed static mixer 22 (between −24° C. and −30° C.).

The reaction stream appeared yellowish in color.

Samples were collected at the outlet of the mixer 22 for HPLC analysis. Samples were taken before and after the collection into the MSA-MeOH reactor 25.

Methyl Glycosidation

The coupling reaction stream 24 was fed to a 500-ml reactor 25 containing MSA and methanol or HCl/MeOH at <−10° C. with stirring.

After the collection were finished, the reaction mixture was kept at <−10° C. with stirring for another hour.

The reaction mixture was heated up to 35° C. The reaction was deemed complete (about 6 hrs) until HPLC analysis indicated that desilylated hemiketal H' RAP <0.3%. The reaction was cooled to room temperature (20° C.) and the reaction mixture was held for 16 hrs to form compound B.

Formation of Crystals of If

B was crystallized with 2-butyne-1,4-diol (J) in toluene/EtOAc to yield crystals of If.

Example 17

Preparation of Intermediate A

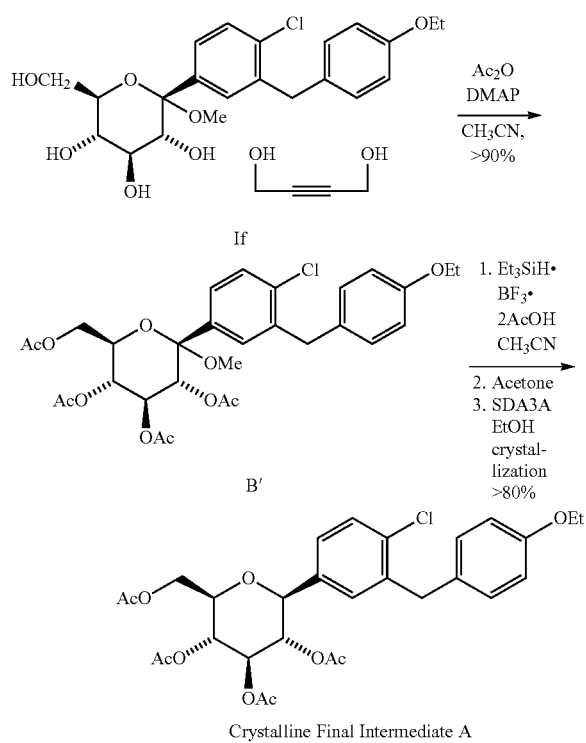

Crystalline Final Intermediate A

Solid compound If (50.0 g), solid DMAP (1.2 g), liquid acetonitrile (450 mL), and liquid acetic anhydride (63 mL) were charged to a 250 ml flask reactor.

The batch (77° C.) was heated and held until reaction complete.

The batch was cooled (5° C.).

Triethylsilane (72 mL), and boron trifluoride acetic acid complex (63 mL) were charged to the reactor.

After completion of the reaction, acetone (36 mL) was added.

The batch (21° C.) was warmed and held until triethylsilane was consumed.

Aqueous $NH_4OAc$ (33 wt %, 450 mL) was added and the batch was mixed, allowed to settle until upper and lower phases formed.

Batch volume of product in the rich upper phase was reduced by distilling off acetonitrile to minimum agitation. Ethanol SDA3A (1 L) was charged at elevated temperature (>60° C.).

The product was crystallized by cooling or cooling with seeding (5 wt % based on compound If wet-milled, nitrogen jet milled, or a previous batch). The product was typically isolated in >75% yield.

The product was recrystallized as either a wet or dry cake from ethanol SDA3A.

Crystal Structure Characterization

Crystal structures equivalent to the crystal structures described below and claimed herein may demonstrate similar, yet non-identical, analytical characteristics within a reasonable range of error, depending on test conditions, purity, equipment and other common variables known to those skilled in the art.

Accordingly, it will be apparent to those skilled in the art that various modifications and variations can be made in the present invention without departing from the scope and spirit of the invention. Other embodiments of the invention will be apparent to those skilled in the art from consideration of the specification and practice of the invention disclosed herein. Applicants intend that the specification and examples be considered as exemplary, but not limiting in scope.

X-Ray Powder Diffraction

One of ordinary skill in the art will appreciate that a powder X-ray diffraction pattern may be obtained with a measurement error that is dependent upon the measurement conditions employed. In particular, it is generally known that intensities in a X-ray powder diffraction pattern may fluctuate depending upon measurement conditions employed. It should be further understood that relative intensities may also vary depending upon experimental conditions and, accordingly, the exact order of intensity should not be taken into account. Additionally, a measurement error of diffraction angle for a conventional powder X-ray powder diffraction pattern is typically about 5% or less, and such degree of measurement error should be taken into account as pertaining to the aforementioned diffraction angles. Consequently, it is to be understood that the crystal structures of the instant invention are not limited to the crystal structures that provide X-ray diffraction patterns completely identical to the X-ray powder diffraction patterns depicted in the accompanying Figures disclosed herein. Any crystal structures that provide powder X-ray diffraction patterns substantially identical to those disclosed in the accompanying Figures fall within the scope of the present invention. The ability to ascertain substantial identities of X-ray powder diffraction patterns is within the purview of one of ordinary skill in the art.

(S)-PG (Form SC-3) Ia, (R)-PG Ib, 1,4-Butyne-diol Solvate If and Dimethanol Solvate Ig, Hemihydrate of 1:1 L-Proline Complex Ij (H.5-2), 1:2 L-Proline Complex Ih and 1:1 L-Proline Complex Ii Structures About 200 mg were packed into a Philips powder X-ray diffraction (PXRD) sample holder. The sample was transferred to a Philips MPD unit (45 KV, 40 mA, Cu $K\alpha_1$). Data were collected at room temperature in the 2 to 32 2-theta rage (continuous scanning mode, scanning rate 0.03 degrees/sec., auto divergence and anti scatter slits, receiving slit: 0.2 mm, sample spinner: ON).

Figure 2:
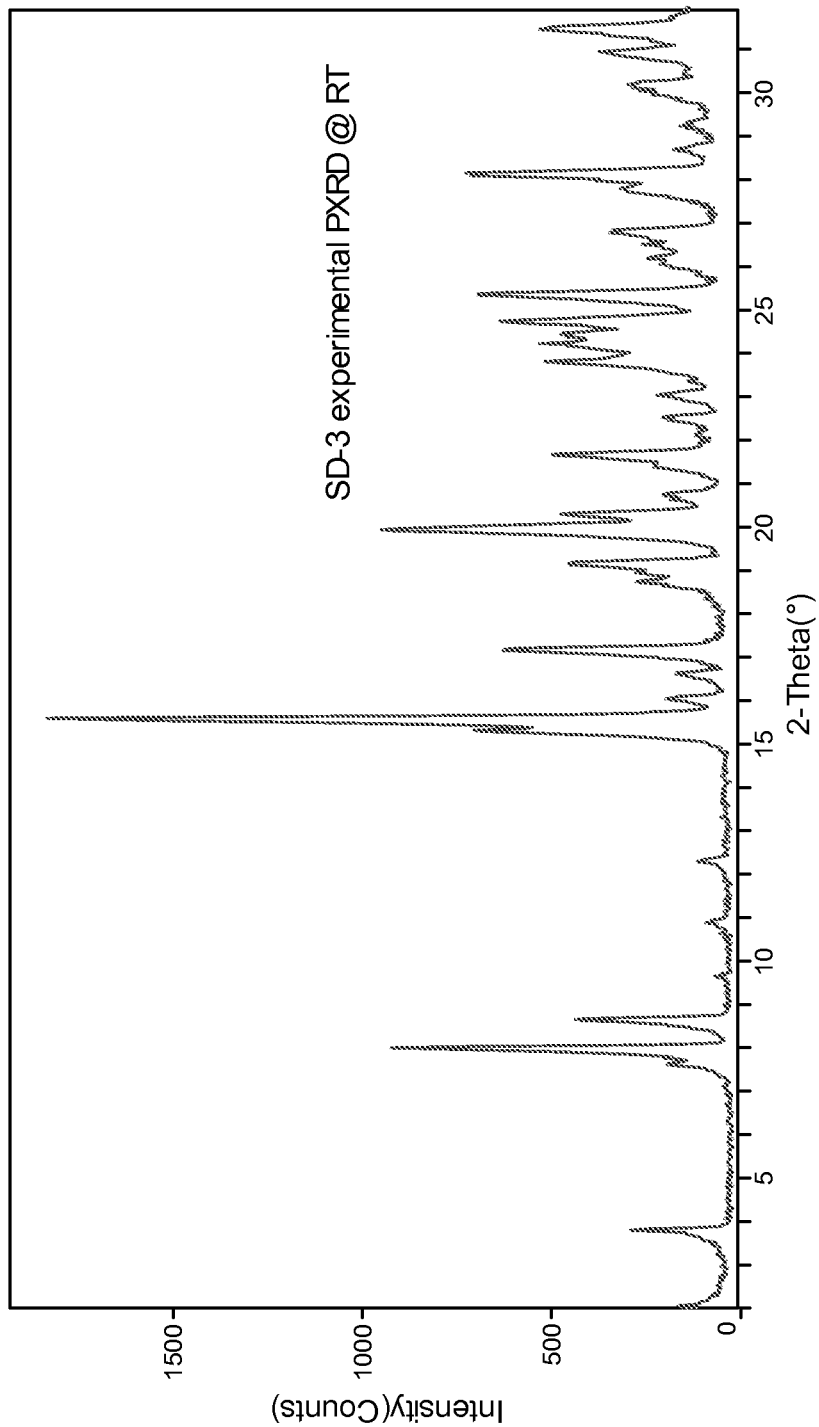
FIG. 2 shows observed (experimental at room temperature) powder X-ray diffraction pattern of the (R)-PG crystalline structure Ib.
Figure 9:
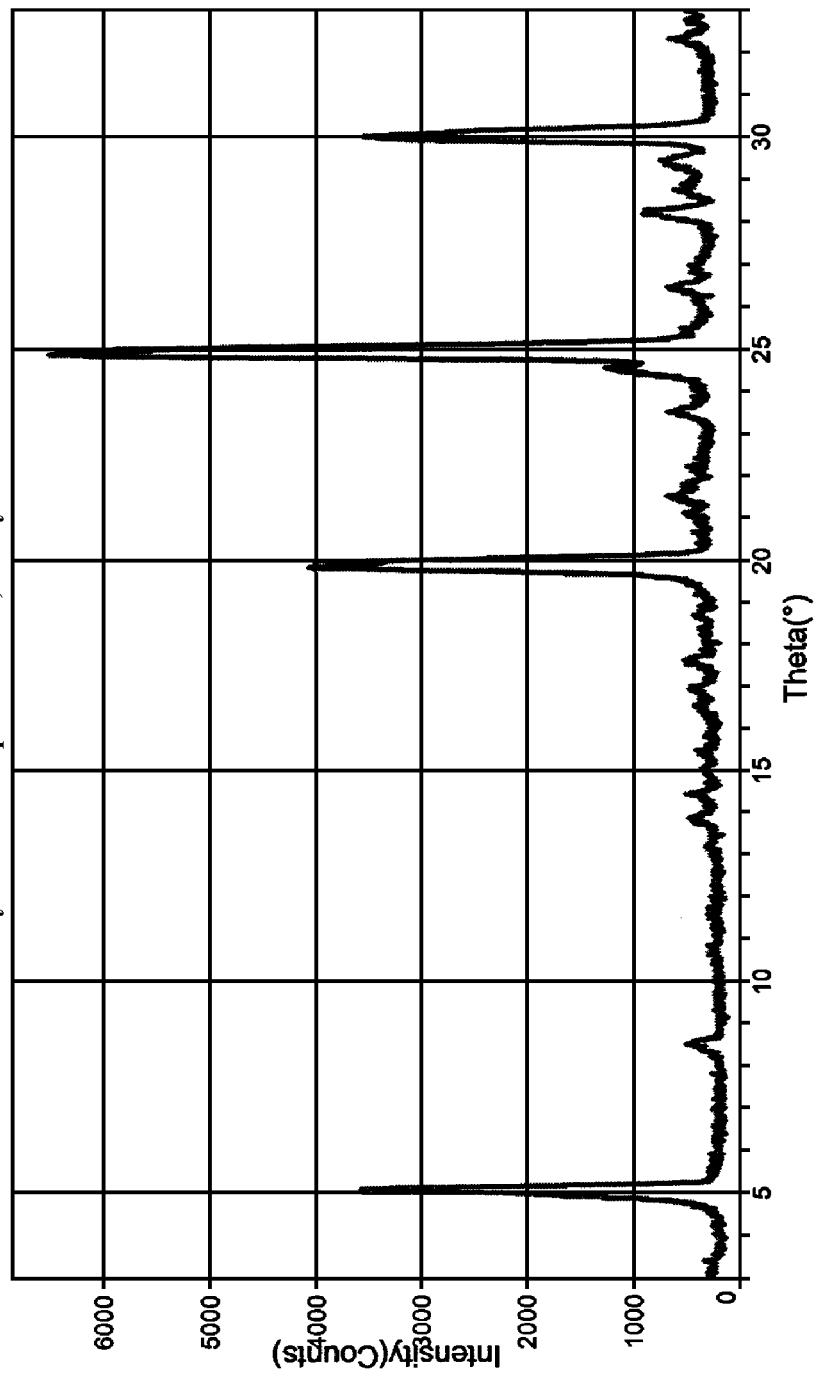
FIG. 9 shows an observed (experimental at room temperature) powder X-ray diffraction pattern of the 1,4-butyne-diol solvate crystalline structure If.
Figure 13:
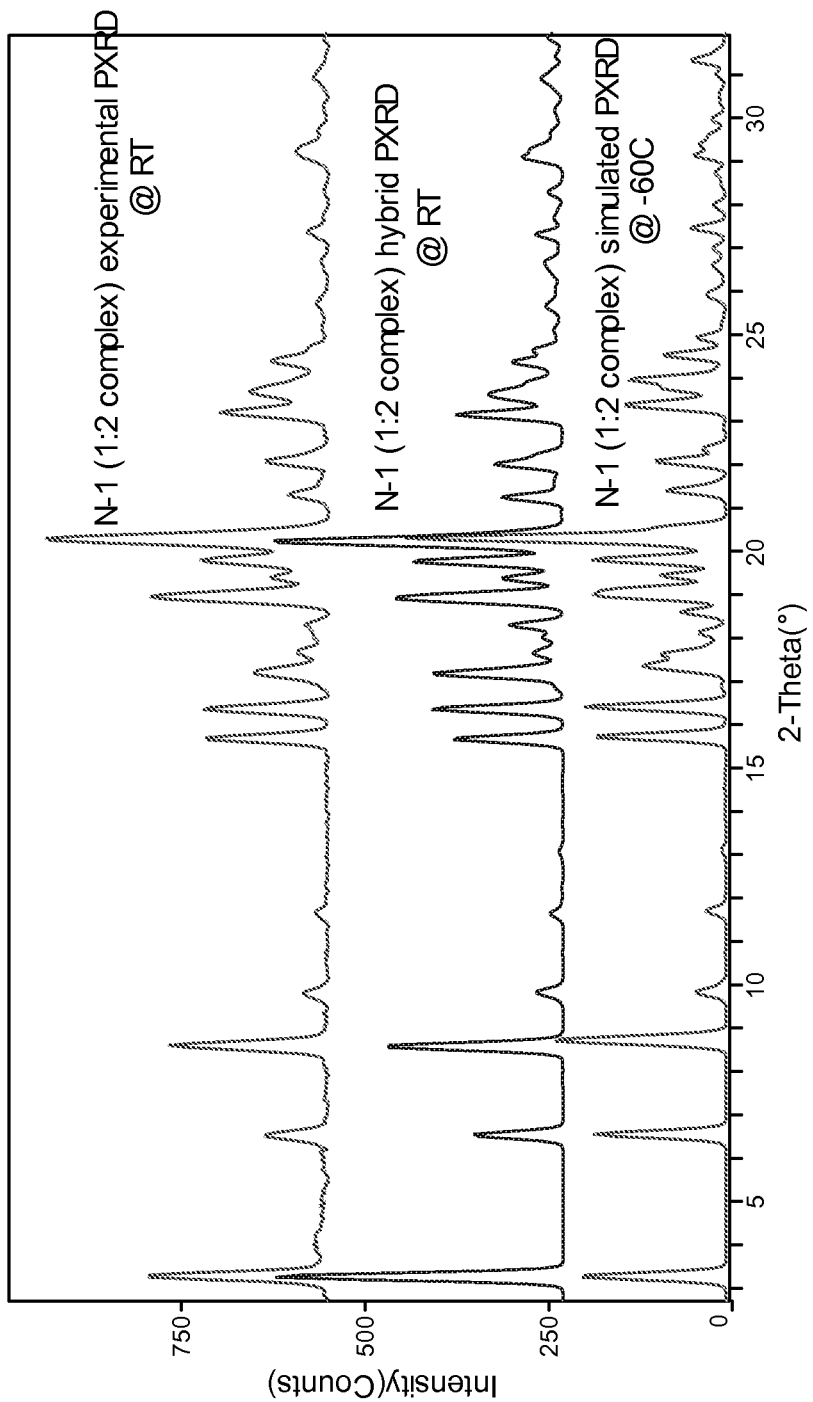
FIG. 13 shows calculated (simulated at −40° C.), hybrid (at room temperature) and observed (experimental at room temperature) powder X-ray diffraction patterns of the 1:2 L-proline complex crystalline structure Ih, form 3, N-1.
Figure 14:
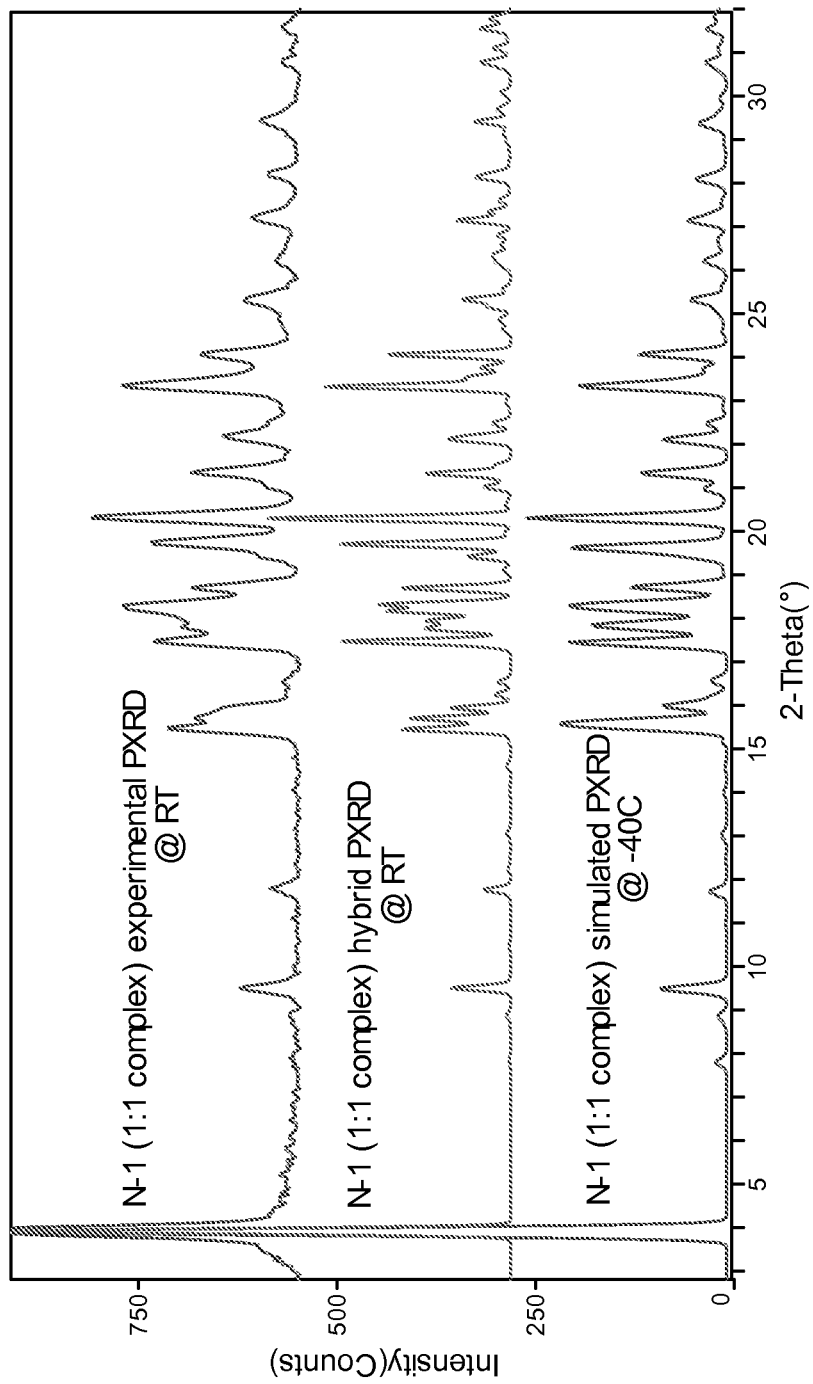
FIG. 14 shows calculated (simulated at −40° C.), hybrid (at room temperature) and observed (experimental at room temperature) powder X-ray diffraction pattern of the 1:1 L-proline complex crystalline structure Ii, form 6, N-1.
Figure 15:
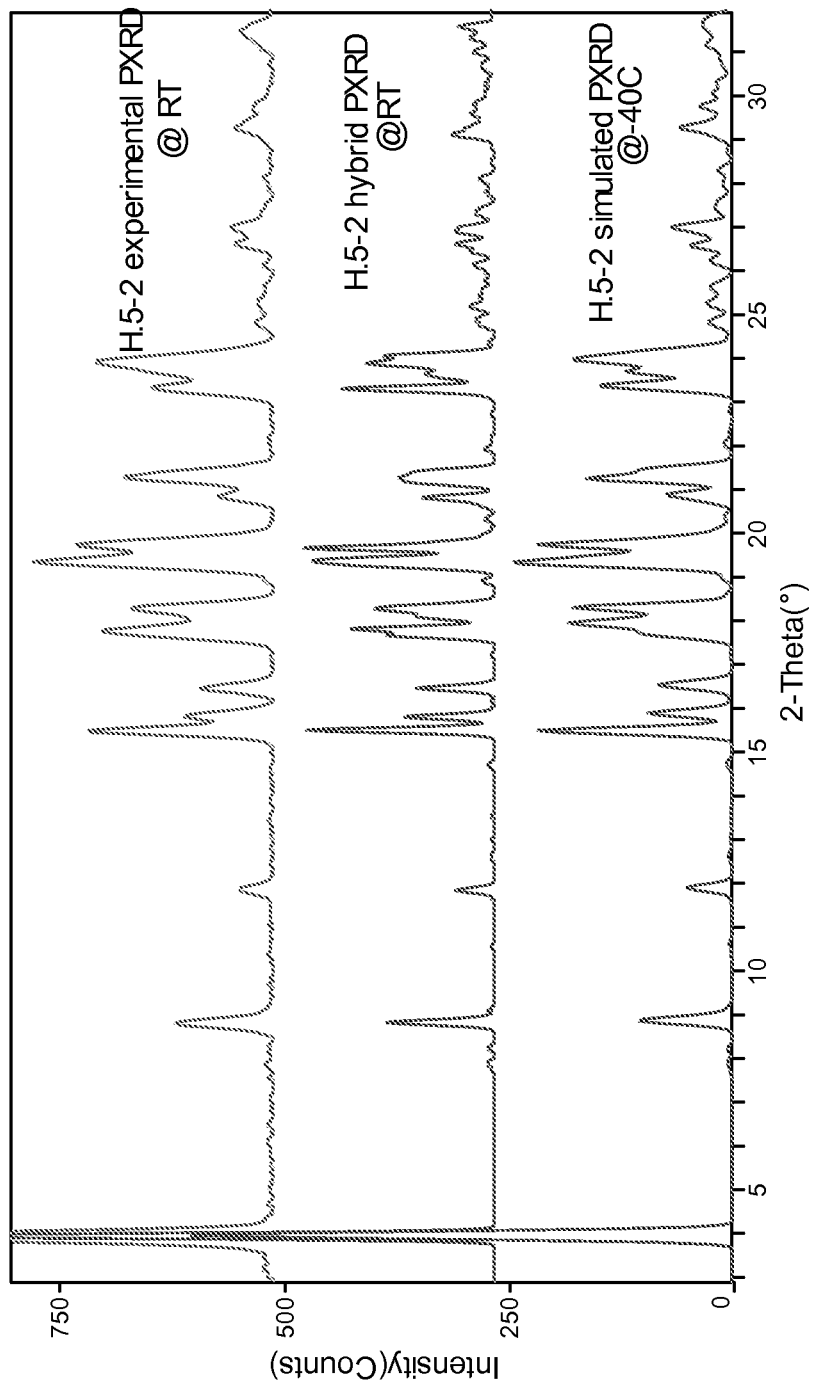
FIG. 15 shows calculated (simulated at −40° C.), hybrid (at room temperature) and observed (experimental at room temperature) powder X-ray diffraction pattern of the 1:1 L-proline hemihydrate crystalline structure Ij, form H.5-2.

Powder X-ray diffraction patterns for the (S)-PG (Ia), (R)-PG (Ib) structures are illustrated in FIGS. 1 and 2, respectively. Powder X-ray diffraction patterns for the 1,4-butyne-diol solvate If and the dimethanol solvate Ig are illustrated in FIGS. 9 and 10, respectively. Powder X-ray diffraction patterns for the 1:2 L-proline complex Ih, 1:1 L-proline complex Ii, and the 1:1 L-proline hemihydrate complex Ij structures are illustrated in FIGS. 13, 14 and 15, respectively. Selected diffraction peak positions (degrees 2θ±0.2) for the (S)-PG (Ia), (R)-PG (Ib) hemihydrate of 1:1 L-proline complex Ij (H.5-2), 1:2 L-proline complex Ih and 1:1 L-proline complex Ii structures are shown in Table 1 below. Characteristic diffraction peak positions (degrees 2θ±0.1) at RT, are based on a high quality pattern collected with a diffractometer (CuKα) with a spinning capillary with 2θ calibrated with a National Institute of Standards and Technology methodology, and other suitable standard known to those skilled in the art. The relative intensities, however, may change depending on the crystal size and morphology.

TABLE 1

Selected PXRD Peaks (2θ ± 0.2°)

| (S)-PG (Ia) | (R)-PG (Ib) | H.5-2, 1:1 L-proline (hemihydrate) (Ij) | N-1, 1:2 L-proline (Ih) | N-1 1:1 L-proline (Ii) |
|---|---|---|---|---|
| 3.8 | 3.9 | 3.9 | 3.3 | 3.9 |
| 7.6 | 8.0 | 8.8 | 6.5 | 9.5 |
| 8.1 | 8.7 | 15.5 | 8.6 | 15.4 |
| 8.7 | 15.3 | 15.8 | 15.7 | 15.7 |
| 15.2 | 15.6 | 16.5 | 16.4 | 15.9 |
| 15.7 | 17.2 | 17.8 | 17.2 | 17.5 |
| 17.1 | 19.2 | 19.4 | 18.9 | 18.7 |
| 18.9 | 19.9 | 19.7 | 19.8 | 19.7 |
| 20.1 | 20.3 | 20.8 | 20.2 | 20.3 |

Solid-State Nuclear Magnetic Resonance

The structures of (S)-PG (Ia), (R)-PG (Ib), 1,4-butynediol solvate If and dimethanol solvate Ig were characterized by solid state NMR techniques.

All solid-state C-13 NMR measurements were made with a Bruker DSX-400, 400 MHz NMR spectrometer. High resolution spectra were obtained using high-power proton decoupling and the TPPM pulse sequence and ramp amplitude cross-polarization (RAMP-CP) with magic-angle spinning (MAS) at approximately 12 kHz (A. E. Bennett et al, J. Chem. Phys., 1995, 103, 6951; G. Metz, X. Wu and S. O. Smith, J. Magn. Reson. A,. 1994, 110, 219-227). Approximately 70 mg of sample, packed into a canister-design zirconia rotor was used for each experiment. Chemical shifts (δ) were referenced to external adamantane with the high frequency resonance being set to 38.56 ppm (W. L. Earl and D. L. VanderHart, J. Magn. Reson., 1982, 48, 35-54).

Figure 3:
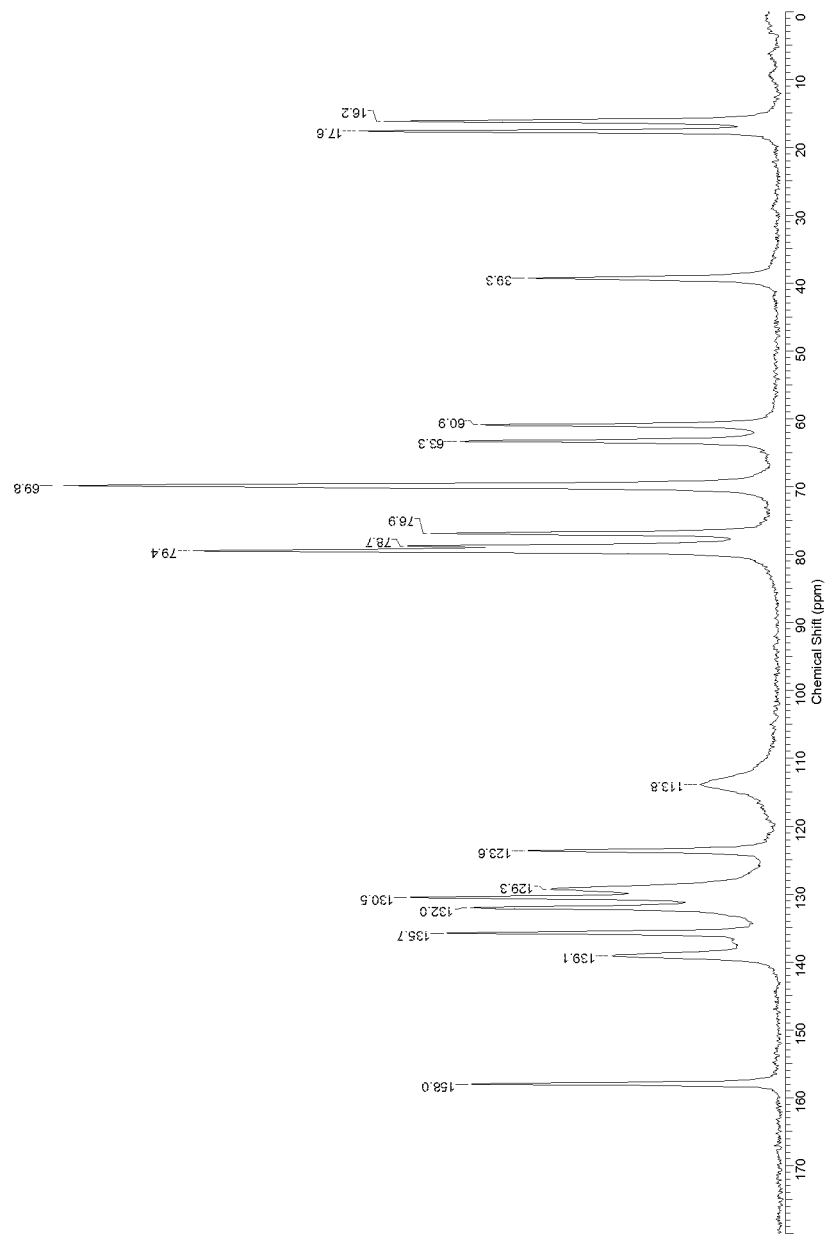
FIG. 3 shows $^{13}C$ NMR CPMAS spectrum for the (S)-PG crystalline structure Ia SC-3 form.
Figure 4:
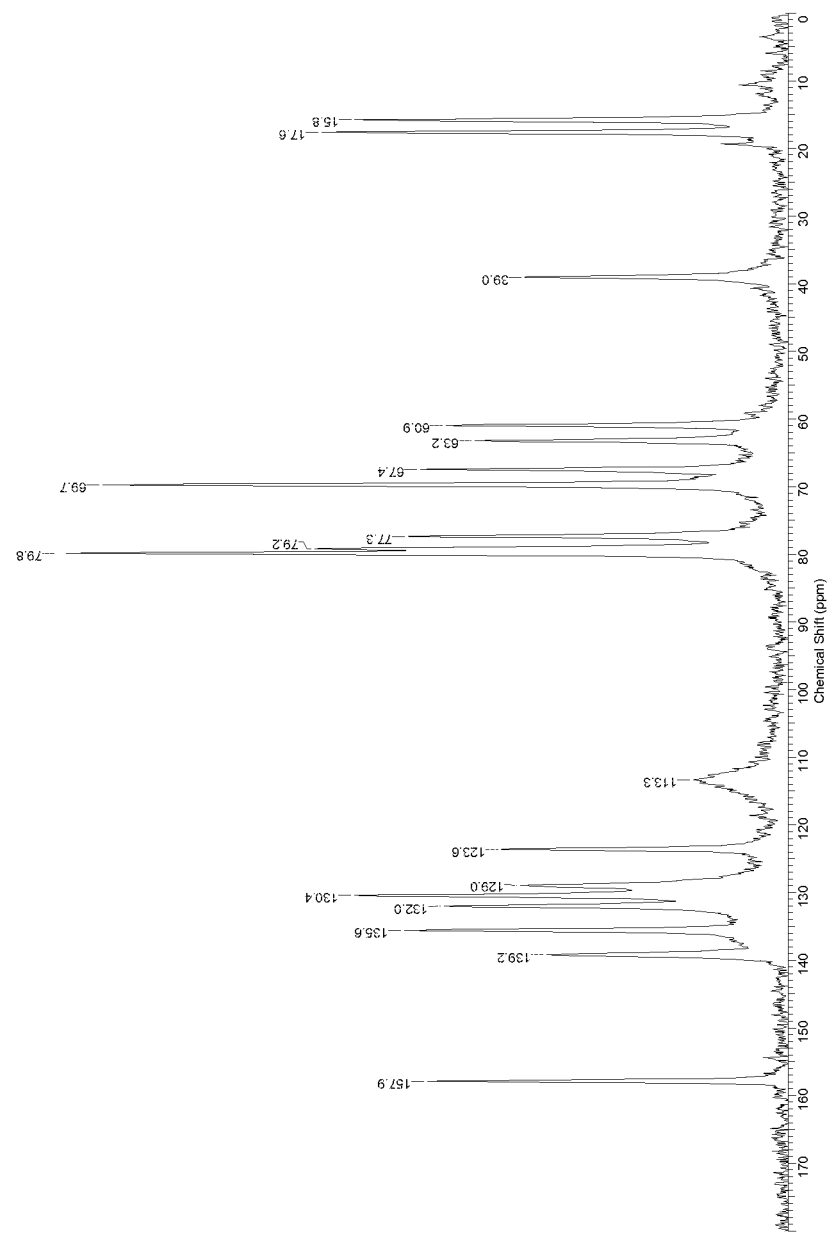
FIG. 4 shows $^{13}C$ NMR CPMAS spectrum for the (R)-PG crystalline structure of Ib.

The resulting $^{13}$C NMR CPMAS spectrum for structure (S)-PG and (R)-PG are shown in FIGS. 3 and 4 respectively.

The major resonance peaks for the solid state carbon spectrum of (S)-PG and (R)-PG are listed below in Table 1A and Table 2 and for 1,4-butyne-diol solvate If and dimethanol solvate Ig are listed below in Tables 2A and 2B, respectively. Crystal structures demonstrating substantially similar $^{13}$C NMR peak positions, wherein "substantially similar" means 10 to 15% of dimensionless value, are deemed to fall within the scope of the invention (i.e., equivalent to the structures illustrated below).

TABLE 1A

Proton NMR Peak Positions for (S)-Propylene Glycol Solvate Ia $^1$H NMR (400 MHz, d$_6$-DMSO) δ 1.00 (d, 3H, J = 6.25 Hz, PG-CH$_3$), 1.29 (t, 3H, J = 6.98 Hz, —CH$_2$CH$_3$), 3.0-3.30 (m, 4H, H2, H3, H4, H-5), 3.43 (m, 1H, H-6a), 3.53 (m, 1H), 3.69 (bdd, H, J = 4.4 Hz, H-6b), 3.9-4.1 (m, 5H, H-1, —CH$_2$, —CH$_2$), 4.38 (d, 1H, J = 4.5 Hz, OH), 4.44 (dt, 2H, J = 2.2 Hz, J = 5.7 Hz), 4.82 (d, 1H, J = 5.7 Hz, —OH), 4.94 and 4.95 (2d, 2H, 2-OH), 6.82 (d, 2H, J = 8.6 Hz, Ar—H), 7.09 (d, 2H, J = 8.6 Hz, Ar—H), 7.22 (dd, 1H, J = 1.97 Hz, 8.25 Hz, Ar—H), 7.31 (bd, 1H, 1.9 Hz, Ar—H), 7.36 (d, 1H, J = 8.2 Hz, Ar—H).

TABLE 2

SSNMR Peak Positions/δ (in ppm) Relative to TMS (Tetramethyl Silane)

| (S)-PG δ/ppm | (R)-PG δ/ppm |
|---|---|
| 16.2 | 15.8 |
| 17.6 | 17.6 |
| 39.3 | 39.0 |
| 60.9 | 60.9 |
| 63.3 | 63.2 |
| 69.8 | 67.4 |
| 76.9 | 69.7 |
| 78.7 | 77.3 |
| 79.4 | 79.2 |
| 113.8 | 79.8 |
| 123.6 | 113.3 |
| 129.3 | 123.6 |
| 130.5 | 129.0 |
| 132.0 | 130.4 |
| 135.7 | 132.0 |
| 139.1 | 135.6 |
| 158.0 | 139.2 |
|  | 157.9 |

These data are strictly valid for a 400 MHz spectrophotometer.

TABLE 2A

Proton NMR Peak Positions for 1,4-Butyne-diol Solvate If $^1$H NMR (400 MHz, CDCl$_3$) δ 1.33 (t, 3H, J = 7.1 Hz, —CH$_3$), 2.90 (s, 2H, —CH$_2$), 3.39 (s, 9H, —OCH$_3$), 3.4-3.65 (m, 3H), 3.81 (bm, 2H), 3.91 (q, 2H, J = 7.1 Hz, —CH$_2$), 3.97 (m, 1H), 6.73 (d, 1H, J = 8.6 Hz, Ar—H), 7.02 (d, 2H, J = 8.4 Hz, Ar—H), 7.25 (s, 2H, Ar—H), 7.34 (s, 1H, Ar—H); $^{13}$C (CDCl$_3$) δ 14.78, 38.43, 49.14, 50.57, 61.84, 63.34, 69.98, 72.53, 74.63, 100.95, 114.36, (2), 126.64, 129.19, 129.59, 129.71, 131.38, 134.30, 136.61, 138.50, 157.27. M.P. 103.08° C.

TABLE 2B

Proton NMR Peak Positions for Dimethanol Solvate Ig $^1$H NMR (400 MHz, DMSO-D6) δ 1.26 (t, 3H, J = 7.1 Hz, —CH$_3$), 2.38-2.54 (m, 1H), 2.5 (s, 2H, —CH$_2$), 3.2 (m, 1H), 3.35 (m, 3H, —OCH$_3$), 3.16-3.39 (m, 1H, H-6), 3.41-3.42 (m, 1H, H-6), 3.9 (q, 2H, J = 7.2 Hz, CH$_2$), 4.05 (d, 4H, —CH$_2$), 4.52 (t, 1H), 4.75 (m, 2H), 4.95 (d, 2H), 5.23 (t, 2H), 6.82 (d, 2H, J = 8.6 Hz, Ar—H), 7.07 (d, 2H, J = 8.6 Hz, Ar—H) 7.4 (s, 2H, Ar—H), 7.50 (s, 1H, Ar—H); $^{13}$C (CDCl$_3$) δ 14.69, 48.28, 49.02, 60.81, 62.84, 70.05, 74.02, 76.81, 83.97, 100.64, 114.23, 127.40, 128.2, 129.44, 131.2, 131.4, 132.45, 137.38, 138.57, 156.84. Elemental analysis Calculated for C$_{26}$H$_{33}$ClO$_9$: Calc C 59.48, H6.34, Cl 6.75; Found C 59.35, H5.97, Cl 6.19.

Thermal Gravimetric Analysis

Thermal gravimetric analysis (TGA) experiments were performed in a TA Instruments™ model Q500. The sample (about 10-30 mg) was placed in a platinum pan previously tared. The weight of the sample was measured accurately and recorded to a thousand of a milligram by the instrument The furnace was purged with nitrogen gas at 100 mL/min. Data were collected between room temperature and 300° C. at 10° C./min heating rate.

Figure 5:
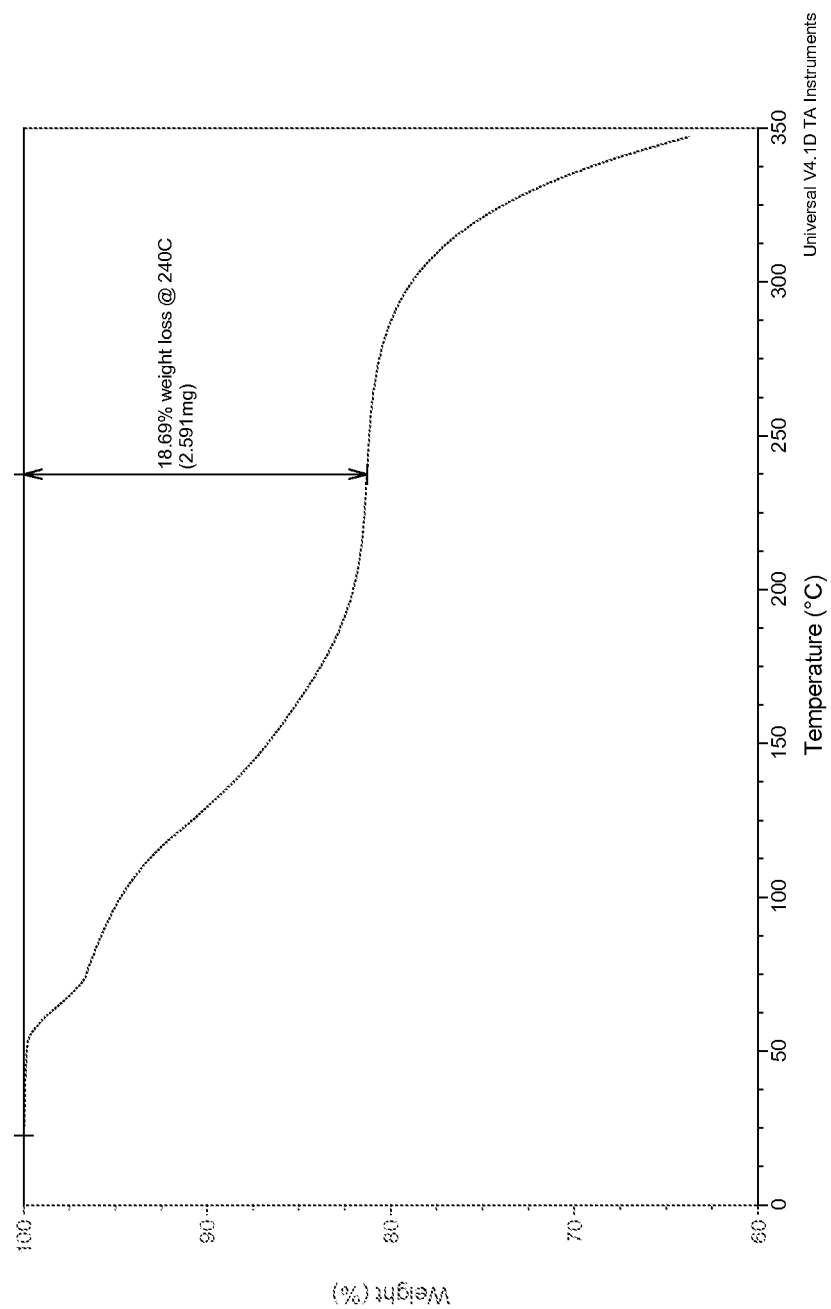
FIG. 5 shows a thermogravimetric analysis (TGA) curve of the (S)-PG crystalline structure of Ia, SC-3 form.
Figure 6:
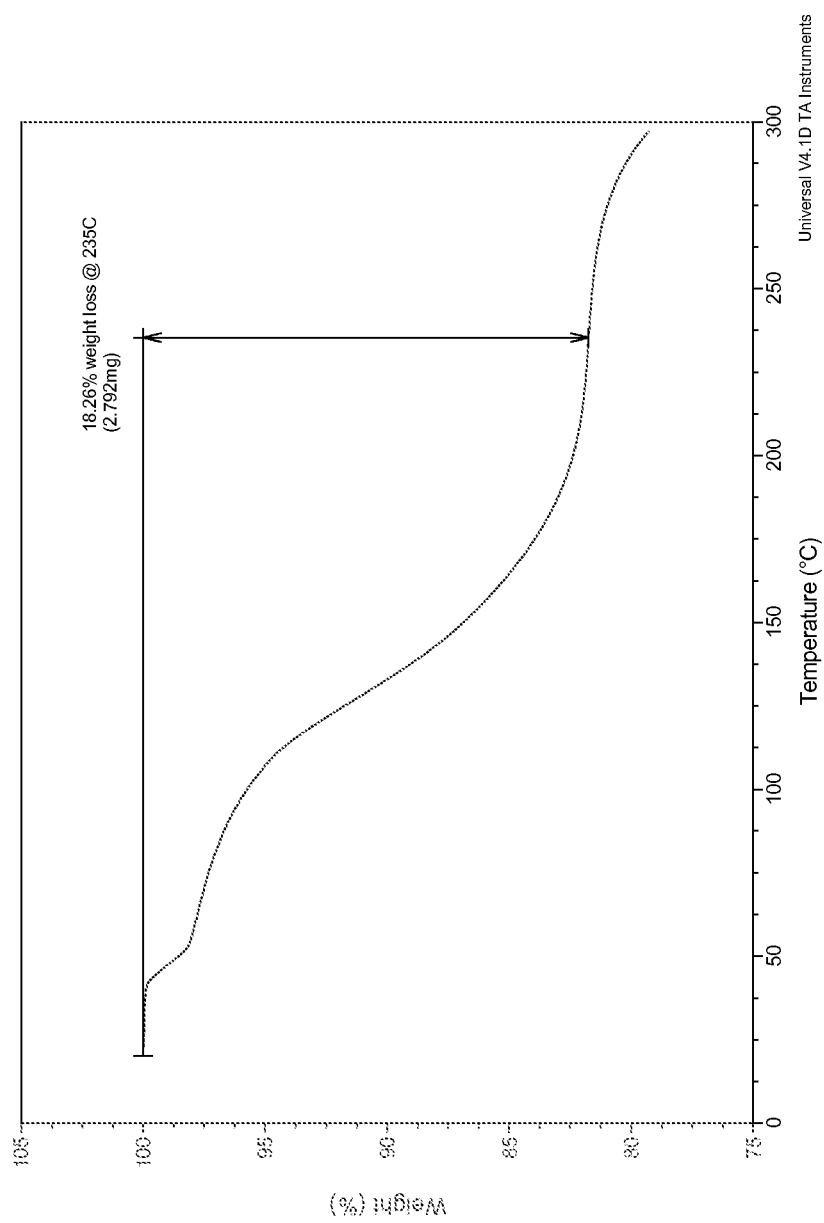
FIG. 6 shows a thermogravimetric analysis (TGA) curve of the (R)-PG crystalline structure of Ib, SD-3 form.

TGA curves for the (S)-PG Ia and (R)-PG Ib structures are shown in FIGS. 5 and 6, respectively. Weight loss corresponds to one mole of water and one mole of propylene glycol per mole of structure analyzed.

Figure 16:
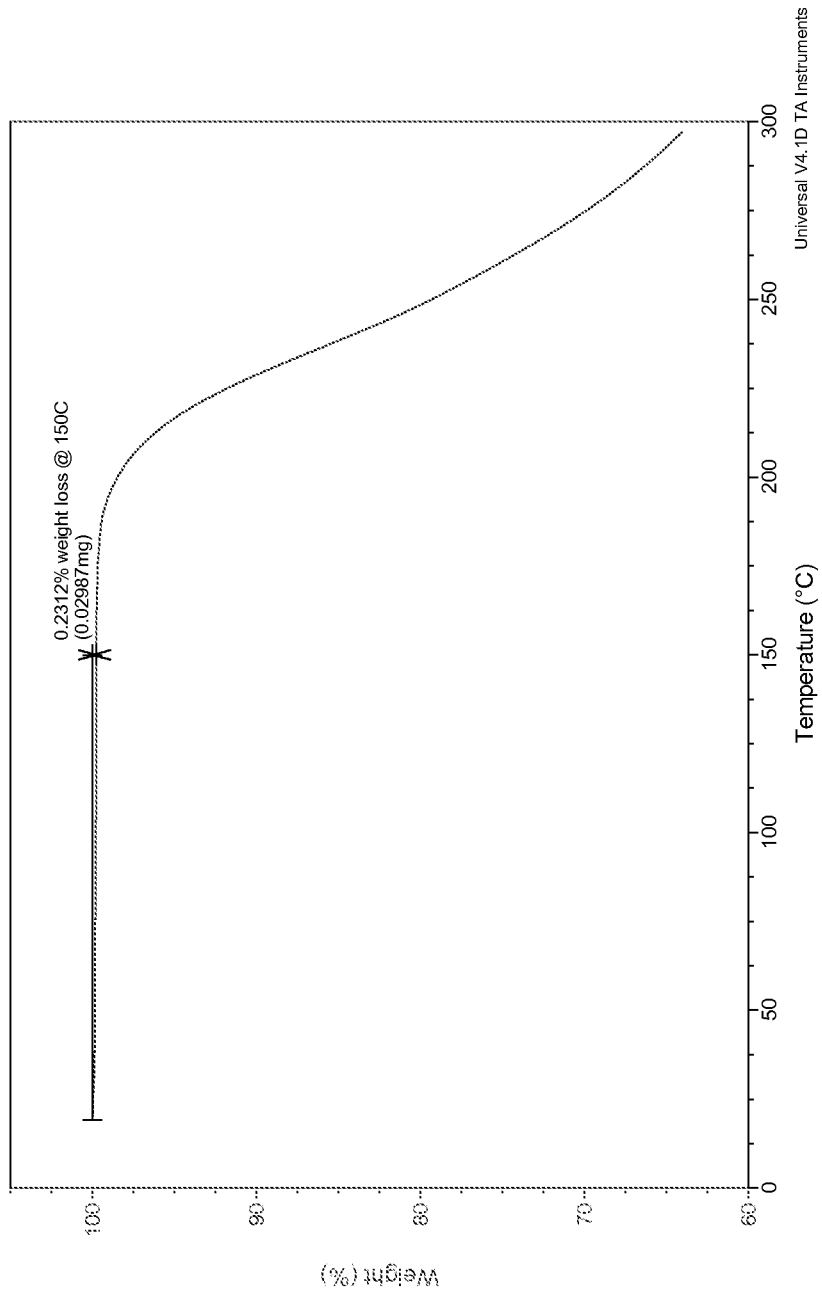
FIG. 16 shows a thermogravimetric analysis (TGA) curve of the 1:2 L-proline complex crystalline structure of Ih, form 3, N-1.
Figure 17:
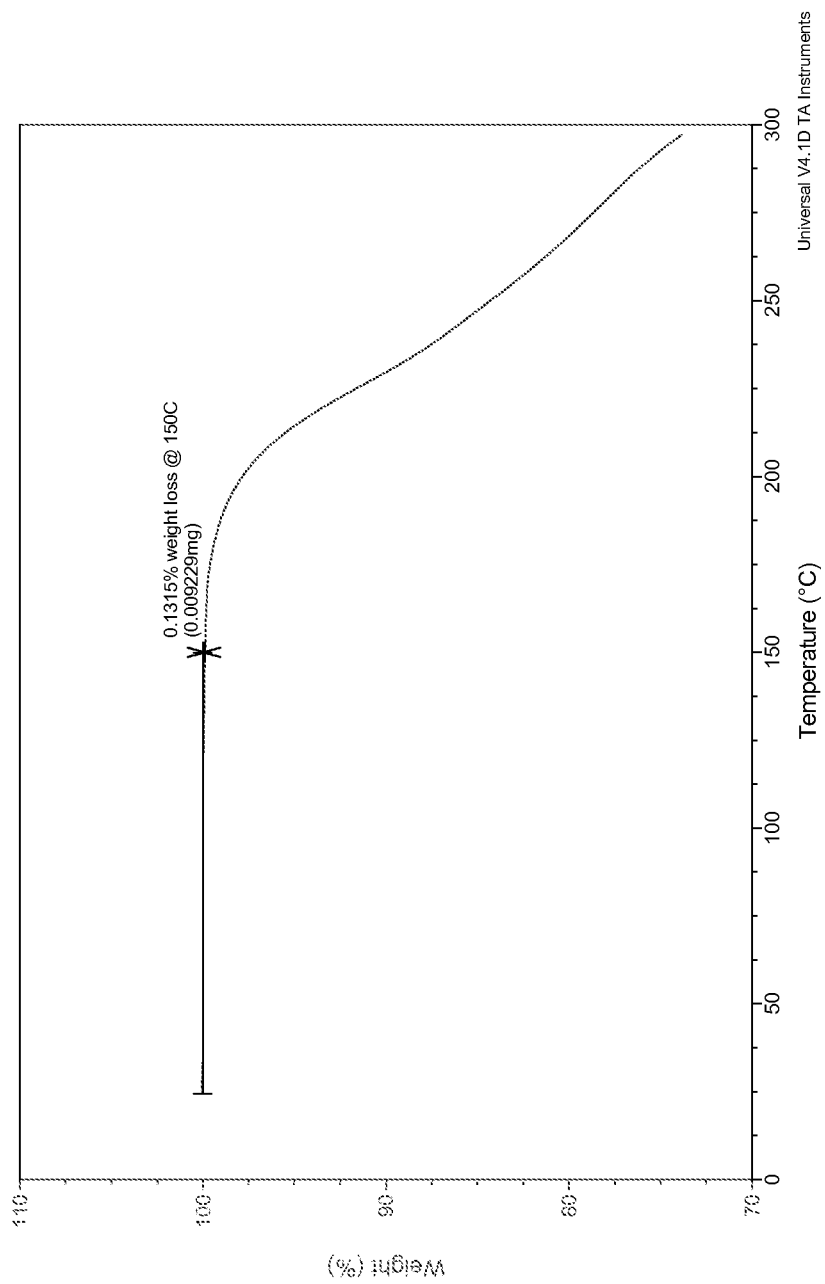
FIG. 17 shows a thermogravimetric analysis (TGA) curve of the 1:1 L-proline complex crystalline structure of Ii, form 6, N-1.
Figure 18:
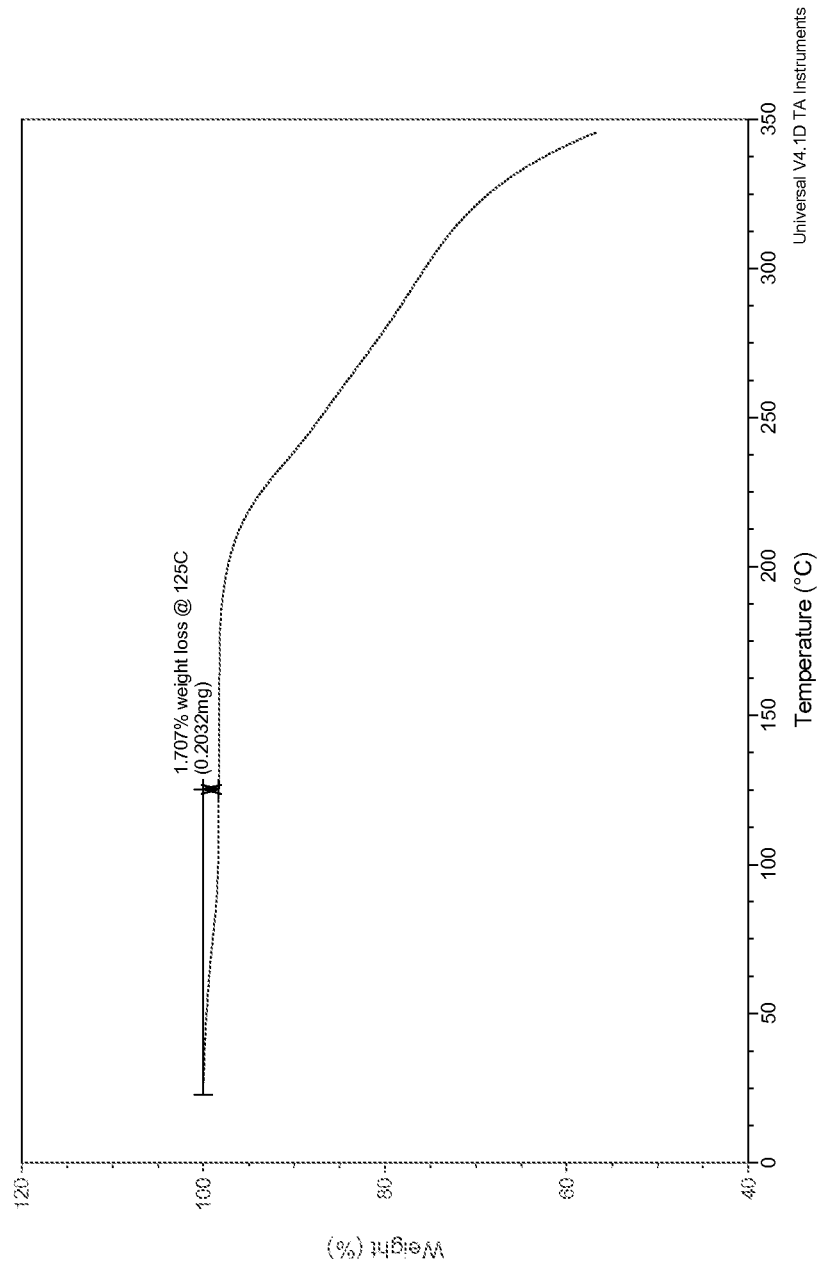
FIG. 18 shows a thermogravimetric analysis (TGA) curve of the 1:1 L-proline hemihydrate crystalline structure Ij, form H.5-2.

TGA curves for the 1:2 L-proline complex Ih, the 1:1 L-proline complex Ii and the 1:1 L-proline hemihydrate complex Ij structures are shown in FIGS. 16, 17 and 18, respectively. Weight loss corresponds to one mole of water and one mole of L-proline per mole of structure analyzed.

Differential Scanning Calorimetry

Figure 7:
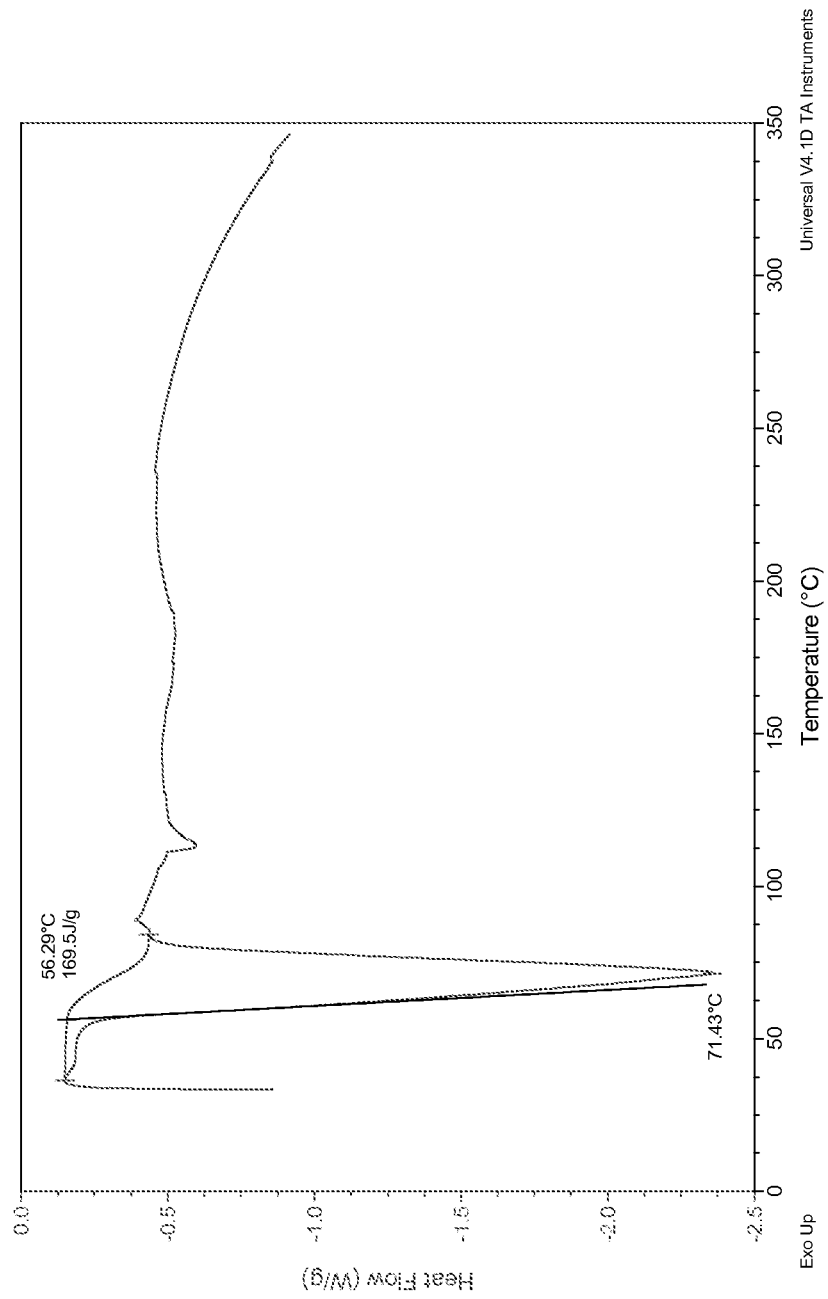
FIG. 7 shows a differential scanning calorimetry (DSC) thermogram of the (S)-PG crystalline structure of the compound of form Ia, SC-3 form.
Figure 8:
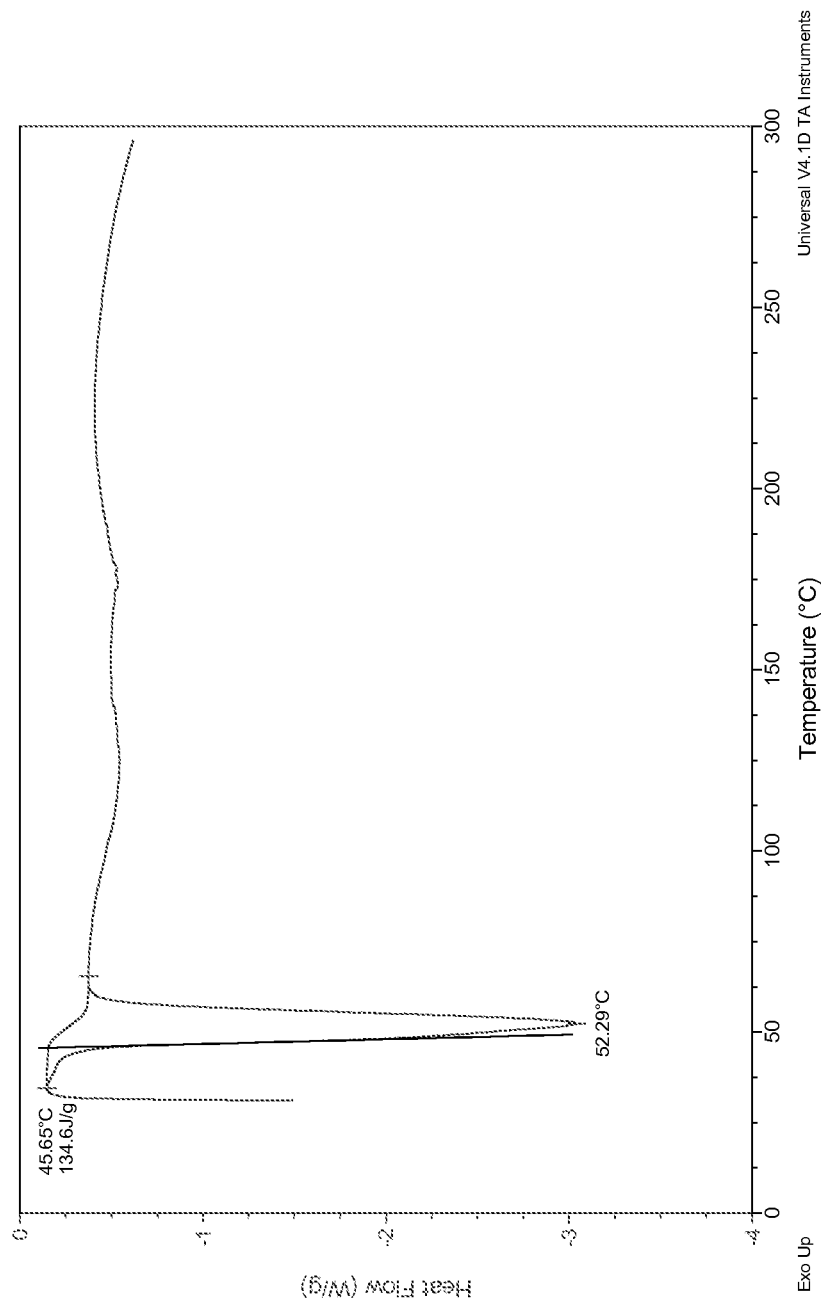
FIG. 8 shows a differential scanning calorimetry (DSC) thermogram of the (R)-PG crystalline structure of Ib.
Figure 11:
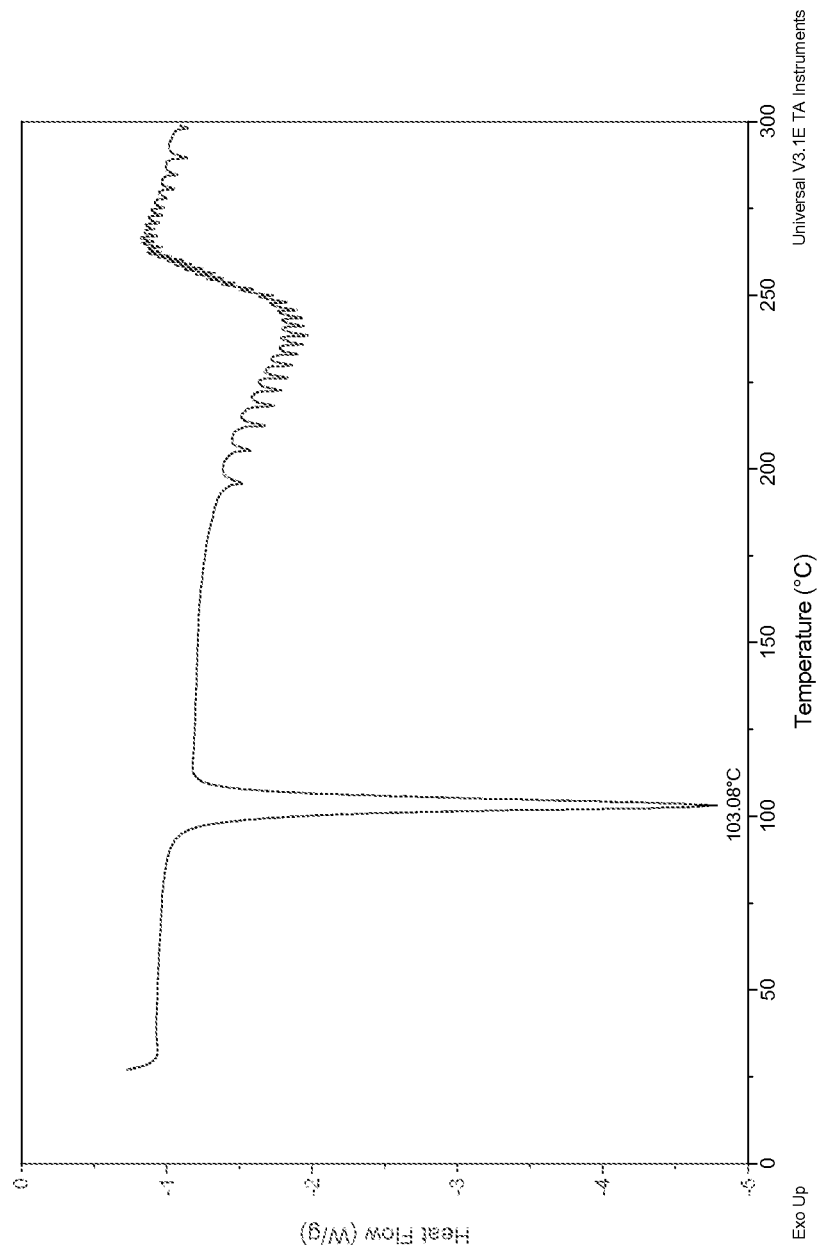
FIG. 11 shows a differential scanning calorimetry (DSC) thermogram of the 1,4-butyne-diol solvate crystalline structure If.
Figure 12:
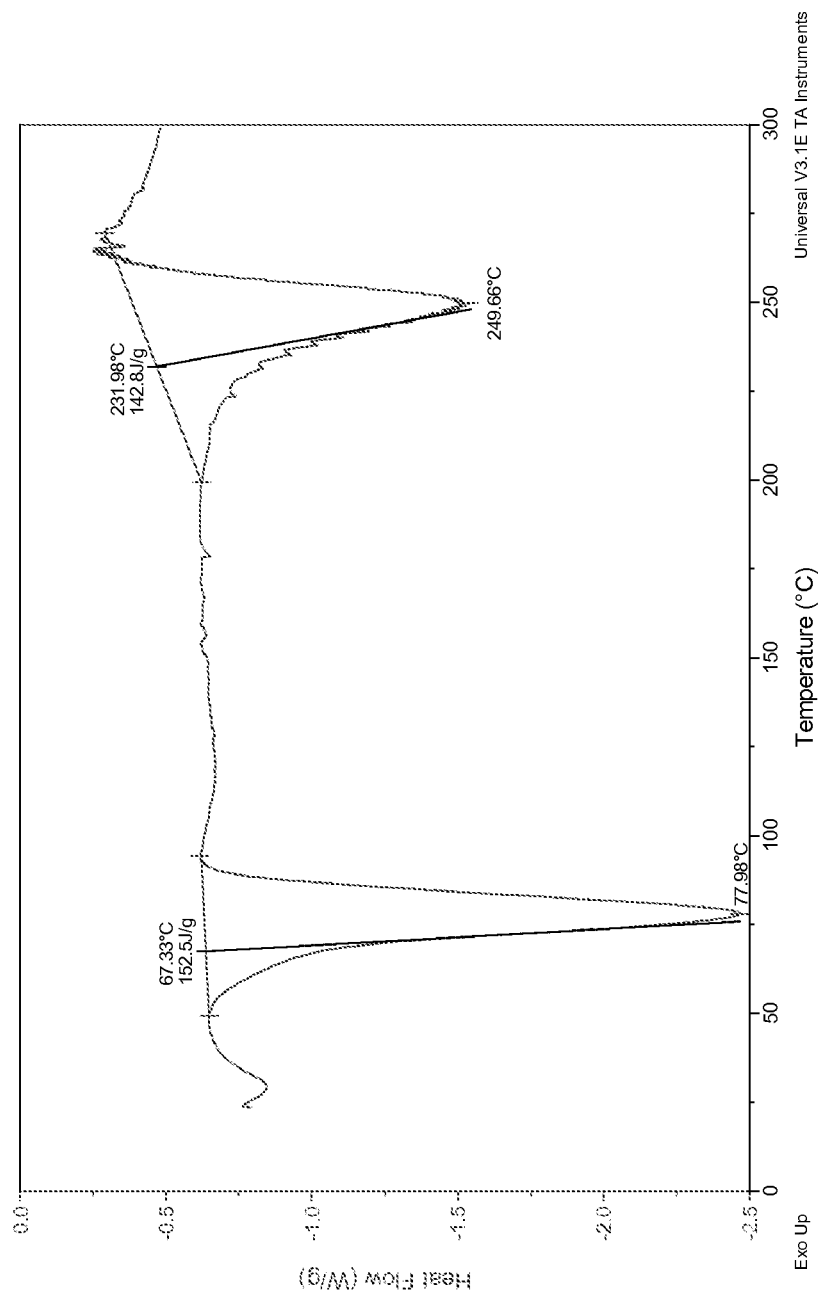
FIG. 12 shows a differential scanning calorimetry (DSC) thermogram of the dimethanol solvate crystalline structure of Ib.
Figure 19:
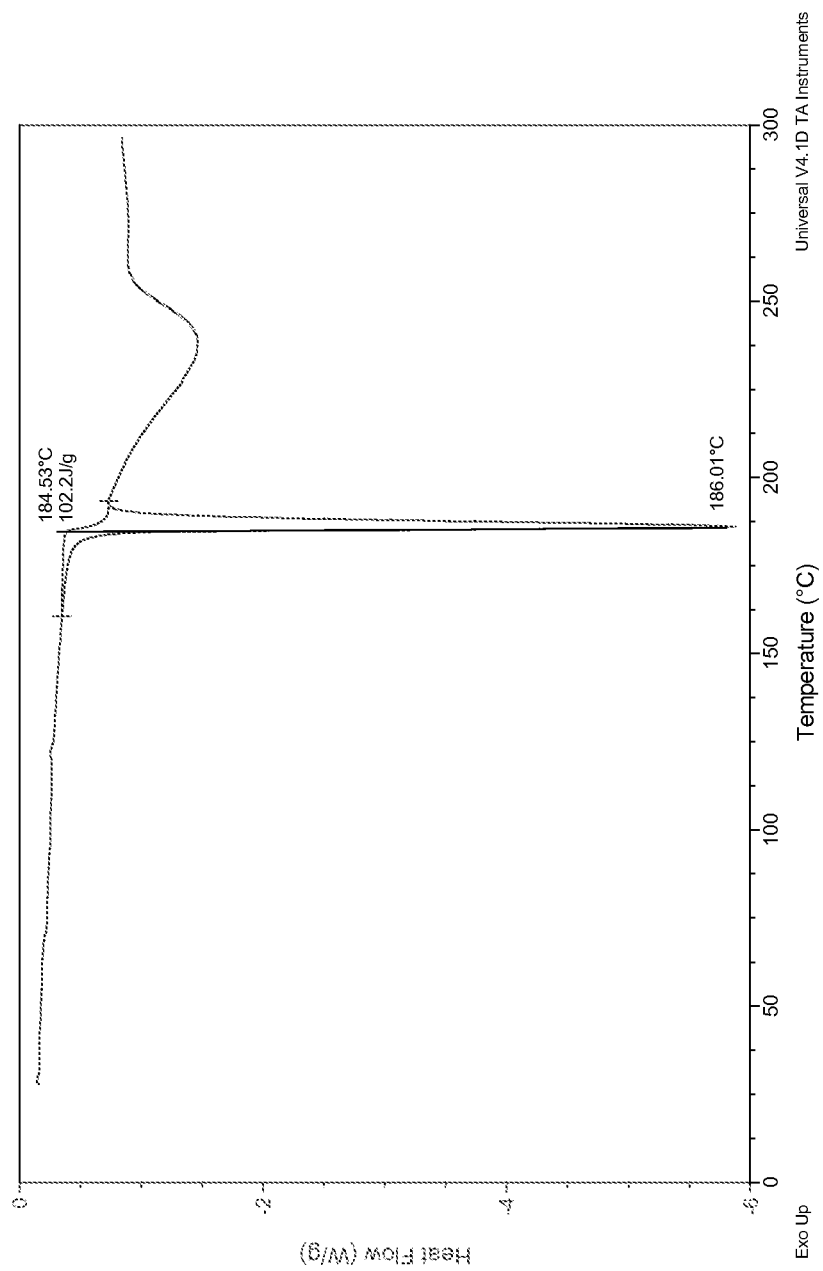
FIG. 19 shows a differential scanning calorimetry (DSC) thermogram of the 1:2 L-proline complex crystalline structure Ih, form 3, N-1.
Figure 20:
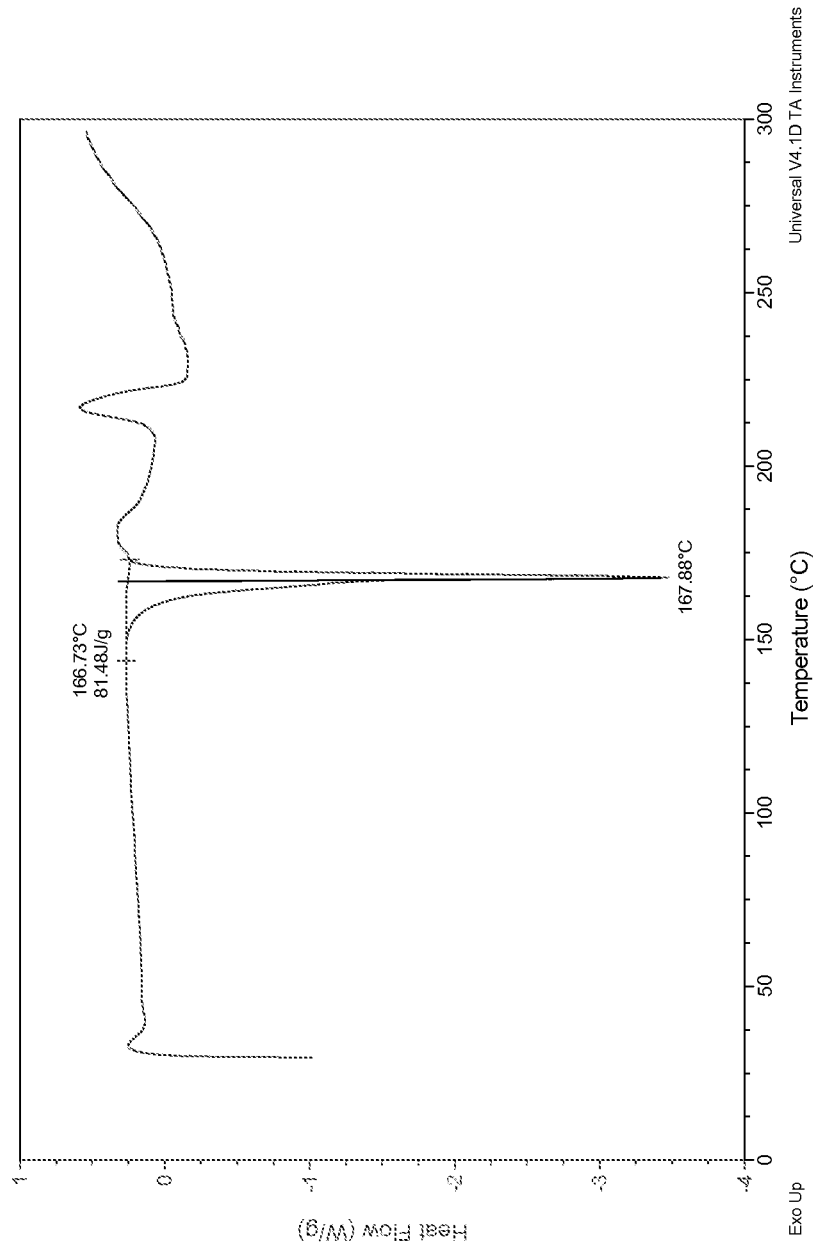
FIG. 20 shows a differential scanning calorimetry (DSC) thermogram of the 1:1 L-proline crystalline complex structure of Ii, form 6, N-1.
Figure 21:
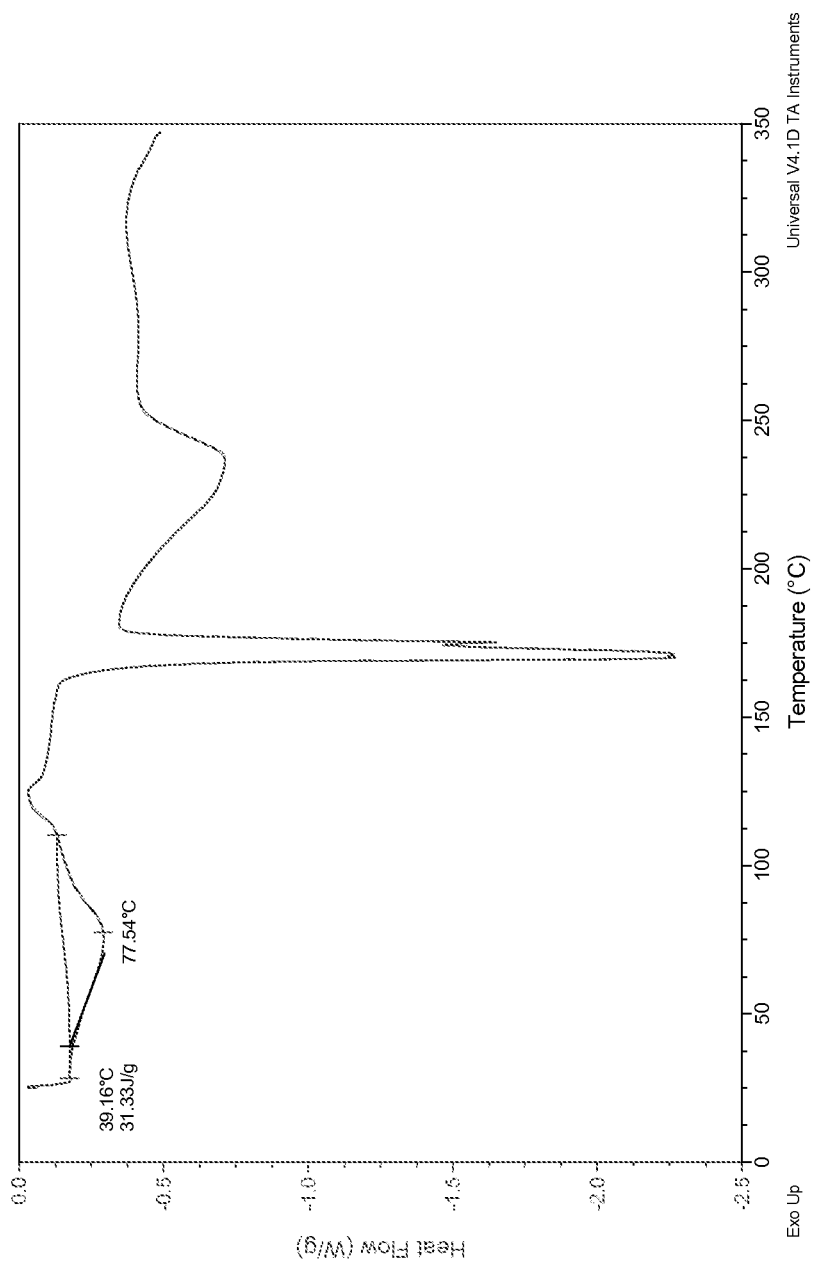
FIG. 21 shows a differential scanning calorimetry (DSC) thermogram of the 1:1 L-proline hemihydrate crystalline structure Ij, form H.5-2.

The solid state thermal behavior of the (S)-PG Ia, (R)-PG Ib, 1,4-butyne-diol solvate If, dimethanol solvate Ig, 1:2 L-proline Ih, the 1:1 L-proline Ii and the 1:1 L-proline hemihydrate Ij structures were investigated by differential scanning calorimetry (DSC). The DSC curves for the (S)-PG Ia and (R)-PG Ib structures are shown in FIGS. 7 and 8, respectively. The DSC curves for the 1,4-butyne-diol solvate If and the dimethanol solvate Ig structures are shown in FIGS. 11 and 12, respectively. The DSC curves for the 1:2 L-proline complex Ih, the 1:1 L-proline complex Ii and the 1:1 L-proline hemihydrate Ij structures are shown in FIGS. 19, 20 and 21, respectively.

Differential scanning calorimetry (DSC) experiments were performed in a TA Instruments™ model Q1000. The sample (about 2-6 mg) was weighed in an aluminum pan and recorded accurately recorded to a hundredth of a milligram, and transferred to the DSC. The instrument was purged with nitrogen gas at 50 mL/min. Data were collected between room temperature and 300° C. at 10° C./min heating rate. The plot was made with the endothermic peaks pointing down.

One of skill in the art will however, note that in DSC measurement there is a certain degree of variability in actual measured onset and peak temperatures, depending on rate of heating, crystal shape and purity, and other measurement parameters.

Single Crystal X-ray Analysis

A single crystal for the (S)-PG Ia, structure, and for the 1,4-butyne-diol solvate If, dimethanol solvate Ig, 1:2 L-proline Ih, 1:1 L-proline Ii and 1:1 L-proline hemihydrate Ij structures were obtained and investigated by x-ray diffraction.

Data were collected on a Bruker-Nonius[1] CAD4 serial diffractometer. Unit cell parameters were obtained through least-squares analysis of the experimental diffractometer settings of 25 high-angle reflections. Intensities were measured using Cu Kα radiation (λ=1.5418 Å) at a constant temperature with the ⊖-2⊖ variable scan technique and were corrected only for Lorentz-polarization factors. Background counts were collected at the extremes of the scan for half of the time of the scan. Alternately, single crystal data were collected on a Bruker-Nonius Kappa CCD 2000 system using Cu Kα radiation (λ=1.5418 Å). Indexing and processing of the measured intensity data were carried out with the HKL2000 software package[2] in the Collect program suite.[3]

When indicated, crystals were cooled in the cold stream of an Oxford cryo system[4] during data collection.

[4] Oxford Cryosystems Cryostream cooler: J. Cosier and A. M. Glazer, J. Appl. Cryst., 1986, 19, 105

The structures were solved by direct methods and refined on the basis of observed reflections using either the SDP[5] software package with minor local modifications or the crystallographic package, MAXUS.[6]

[5] SDP, Structure Determination Package, Enraf-Nonius, Bohemia N.Y. 11716 Scattering factors, including f' and f", in the SDP software were taken from the "International Tables for Crystallography", Kynoch Press, Birmingham, England, 1974; Vol. IV, Tables 2.2A and 2.3.1

[6] maXus solution and refinement software suite: S. Mackay, C. J. Gilmore, C. Edwards, M. Tremayne, N. Stewart, K. Shankland. maXus: a computer program for the solution and refinement of crystal structures from diffraction data.

The derived atomic parameters (coordinates and temperature factors) were refined through full matrix least-squares. The function minimized in the refinements was $\Sigma_w(|F_o|-|F_c|)^2$. R is defined as $\Sigma||F_o|-|F_c||/\Sigma|F_o|$ while $R_w=[\Sigma_w(|F_o|-|F_c|)^2/\Sigma_w|F_o|^2]^{1/2}$ where w is an appropriate weighting function based on errors in the observed intensities. Difference maps were examined at all stages of refinement. Hydrogens were introduced in idealized positions with isotropic temperature factors, but no hydrogen parameters were varied.

Unit cell parameters for the (S)-PG structure Ia form SC-3 are listed below in Table 3. As used herein, the unit cell parameter "molecules/per cell" refers to the number of molecules of Compound in the unit cell.

TABLE 3

Unit Cell Data for (S)-PG (Ia)

| Structure | T | a(Å) | b (Å) | c (Å) | α° | β° | γ° | $V_m$ | Z' | SG | Dcalc | R |
|---|---|---|---|---|---|---|---|---|---|---|---|---|
| Ia (S)-PG | 25 | 11.2688(8) | 4.8093(3) | 46.723(3) | 90 | 90 | 90 | 633 | 1 | P2₁2₁2₁ | 1.319 | .069 |

T = temp (° C.) for the crystallographic data.
Z' = number of drug molecules per asymmetric unit
$V_m$ = V(unit cell)/(Z drug molecules per cell)
R = residual index (I > 2sigma(I))
$D_{calc}$ = density of crystal calculated
SG = space group Table 4 below sets forth the positional parameters for the (S)-PG Ia structure at 25° C.

TABLE 4

Positional Parameters for (S)-PG at T = 25° C.

| Atom | X | Y | Z |
|---|---|---|---|
| CL | 0.7313 | 0.4674 | −0.2101 |
| O5 | 0.8119 | 0.5766 | −0.0701 |
| O4 | 0.7202 | 0.5458 | 0.0056 |
| O3 | 0.5115 | 0.3666 | −0.0246 |
| O6 | 0.9646 | 0.2671 | −0.0316 |
| O2 | 0.4895 | 0.5889 | −0.0811 |
| C2 | 0.6024 | 0.5045 | −0.0697 |
| C12 | 0.7946 | 0.4228 | −0.1261 |
| C5 | 0.8198 | 0.6301 | −0.0398 |
| O17 | 0.1633 | 0.2154 | −0.2179 |
| C8 | 0.6391 | 0.7665 | −0.1320 |
| C6 | 0.9425 | 0.5628 | −0.0299 |
| C3 | 0.5984 | 0.5441 | −0.0373 |
| C1 | 0.7059 | 0.6639 | −0.0829 |
| C7 | 0.7147 | 0.6097 | −0.1148 |
| C4 | 0.7190 | 0.4796 | −0.0240 |
| C10 | 0.7203 | 0.5412 | −0.1732 |
| C17 | 0.2586 | 0.3689 | −0.2079 |
| C19 | 0.4171 | 0.6835 | −0.2198 |
| C11 | 0.7959 | 0.3822 | −0.1562 |
| C9 | 0.6397 | 0.7259 | −0.1622 |
| C13 | 0.5535 | 0.8771 | −0.1822 |
| C14 | 0.4508 | 0.6852 | −0.1907 |
| C15 | 0.3841 | 0.5376 | −0.1712 |
| C16 | 0.2861 | 0.3765 | −0.1788 |
| C20 | 0.1012 | 0.0595 | −0.1979 |
| C18 | 0.3232 | 0.5239 | −0.2279 |
| C21 | 0.0030 | −0.0944 | −0.2137 |

TABLE 4-continued

Positional Parameters for (S)-PG at T = 25° C.

| Atom | X | Y | Z |
|---|---|---|---|
| O89 | 0.3708 | 0.0977 | −0.0854 |
| O88 | 0.1294 | 0.2019 | −0.0742 |
| C88 | 0.1652 | −0.0245 | −0.0920 |
| C89 | 0.2791 | 0.0335 | −0.1051 |
| C87 | 0.0645 | −0.1005 | −0.1124 |
| O99 | 0.2722 | 0.4482 | −0.0319 |
| H21 | 0.6171 | 0.2877 | −0.0753 |
| H121 | 0.8544 | 0.3092 | −0.1123 |
| H51 | 0.7993 | 0.8404 | −0.0347 |
| H81 | 0.5805 | 0.9176 | −0.1225 |
| H61 | 0.9563 | 0.6296 | −0.0070 |
| H62 | 1.0096 | 0.6774 | −0.0422 |
| H31 | 0.5776 | 0.7529 | −0.0321 |
| H11 | 0.6920 | 0.8863 | −0.0793 |
| H41 | 0.7271 | 0.2607 | −0.0265 |
| H191 | 0.4656 | 0.8069 | −0.2353 |
| H111 | 0.8552 | 0.2316 | −0.1658 |
| H131 | 0.5284 | 1.0619 | −0.1717 |
| H132 | 0.6093 | 0.9308 | −0.2010 |
| H151 | 0.4086 | 0.5437 | −0.1488 |
| H161 | 0.2335 | 0.2640 | −0.1632 |
| H201 | 0.1483 | −0.1065 | −0.1854 |
| H202 | 0.0535 | 0.1811 | −0.1804 |
| H181 | 0.2987 | 0.5193 | −0.2503 |
| H211 | −0.0606 | −0.2245 | −0.2014 |
| H212 | −0.0562 | 0.0572 | −0.2256 |
| H213 | 0.0387 | −0.2305 | −0.2306 |
| H2 | 0.4362 | 0.4237 | −0.0836 |
| H3 | 0.4297 | 0.4310 | −0.0299 |
| H4 | 0.7387 | 0.3750 | 0.0172 |
| H6 | 0.9827 | 0.1877 | −0.0122 |
| H881 | 0.1809 | −0.2154 | −0.0792 |
| H891 | 0.2662 | 0.2151 | −0.1200 |
| H892 | 0.3059 | −0.1396 | −0.1196 |
| H871 | 0.0875 | −0.2595 | −0.1270 |
| H872 | −0.0137 | −0.1453 | −0.1008 |
| H873 | 0.0462 | 0.0938 | −0.1255 |
| H89 | 0.4203 | −0.0719 | −0.0817 |
| H88 | 0.0653 | 0.1382 | −0.0608 |
| H991 | 0.2473 | 0.6301 | −0.0234 |
| H992 | 0.2108 | 0.3906 | −0.0463 |

Unit cell parameters for the mono-ethanol dihydrate (ethanol or EtOH structure) form SA-1, formula Ic are listed below in Table 5.

TABLE 5

Unit Cell Data for Ethanol SA-1 (Ic)

| Form | T° | a(Å) | b(Å) | c(Å) | α° | β° | γ° | Z' | SG | $V_m$ | R | $D_{calc}$ |
|---|---|---|---|---|---|---|---|---|---|---|---|---|
| Ic SA-1 | −50 | 11.519(1) | 4.799(1) | 22.648(1) | — | 94.58(1) | — | 1 | P2$_1$ | 624 | 1.307 | 0.05 |

T = temp (° C.) for crystallographic data
Z' = number of drug molecules per asymmetric unit
$V_m$ = V (unit cell)/(Z drug molecules per cell)
R = residual index (I > 3sigma(I))
$D_{calc}$ = density of crystal calculated
SG = space group Table 6 below sets forth the positional parameters for the form SA-1 (mono-ethanol-dihydrate), Ic at −50° C.

TABLE 6

Fractional Atomic Coordinates for Form SA-1 at T = −50° C.

| Atom | X | Y | Z |
|---|---|---|---|
| CL | 0.7673 | 0.0854 | −0.4142 |
| O2 | 0.8652 | 0.6413 | −0.1468 |
| O5 | 0.8652 | 0.6413 | −0.1468 |
| O6 | 1.0613 | 0.9910 | −0.0876 |
| C2 | 0.6634 | 0.5087 | −0.1420 |
| O3 | 0.5964 | 0.4528 | −0.0442 |
| C1 | 0.7531 | 0.6504 | −0.1782 |
| O17 | 0.1965 | −0.2110 | −0.3797 |
| O4 | 0.7928 | 0.7549 | 0.0061 |
| C7 | 0.7605 | 0.5175 | −0.2375 |
| C3 | 0.6679 | 0.6209 | −0.0790 |
| C14 | 0.4816 | 0.3213 | −0.3866 |
| C10 | 0.7629 | 0.2551 | −0.3461 |
| C13 | 0.5827 | 0.5268 | −0.3868 |
| C8 | 0.6801 | 0.5902 | −0.2843 |
| C9 | 0.6770 | 0.4593 | −0.3397 |
| C6 | 0.9968 | 0.7646 | −0.0652 |
| C12 | 0.8423 | 0.3089 | −0.2459 |
| C4 | 0.7906 | 0.6184 | −0.0498 |
| C5 | 0.8704 | 0.7698 | −0.0896 |
| C15 | 0.4335 | 0.2531 | −0.3337 |
| C11 | 0.8449 | 0.1815 | −0.3008 |
| C17 | 0.2911 | −0.0396 | −0.3851 |
| C20 | 0.141 | −0.3384 | −0.4319 |
| C19 | 0.4321 | 0.2052 | −0.4377 |
| C18 | 0.3377 | 0.0255 | −0.4384 |
| C16 | 0.3405 | 0.0751 | −0.3330 |
| C21 | 0.0431 | −0.5128 | −0.4132 |
| O98 | 0.3643 | 0.6071 | −0.0516 |
| O88 | 0.2324 | −0.2097 | −0.1501 |
| C89 | 0.1155 | −0.3014 | −0.2376 |
| C88 | 0.2065 | −0.4150 | −0.1969 |
| O99 | 0.4409 | 0.0604 | −0.1784 |
| H21 | 0.6816 | 0.2833 | −0.1387 |
| H11 | 0.7283 | 0.8620 | −01.864 |
| H31 | 0.6356 | 0.8307 | −0.0805 |
| H131 | 0.6184 | 0.5131 | −0.4303 |
| H132 | 0.5505 | 0.7308 | −0.3806 |
| H81 | 0.6182 | 0.7524 | −0.2770 |
| H61 | 1.0365 | 0.5668 | −0.0787 |
| H62 | 1.0037 | 0.7711 | −0.0175 |
| H121 | 0.9040 | 0.2455 | −0.2092 |
| H41 | 0.8196 | 0.4009 | −0.0436 |
| H51 | 0.8385 | 0.9826 | −0.0936 |
| H151 | 0.4692 | 0.3444 | −0.2915 |
| H111 | 0.9111 | 0.0214 | −0.3081 |
| H201 | 0.1146 | −0.1875 | −0.4650 |
| H202 | 0.2075 | −0.4764 | −0.4514 |
| H191 | 0.4703 | 0.2491 | −0.4794 |
| H181 | 0.3000 | −0.0606 | −0.4802 |
| H161 | 0.3071 | 0.0128 | −0.2910 |
| H3 | 0.5153 | 0.5297 | −0.0473 |
| H2 | 0.5091 | 0.3623 | −0.1752 |

TABLE 6-continued

Fractional Atomic Coordinates for Form SA-1 at T = −50° C.

| Atom | X | Y | Z |
|---|---|---|---|
| H211 | −0.0028 | −0.6153 | −0.4507 |
| H212 | 0.0724 | −0.6675 | −0.3807 |
| H213 | −0.0204 | −0.3772 | −0.3928 |
| H6 | 1.1241 | 0.9168 | −0.1118 |
| H4 | 0.8466 | 0.6527 | 0.0359 |
| H981 | 0.3836 | 0.7445 | −0.0185 |
| H982 | 0.3063 | 0.4696 | −0.0382 |
| H891 | 0.0626 | −0.4601 | −0.2593 |
| H892 | 0.0592 | −0.1642 | −0.2133 |
| H893 | 0.1534 | −0.1727 | −0.2709 |
| H881 | 0.2834 | −0.4603 | −0.2200 |
| H882 | 0.1765 | −0.6100 | −0.1783 |
| H88 | 0.2806 | −0.2965 | −0.1158 |
| H991 | 0.3630 | −0.0141 | −0.1685 |
| H992 | 0.4889 | −0.1137 | −0.1762 |

Unit cell parameters for the ethylene glycol form SB-1, formula Id are listed below in Table 7.

TABLE 7

Unit Cell Data for EG-SB-1 (Id)

| Form | T° | a(Å) | b(Å) | c(Å) | α° | β° | γ° | Z' | SG | $V_m$ | R | $D_{calc}$ |
|---|---|---|---|---|---|---|---|---|---|---|---|---|
| Id SB-1 | −50 | 11.593(8) | 4.766(5) | 22.78(3) | — | 93.38(9) | — | 1 | $P2_1$ | 628 | .19 | 1.340 |

T = temp (° C.) for crystallographic data
Z' = number of drug molecules per asymmetric unit
$V_m$ = V (unit cell)/(Z drug molecules per cell)
R = residual index (I > 3sigma(I))
$D_{calc}$ = density of crystal calculated
SG = space group Table 8 below sets forth the positional parameters for the form SB-1 (ethylene glycol) Id at −50° C.

TABLE 8

Fractional Atomic Coordinates for Form SB-1 at T = −50° C.

| Atom | X | Y | Z |
|---|---|---|---|
| CL | 0.7590 | 0.0820 | −0.4198 |
| O5 | 0.8631 | 0.5990 | −0.1537 |
| O17 | 0.1901 | −0.1911 | −0.3791 |
| C13 | 0.5791 | 0.5319 | −03885 |
| O3 | 0.5941 | 0.4849 | −0.0439 |
| C11 | 0.8381 | 0.1410 | −0.3059 |
| O4 | 0.7851 | 0.8250 | −0.0026 |
| C10 | 0.7531 | 0.2610 | −0.3514 |
| O2 | 0.5470 | 0.4971 | −0.1739 |
| C18 | 0.3341 | 0.0390 | −0.4399 |
| C14 | 0.4851 | 0.3559 | −0.3849 |
| C1 | 0.7451 | 0.6551 | −0.1789 |
| C12 | 0.8281 | 0.2849 | −0.2539 |
| C5 | 0.8711 | 0.7820 | −0.0959 |
| C19 | 0.4311 | 0.2230 | −0.4349 |
| C17 | 0.2810 | −0.0380 | −0.3919 |
| C4 | 0.7791 | 0.6341 | −0.0569 |
| C7 | 0.7530 | 0.4769 | −0.2399 |
| C8 | 0.6751 | 0.5781 | −0.2889 |
| C9 | 0.6671 | 0.4150 | −0.3429 |
| C2 | 0.6601 | 0.4859 | −0.1429 |
| C15 | 0.4250 | 0.2791 | −0.3379 |
| C20 | 0.1391 | −0.3181 | −0.4309 |
| C21 | 0.0331 | −0.4761 | −0.4109 |
| C3 | 0.6660 | 0.6460 | −0.0839 |
| C16 | 0.3341 | 0.1049 | −0.3399 |
| O6 | 1.0280 | 0.4331 | −0.0685 |
| O98 | 0.3689 | 0.6530 | −0.0551 |
| O99 | 0.4310 | 0.0080 | −0.1639 |
| C6 | 0.9880 | 0.6960 | −0.0759 |

TABLE 8-continued

Fractional Atomic Coordinates for Form SB-1 at T = −50° C.

| Atom | X | Y | Z |
|---|---|---|---|
| O88 | 0.1661 | −0.7610 | −0.1669 |
| O89 | 0.0461 | −0.2291 | −0.2249 |
| C88 | 0.1970 | −0.5606 | −0.1946 |
| C89 | 0.1423 | −0.4698 | −0.2450 |
| H89 | −0.0093 | −0.1368 | −0.2011 |
| H88 | 0.0999 | −0.9161 | −0.1930 |
| H2 | 0.5081 | 0.3212 | −0.1695 |
| H3 | 0.5158 | 0.5512 | −0.0479 |
| H6 | 1.0592 | 0.3693 | −0.1043 |
| H981 | 0.3142 | 0.5218 | −0.0410 |
| H982 | 0.3908 | 0.7860 | −0.0248 |
| H991 | 0.4708 | −0.1672 | −0.1673 |
| H992 | 0.3887 | 0.0065 | −0.1290 |
| H41 | 0.8040 | 0.4214 | −0.0458 |
| H31 | 0.6366 | 0.8606 | −0.0878 |
| H51 | 0.8478 | 0.9977 | −0.1052 |
| H21 | 0.6886 | 0.2707 | −0.1389 |
| H11 | 0.7300 | 0.8758 | −0.1869 |

TABLE 8-continued

Fractional Atomic Coordinates for Form SB-1 at T = −50° C.

| Atom | X | Y | Z |
|---|---|---|---|
| H61 | 1.0435 | 0.7903 | −0.1069 |
| H62 | 1.0031 | 0.7943 | −0.0335 |
| H81 | 0.6253 | 0.7679 | −0.2848 |
| H111 | 0.8971 | −0.0296 | −0.3127 |
| H121 | 0.8920 | 0.2316 | −0.2193 |
| H151 | 0.4529 | 0.3653 | −0.2956 |
| H161 | 0.2954 | 0.0652 | −0.2987 |
| H181 | 0.3033 | −0.0383 | −0.4826 |
| H191 | 0.4696 | 0.2685 | −0.4759 |
| H201 | 0.1135 | −0.1601 | −0.4631 |
| H202 | 0.1990 | −0.4618 | −0.4495 |
| H211 | −0.0104 | −0.5787 | −0.4482 |
| H212 | 0.0603 | −0.6313 | −0.3784 |
| H213 | −0.0253 | −0.3295 | −0.3920 |
| H891 | 0.0986 | −0.6418 | −0.2678 |
| H892 | 0.2033 | −0.3761 | −0.2733 |
| H881 | 0.2163 | −0.3858 | −0.1655 |
| H882 | 0.2762 | −0.6665 | −0.2039 |
| H131 | 0.6119 | 0.5248 | −0.4319 |
| H132 | 0.5566 | 0.7453 | −0.3781 |

Unit cell parameters for the ethylene glycol form SB-2, formula Ie are listed below in Table 9.

TABLE 9

Unit Cell Data for EG-SB-2 (Ie)

| Form | T° | a(Å) | b(Å) | c(Å) | α° | β° | γ° | Z' | SG | $V_m$ | R | $D_{calc}$ |
|---|---|---|---|---|---|---|---|---|---|---|---|---|
| Ie SB-2 | −50 | 11.4950(1) | 4.7443(1) | 44.4154(5) | — | — | — | 1 | $P2_12_12_1$ | 606 | .050 | 1.390 |

T = temp (° C.) for crystallographic data
Z' = number of drug molecules per asymmetric unit
$V_m$ = V (unit cell)/(Z drug molecules per cell)
R = residual index (I > 3sigma(I))
$D_{calc}$ = density of crystal calculated
SG = space group Table 10 below sets forth the positional parameters for the form SB-2 (ethylene glycol) Id at −50° C.

TABLE 10

Fractional Atomic Coordinates for Form SB-2 at T = −50° C.

| Atom | X | Y | Z |
|---|---|---|---|
| CL | 0.7374 | 0.5149 | −0.2111 |
| O1 | 0.8133 | 0.9822 | −0.0746 |
| O2 | 0.5013 | 0.9285 | −0.0845 |
| O4 | 0.7289 | 1.0601 | 0.0035 |
| O3 | 0.5256 | 0.8247 | −0.0225 |
| C13 | 0.5550 | 0.9627 | −0.1935 |
| O6 | 0.9728 | 0.7735 | −0.0353 |
| C4 | 0.7265 | 0.9455 | −0.0262 |
| C3 | 0.6074 | 0.9836 | −0.0396 |
| C8 | 0.6428 | 0.9915 | −0.1422 |
| C5 | 0.8145 | 1.0938 | −0.0449 |
| C2 | 0.6104 | 0.8706 | −0.0710 |
| C1 | 0.7042 | 1.0158 | −0.0896 |
| O17 | 0.1616 | 0.2406 | −0.1894 |
| C10 | 0.7254 | 0.6663 | −0.1761 |
| C14 | 0.4505 | 0.7632 | 0.1926 |
| C12 | 0.7921 | 0.6786 | −0.1254 |
| C7 | 0.7155 | 0.8961 | −0.1199 |
| C17 | 0.2595 | 0.4115 | −0.1926 |
| C9 | 0.6431 | 0.8746 | −0.1706 |
| C11 | 0.7977 | 0.5663 | −0.1538 |
| C18 | 0.3043 | 0.4904 | −0.2191 |
| C6 | 0.9384 | 1.0646 | −0.0348 |
| C21 | 0.0106 | −0.0544 | −0.2044 |
| C15 | 0.4002 | 0.6700 | −0.1674 |
| C16 | 0.3062 | 0.5028 | −0.1664 |
| C19 | 0.4048 | 0.6705 | −0.2196 |
| C20 | 0.1094 | 0.1211 | −0.2133 |
| O89 | 0.1914 | 0.1344 | −0.0851 |
| O88 | 0.0643 | −0.3997 | −0.0870 |
| C88 | 0.0717 | −0.2076 | −0.1097 |
| C89 | 0.1793 | −0.0404 | −0.1104 |
| O98 | 0.2861 | −0.0622 | −0.0315 |
| O99 | 0.3991 | 0.4406 | −0.0899 |

TABLE 10-continued

Fractional Atomic Coordinates for Form SB-2 at T = −50° C.

| Atom | X | Y | Z |
|---|---|---|---|
| H131 | 0.5987 | 0.9339 | −0.2163 |
| H132 | 0.5342 | 1.1796 | −0.1916 |
| H41 | 0.7470 | 0.7230 | −0.0250 |
| H31 | 0.5865 | 1.2077 | −0.0378 |
| H81 | 0.5800 | 1.1634 | −0.1366 |
| H51 | 0.7979 | 1.3174 | −0.0455 |
| H21 | 0.6251 | 0.6488 | −0.0697 |
| H11 | 0.6844 | 1.2377 | −0.0920 |
| H121 | 0.8481 | 0.5958 | −0.1080 |
| H111 | 0.8591 | 0.3889 | −0.1576 |
| H181 | 0.2593 | 0.4179 | −0.2399 |
| H151 | 0.4420 | 0.7303 | −0.1453 |
| H161 | 0.2700 | 0.4433 | −0.1446 |
| H191 | 0.4500 | 0.7270 | −0.2410 |
| H61 | 0.9486 | 1.1532 | −0.0124 |
| H62 | 0.9940 | 1.1868 | −0.0502 |
| H201 | 0.0802 | 0.2769 | −0.2296 |
| H202 | 0.1742 | −0.0142 | −0.2253 |
| H211 | −0.0281 | −0.1580 | −0.2236 |
| H212 | 0.0418 | −0.2183 | −0.1889 |
| H213 | −0.0522 | 0.0728 | −0.1931 |
| H2 | 0.4568 | 0.7450 | −0.0867 |
| H3 | 0.4455 | 0.9047 | −00257 |
| H6 | 0.9900 | 0.7115 | −0.0140 |
| H4 | 0.7487 | 0.9051 | 0.0180 |
| H891 | 0.1791 | 0.0911 | −0.1307 |
| H892 | 0.2524 | −0.1815 | −0.1307 |
| H881 | 0.0688 | −0.3227 | −0.1317 |
| H882 | −0.0006 | −0.0646 | −0.1095 |
| H89 | 0.1389 | 0.3052 | −0.0871 |
| H88 | 0.0278 | −0.3039 | −0.0685 |
| H981 | 0.2546 | −0.0138 | −0.0523 |
| H991 | 0.3186 | 0.3564 | −0.0924 |
| H992 | 0.4542 | 0.2696 | −0.0893 |

Unit cell parameters for the 1,4-butyne-diol solvate If are listed below in Table 11.

TABLE 11

Unit Cell Data for 1,4-Butyne-diol Solvate If

| Form | T | a(Å) | b(Å) | c(Å) | α° | β° | γ° | Z' | SG | $V_m$ | R | $D_{calc}$ |
|---|---|---|---|---|---|---|---|---|---|---|---|---|
| YD-1 (If) | 25 | 21.576(7) | 6.755(1) | 18.335(5) | — | 102.96(1) | — | 1 | C2 | 651 | .055 | 1.339 |
| YD-1 (If) | −50 | 21.537(4) | 6.7273(6) | 18.267(3) | — | 102.924(7) | — | 1 | C2 | 645 | .054 | 1.352 |

T = temp (° C.) for the crystallographic data
Z' = number of drug molecules per asymmetric unit
$V_m$ = V(unit cell)/(Z drug molecules per cell)
R = residual index (I > 2sigma(I))
$D_{calc}$ = density of crystal calculated
SG = space group Table 12 below sets forth the positional parameters for the 1,4-butyne-diol solvate If at 25° C.

TABLE 12

Table of Fractional Atomic Coordinates for
1,4-Butyne-diol Solvate If at T = 25° C.

| Atom | X | Y | Z |
|---|---|---|---|
| CL1 | 0.4766 | 0.0404 | 0.0954 |
| O1 | 0.4009 | 0.0489 | 0.4240 |
| O2 | 0.2487 | 0.0360 | 0.2866 |
| O3 | 0.3361 | 0.3116 | 0.3700 |
| O4 | 0.2980 | −0.0335 | 0.5564 |
| C1 | 0.4341 | −0.0386 | 0.2933 |
| C2 | 0.2694 | −0.0045 | 0.4212 |
| C3 | 0.3808 | 0.0618 | 0.4929 |
| O5 | 0.2184 | −0.1421 | 0.4159 |
| O6 | 0.1438 | 0.7685 | 0.0893 |
| C4 | 0.3553 | 0.1186 | 0.3597 |
| C5 | 0.4405 | 0.0690 | 0.1713 |
| C6 | 0.4608 | −0.0547 | 0.2314 |
| C7 | 0.2958 | −0.0113 | 0.3508 |
| C8 | 0.3662 | 0.2182 | 0.2312 |
| C9 | 0.3737 | 0.3483 | 0.1029 |
| O7 | 0.4545 | −0.2052 | 0.5425 |
| C10 | 0.3205 | −0.0595 | 0.4899 |
| C11 | 0.1993 | 0.4901 | 0.0635 |
| C12 | 0.3137 | 0.4646 | 0.1010 |
| C13 | 0.3863 | 0.0987 | 0.2935 |
| C14 | 0.3927 | 0.2100 | 0.1692 |
| C15 | 0.4368 | −0.0055 | 0.5534 |
| C16 | 0.2546 | 0.3872 | 0.0663 |
| C17 | 0.2011 | 0.6771 | 0.0960 |
| C18 | 0.3867 | 0.4541 | 0.3863 |
| C19 | 0.3147 | 0.6507 | 0.1327 |
| C20 | 0.2589 | 0.7579 | 0.1310 |
| C21 | 0.0758 | 1.0412 | 0.0907 |
| C22 | 0.1428 | 0.9704 | 0.1110 |
| O8 | 0.1617 | 0.3320 | 0.3009 |
| C23 | 0.0884 | 0.7849 | 0.2826 |
| C24 | 0.1613 | 0.4969 | 0.2531 |
| C25 | 0.1208 | 0.6569 | 0.2679 |
| C26 | 0.0508 | 0.9415 | 0.3041 |

TABLE 12-continued

Table of Fractional Atomic Coordinates for
1,4-Butyne-diol Solvate If at T = 25° C.

| Atom | X | Y | Z |
|---|---|---|---|
| O9?* | 0.0699 | 1.0883 | 0.3388 |
| O10* | 0.0921 | 0.9885 | 0.3889 |
| H1 | 0.4482 | −0.1199 | 0.3347 |
| H2 | 0.2539 | 0.1293 | 0.4275 |
| H3 | 0.3717 | 0.2007 | 0.5020 |
| H4 | 0.4923 | −0.1485 | 0.2306 |
| H5 | 0.3090 | −0.1481 | 0.3449 |
| H6 | 0.3335 | 0.3078 | 0.2311 |
| H7 | 0.4083 | 0.4406 | 0.1034 |
| H8 | 03681 | 0.2711 | 0.0573 |
| H9 | 0.3310 | −0.1996 | 0.4860 |
| H10 | 0.1605 | 0.4349 | 0.0399 |
| H11 | 0.4728 | 0.0808 | 0.5536 |
| H12 | 0.4259 | 0.0056 | 0.6018 |
| H13 | 0.2525 | 0.2624 | 0.0444 |
| H14 | 0.4194 | 0.4073 | 0.4272 |
| H15 | 0.3705 | 0.5779 | 0.3998 |
| H16 | 0.4041 | 0.4724 | 0.3430 |
| H17 | 0.3536 | 0.7062 | 0.1557 |
| H18 | 0.2607 | 0.8821 | 0.1533 |
| H19 | 0.0586 | 1.0179 | 0.0384 |
| H20 | 0.0746 | 1.1804 | 0.1009 |
| H21 | 0.0510 | 0.9710 | 0.1197 |
| H22 | 0.1691 | 1.0491 | 0.0855 |
| H23 | 0.1594 | 0.9831 | 0.1645 |
| H24 | 0.2242 | 0.1281 | 0.2970 |
| H25 | 0.1826 | −0.0801 | 0.4013 |
| H26 | 0.2934 | 0.0916 | 0.5641 |
| H27 | 0.4478 | −0.2782 | 0.5791 |
| H28 | 0.1742 | 0.3703 | 0.3468 |
| H30 | 0.0208 | 0.9935 | 0.2512 |
| H31 | 0.0199 | 0.8683 | 0.3354 |
| H32 | 0.2091 | 0.5518 | 0.2594 |
| H33 | 0.1436 | 0.4493 | 0.1953 |

*Atomic occupancy factor is 0.5 due to disorder of 2-butyne-1,4-diol solvent in the crystal structure.

Table 13 below sets forth unit cell parameters for the dimethanol solvate Ig.

TABLE 13

| Unit Cell Data for Dimethanol Solvate Ig | | | | | | | | | | | |
|---|---|---|---|---|---|---|---|---|---|---|---|
| Form | T | a(Å) | b(Å) | c(Å) | α° | β° | γ° | Z' | SG | $V_m$ | R | $D_{calc}$ |
| M2-1 (Ig) | −50 | 20.948(3) | 6.794(2) | 18.333(2) | — | 102.91(2) | — | 1 | C2 | 636 | .038 | 1.314 |

T = temp (° C.) for the crystallographic data
Z' = number of drug molecules per asymmetric unit
$V_m$ = V(unit cell)/(Z drug molecules per cell)
R = residual index (I > 2sigma(I))
$D_{calc}$ = density of crystal calculated
SG = space group Table 14 below sets forth the positional parameters for the dimethanol solvate Ig at −50° C.

TABLE 14

Table of Fractional Atomic Coordinates for Dimethanol
Solvate Ig at T = −50° C.

| Atom | X | Y | Z |
|---|---|---|---|
| CL1 | 0.4845 | 0.0519 | 0.0975 |
| O1 | 0.3999 | 0.0334 | 0.4222 |
| O2 | 0.2438 | 0.0327 | 0.2837 |
| O3 | 0.2919 | −0.0365 | 0.5534 |

TABLE 14-continued

Table of Fractional Atomic Coordinates for Dimethanol Solvate Ig at T = −50° C.

| Atom | X | Y | Z |
|---|---|---|---|
| O4 | 0.2111 | −0.1509 | 0.4115 |
| O5 | 0.1409 | 0.7749 | 0.0877 |
| O6 | 0.3348 | 0.2998 | 0.3692 |
| C1 | 0.3785 | 0.0495 | 0.4912 |
| O7 | 0.4528 | −0.2193 | 0.5428 |
| C2 | 0.4372 | −0.0463 | 0.2932 |
| C3 | 0.3958 | 0.2046 | 0.1690 |
| C4 | 0.3540 | 0.1054 | 0.3588 |
| C5 | 0.2917 | −0.0207 | 0.3471 |
| C6 | 0.2638 | −0.0141 | 0.4180 |
| C7 | 0.4666 | −0.0556 | 0.2324 |
| C8 | 0.4348 | −0.0197 | 0.5521 |
| C9 | 0.3871 | 0.0889 | 0.2923 |
| C10 | 0.3148 | 0.4622 | 0.1014 |
| C11 | 0.3669 | 0.2102 | 0.2310 |
| C12 | 0.1971 | 0.4955 | 0.0616 |
| C13 | 0.3756 | 0.3437 | 0.1035 |
| C14 | 0.3159 | −0.0680 | 0.4873 |
| C15 | 0.2003 | 0.6811 | 0.0949 |
| C16 | 0.2533 | 0.3883 | 0.0643 |
| C17 | 0.4459 | 0.0675 | 0.1722 |
| C18 | 0.3162 | 0.6471 | 0.1342 |
| C19 | 0.2592 | 0.7551 | 0.1318 |
| C20 | 03858 | 0.4414 | 0.3857 |
| C21 | 0.0747 | 1.0555 | 0.0906 |
| C22 | 0.1419 | 0.9708 | 0.1140 |
| O8 | 0.1606 | 0.3410 | 0.3030 |
| C23 | 0.1681 | 0.4908 | 0.2528 |
| O9?* | 0.0905 | 1.0537 | 0.3488 |
| C24 | 0.0506 | 0.9411 | 0.3047 |
| O10* | 0.0871 | 0.9637 | 0.3888 |
| H1 | 0.3698 | 0.1882 | 0.5000 |

TABLE 14-continued

Table of Fractional Atomic Coordinates for Dimethanol Solvate Ig at T = −50° C.

| Atom | X | Y | Z |
|---|---|---|---|
| H2 | 0.4508 | −0.1297 | 0.3339 |
| H3 | 0.3403 | −0.1573 | 0.3401 |
| H4 | 0.2477 | 0.1190 | 0.4240 |
| H5 | 0.5002 | −0.1450 | 0.2324 |
| H6 | 0.4724 | 0.0642 | 0.5527 |
| H7 | 0.4230 | −0.0062 | 0.6000 |
| H8 | 0.3330 | 0.2987 | 0.2309 |
| H9 | 0.1568 | 0.4439 | 0.0375 |
| H10 | 0.4115 | 0.4344 | 0.1041 |
| H11 | 0.3694 | 0.2681 | 0.0576 |
| H12 | 0.3262 | −0.2083 | 0.4845 |
| H13 | 0.2507 | 0.2654 | 0.0414 |
| H14 | 0.3563 | 0.7000 | 0.1585 |
| H15 | 0.2614 | 0.8773 | 0.1551 |
| H16 | 0.4247 | 0.3814 | 0.4147 |
| H17 | 0.3726 | 0.5474 | 0.4136 |
| H18 | 0.3943 | 0.4912 | 0.3398 |

TABLE 14-continued

Table of Fractional Atomic Coordinates for Dimethanol Solvate Ig at T = −50° C.

| Atom | X | Y | Z |
|---|---|---|---|
| H19 | 0.0589 | 1.0375 | 0.0377 |
| H20 | 0.0760 | 1.1934 | 0.1022 |
| H21 | 0.0460 | 0.9899 | 0.1168 |
| H22 | 0.1725 | 1.0486 | 0.0933 |
| H23 | 0.1560 | 0.9729 | 0.1681 |
| H24 | 0.2910 | 0.0922 | 0.5653 |
| H25 | 0.1707 | −0.0975 | 0.3970 |
| H26 | 0.4393 | −0.3086 | 0.5727 |
| H27 | 0.2166 | 0.1321 | 0.2895 |
| H28 | 0.1613 | 0.6164 | 0.2738 |
| H29 | 0.1368 | 0.4726 | 0.2064 |
| H30 | 0.2119 | 0.4855 | 0.2441 |
| H31 | 0.1761 | 0.3807 | 0.3503 |
| H32* | 0.1139 | 1.1530 | 0.3322 |
| H33* | 0.0293 | 0.8376 | 0.3371 |
| H34* | 0.0122 | 1.0286 | 0.2705 |
| H35* | 0.0765 | 0.8620 | 0.2691 |
| H36?* | 0.0718 | 0.8698 | 0.4154 |
| H37?* | 0.0679 | 1.0520 | 0.2715 |
| H38?* | 0.0601 | 0.7968 | 0.2848 |
| H39?* | −0.0015 | 0.9590 | 0.2996 |

*Atomic occupancy factor is 0.5 due to disorder of methanol solvent in the crystal structure.

Unit cell parameters for the 1:2 L-proline complex form 3, formula Ih are listed below in Table 15.

TABLE 15

Unit Cell Data for 1:2 L-Proline Complex (Ih)

| Form | T° | a(Å) | b(Å) | c(Å) | α° | β° | γ° | Z' | SG | $V_m$ | R | $D_{calc}$ |
|---|---|---|---|---|---|---|---|---|---|---|---|---|
| N-1 (Ih) | −60 | 10.311(1) | 11.334(1) | 27.497(1) | 95.94 | 99.22 | 90 | 4 | $P_1$ | 789 | 0.1 | 1.343 |

T = temp (° C.) for crystallographic data
Z' = number of drug molecules per asymmetric unit
$V_m$ = V (unit cell)/(Z drug molecules per cell)
R = residual index (I > 3sigma(I))
$D_{calc}$ = density of crystal calculated
SG = space group Table 15A below sets forth the positional parameters for the 1:2 L-proline complex (Ih) neat form N-1 at T=−60° C.

TABLE 15A

Table of Fractional Atomic Coordinates for Compound Ih 1:2 Complex with L-Proline (Form N-1)

| Atom | X | Y | Z |
|---|---|---|---|
| Cl1 | 0.8511 | 0.3142 | 0.4683 |
| O2 | 0.1890 | 0.4635 | 0.4796 |
| O3 | 0.7564 | 0.4104 | 0.2284 |
| O4 | 0.4729 | 0.5010 | 0.2885 |
| O5 | 0.4376 | 0.6313 | 0.2067 |
| O6 | 0.8989 | 0.3300 | 0.1500 |
| C7 | 0.2926 | 0.3792 | 0.4153 |
| C8 | 0.6818 | 0.2711 | 0.3799 |
| C9 | 0.5724 | 0.5066 | 0.2584 |
| C10 | 0.7120 | 0.3675 | 0.3085 |
| C11 | 0.6191 | 0.5325 | 0.1740 |
| O12 | 0.5675 | 0.5324 | 0.1226 |
| C13 | 0.8659 | 0.4113 | 0.3834 |

TABLE 15A-continued

Table of Fractional Atomic Coordinates for Compound Ih 1:2 Complex with L-Proline (Form N-1)

| Atom | X | Y | Z |
|---|---|---|---|
| C14 | 0.6573 | 0.3919 | 0.2567 |
| C15 | 0.7888 | 0.3318 | 0.4049 |
| C16 | 0.3975 | 0.3524 | 0.4995 |
| C17 | 0.5114 | 0.5240 | 0.2053 |
| C18 | 0.7053 | 0.4187 | 0.1784 |
| C19 | 0.2907 | 0.3910 | 0.4630 |
| C20 | 0.4894 | 0.2664 | 0.4264 |
| C21 | 0.4996 | 0.2842 | 0.4793 |
| C22 | 0.8273 | 0.4301 | 0.3341 |
| C23 | 0.2056 | 0.4854 | 0.5344 |
| C24 | 0.8279 | 0.4316 | 0.1519 |
| C25 | 0.3898 | 0.3142 | 0.3967 |
| C26 | 0.5990 | 0.1967 | 0.4055 |
| C27 | 0.6395 | 0.2861 | 0.3305 |
| C28 | 0.0776 | 0.5599 | 0.5411 |
| Cl29 | 0.8615 | 0.7651 | 0.4622 |
| O30 | 0.4735 | 1.0020 | 0.2917 |
| O31 | 0.4387 | 1.1337 | 0.2094 |
| O32 | 0.7479 | 0.9028 | 0.2288 |
| O33 | 0.8902 | 0.8251 | 0.1497 |
| C34 | 0.8261 | 0.9016 | 0.3336 |
| C35 | 0.6485 | 0.8878 | 0.2580 |
| O36 | 0.5610 | 1.0347 | 0.1249 |
| C37 | 0.6759 | 0.7507 | 0.3797 |
| C38 | 0.5079 | 1.0262 | 0.2062 |
| C39 | 0.4780 | 0.7554 | 0.4220 |
| C40 | 0.6312 | 0.7804 | 0.3315 |
| O41 | 0.1584 | 0.9450 | 0.4656 |
| C42 | 0.7041 | 0.8583 | 0.3076 |
| C43 | 0.3624 | 0.6994 | 0.4359 |
| C44 | 0.8678 | 0.8769 | 0.3809 |
| C45 | 0.5696 | 1.0064 | 0.2602 |
| C46 | 0.6975 | 0.9154 | 0.1787 |
| C47 | 0.3635 | 0.9472 | 0.4341 |
| C48 | 0.6156 | 1.0330 | 0.1758 |
| C49 | 0.2666 | 0.7602 | 0.4513 |
| C50 | 0.2689 | 0.8865 | 0.4494 |
| C51 | 0.4642 | 0.8736 | 0.4176 |
| C52 | 0.8214 | 0.9316 | 0.1526 |
| C53 | 0.5864 | 0.6836 | 0.4051 |
| C54 | 0.7948 | 0.8027 | 0.4039 |
| C55 | 0.1465 | 1.0758 | 0.4752 |
| C56 | 0.2078 | 1.0792 | 0.5264 |
| C73 | 0.7131 | 0.5906 | 0.5918 |
| C74 | 0.6549 | 0.5814 | 0.5389 |
| Cl75 | 0.0092 | 0.3008 | 0.6072 |
| O76 | 0.1209 | 0.5563 | 0.8403 |
| O77 | 0.3970 | 0.6243 | 0.7788 |
| C78 | 0.2253 | 0.5273 | 0.8121 |
| C79 | 0.3613 | 0.6922 | 0.8623 |
| C80 | 0.1934 | 0.3303 | 0.6884 |
| C81 | 0.1674 | 0.4723 | 0.7614 |
| C82 | 0.2412 | 0.3835 | 0.7390 |
| C83 | −0.0019 | 0.4492 | 0.6892 |
| O84 | 0.4278 | 0.7982 | 0.8605 |
| O85 | −0.0213 | 0.5180 | 0.9192 |
| C86 | 0.0441 | 0.5055 | 0.7380 |
| O87 | 0.7087 | 0.4793 | 0.6025 |
| C88 | 0.1729 | 0.5956 | 0.8909 |
| C89 | 0.4982 | 0.4992 | 0.6339 |
| C90 | 0.5097 | 0.2528 | 0.6324 |
| C91 | 0.3008 | 0.6402 | 0.8083 |
| C92 | 0.3983 | 0.4301 | 0.6518 |
| O93 | 0.3078 | 0.7393 | 0.9449 |
| C94 | 0.2809 | 0.2490 | 0.6650 |
| C95 | 0.3930 | 0.3137 | 0.6470 |
| C96 | 0.0746 | 0.3688 | 0.6663 |
| C97 | 0.6122 | 0.3067 | 0.6180 |
| C98 | 0.2545 | 0.7117 | 0.8934 |
| C99 | 0.6095 | 0.4314 | 0.6189 |
| C100 | 0.0478 | 0.6254 | 0.9173 |
| Cl10 | 0.0184 | 0.8459 | 0.6019 |
| O102 | 0.3952 | 1.1247 | 0.7804 |
| O103 | 0.1147 | 1.0661 | 0.8415 |
| O104 | 0.6781 | 0.9872 | 0.5898 |
| O105 | 0.4317 | 1.2935 | 0.8633 |
| C106 | 0.5806 | 0.9279 | 0.6059 |
| C107 | 0.4768 | 0.8827 | 0.6738 |
| C108 | 0.1859 | 0.8490 | 0.6890 |
| C109 | 0.5840 | 0.9396 | 0.6532 |
| C110 | 0.3778 | 0.8134 | 0.5924 |
| C111 | 0.2988 | 1.1454 | 0.8102 |
| O112 | 0.3053 | 1.2394 | 0.9473 |
| O113 | −0.0298 | 1.0236 | 0.9198 |
| C114 | 0.1616 | 0.9797 | 0.7616 |
| C115 | 0.4712 | 0.8729 | 0.5711 |
| C116 | 0.1655 | 1.0994 | 0.8923 |
| C117 | 0.2173 | 1.0311 | 0.8129 |
| C118 | 0.2502 | 1.2127 | 0.8951 |
| C119 | 0.3763 | 0.8179 | 0.6434 |
| C120 | 0.0002 | 0.9826 | 0.6866 |
| C121 | 0.6693 | 0.9881 | 0.5388 |
| C122 | 0.2312 | 0.8864 | 0.7377 |
| C123 | 0.3605 | 1.1913 | 0.8637 |
| C124 | 0.0428 | 1.0292 | 0.7357 |
| C125 | 0.7936 | 1.0536 | 0.5306 |
| C126 | 0.0458 | 1.1266 | 0.9182 |
| C127 | 0.0732 | 0.8975 | 0.6629 |
| C128 | 0.2697 | 0.7610 | 0.6655 |
| O129 | 0.1176 | 0.8835 | 0.2145 |
| N130 | 0.2152 | 0.6016 | 0.2596 |
| C131 | 0.1172 | 0.6843 | 0.2345 |
| O132 | 0.2914 | 0.8241 | 0.2651 |
| C133 | 0.1853 | 0.8095 | 0.2384 |
| C134 | 0.1980 | 0.6021 | 0.3121 |
| C135 | 0.0814 | 0.6857 | 0.3187 |
| C136 | 0.0075 | 0.6839 | 0.2657 |
| O137 | 0.5811 | 0.9560 | 0.8015 |
| O138 | 0.7490 | 1.0434 | 0.8543 |
| C139 | 0.7527 | 0.8332 | 0.8327 |
| C140 | 0.6889 | 0.9523 | 0.8297 |
| N141 | 0.6668 | 0.7335 | 0.8097 |
| C142 | 0.6961 | 0.7064 | 0.7572 |
| C143 | 0.8711 | 0.8236 | 0.8064 |
| C144 | 0.8046 | 0.7903 | 0.7522 |
| C145 | 0.2901 | 0.3199 | 0.2689 |
| N146 | 0.2077 | 0.0992 | 0.2607 |
| C147 | 0.1849 | 0.3081 | 0.2401 |
| O148 | 0.1224 | 0.3825 | 0.2158 |
| C149 | 0.1134 | 0.1822 | 0.2345 |
| C150 | −0.0001 | 0.1822 | 0.2639 |
| C151 | 0.1765 | 0.0951 | 0.3122 |
| C152 | 0.0624 | 0.1788 | 0.3149 |
| C153 | 0.7503 | 0.3375 | 0.8345 |
| O154 | 0.7509 | 0.5453 | 0.8549 |
| O155 | 0.5797 | 0.4581 | 0.8039 |
| N156 | 0.6576 | 0.2389 | 0.8101 |
| C157 | 0.6884 | 0.4556 | 0.8306 |
| C158 | 0.8656 | 0.3215 | 0.8057 |
| C159 | 0.7926 | 0.2957 | 0.7527 |
| C160 | 0.6813 | 0.2179 | 0.7580 |
| O57 | 0.2706 | 0.6596 | 0.1242 |
| O58 | 0.4116 | 0.7306 | 0.0823 |
| N59 | 0.2962 | 0.9340 | 0.0695 |
| C60 | 0.3243 | 0.7268 | 0.1018 |
| C61 | 0.2366 | 0.8510 | 0.0985 |
| C62 | 0.2021 | 0.9562 | 0.0266 |
| C63 | 0.0946 | 0.8269 | 0.0685 |
| C64 | 0.0736 | 0.9268 | 0.0393 |
| O65 | 0.2708 | 0.1591 | 0.1241 |
| O66 | 0.4177 | 0.2319 | 0.0834 |
| N67 | 0.2949 | 0.4330 | 0.0684 |
| C68 | 0.2341 | 0.3504 | 0.0971 |
| C69 | 0.3311 | 0.2307 | 0.1033 |
| C70 | 0.0690 | 0.4256 | 0.0394 |
| C71 | 0.1944 | 0.4576 | 0.0266 |
| C72 | 0.0916 | 0.3239 | 0.0659 |
| C161 | 0.5540 | 0.4526 | 0.9706 |
| O162 | 0.4543 | 0.4603 | 0.9840 |
| O163 | 0.6026 | 0.3671 | 0.9467 |

TABLE 15A-continued

Table of Fractional Atomic Coordinates for Compound Ih 1:2 Complex with L-Proline (Form N-1)

| Atom | X | Y | Z |
|---|---|---|---|
| N164 | 0.5722 | 0.6674 | 0.9975 |
| C165 | 0.7962 | 0.6796 | 1.0284 |
| C166 | 0.7705 | 0.5623 | 1.0029 |
| C167 | 0.6633 | 0.7048 | 1.0426 |
| C168 | 0.6369 | 0.5668 | 0.9718 |
| N169 | 0.5736 | 1.1664 | 0.9988 |
| C170 | 0.6413 | 1.0706 | 0.9734 |
| C171 | 0.6566 | 1.2036 | 1.0440 |
| C172 | 0.7913 | 1.1762 | 1.0303 |
| C173 | 0.7728 | 1.0572 | 1.0049 |
| O174 | 0.5984 | 0.8670 | 0.9446 |
| O175 | 0.4528 | 0.9612 | 0.9826 |
| C176 | 0.5532 | 0.9542 | 0.9687 |
| H104 | 0.4098 | 0.4245 | 0.2757 |
| H1 | 0.5933 | 0.3154 | 0.2391 |
| H11 | 0.6757 | 0.6123 | 0.1863 |
| H25 | 0.3866 | 0.3009 | 0.3571 |
| H7 | 0.2181 | 0.4202 | 0.3906 |
| H16 | 0.4003 | 0.3732 | 0.5389 |
| H21 | 0.5801 | 0.2482 | 0.5031 |
| H231 | 0.2065 | 0.4036 | 0.5514 |
| H230 | 0.2944 | 0.5361 | 0.5495 |
| H260 | 0.5550 | 0.1248 | 0.3793 |
| H261 | 0.6617 | 0.1611 | 0.4357 |
| H22 | 0.8817 | 0.4891 | 0.3161 |
| H27 | 0.5549 | 0.2379 | 0.3095 |
| H13 | 0.9521 | 0.4556 | 0.4051 |
| H24B | 0.8905 | 0.5029 | 0.1720 |
| H24A | 0.7945 | 0.4527 | 0.1146 |
| H18 | 0.6455 | 0.3409 | 0.1637 |
| H9 | 0.6364 | 0.5818 | 0.2730 |
| H17 | 0.4471 | 0.4497 | 0.1897 |
| H6O | 0.9902 | 0.3430 | 0.1754 |
| H5O | 0.3733 | 0.6344 | 0.1718 |
| H12 | 0.5145 | 0.6132 | 0.1167 |
| H730 | 0.4058 | 0.9277 | 0.2777 |
| H35 | 0.5824 | 0.8169 | 0.2387 |
| H34 | 0.8870 | 0.9544 | 0.3141 |
| H48 | 0.6718 | 1.1140 | 0.1882 |
| H43 | 0.3564 | 0.6038 | 0.4332 |
| H49 | 0.1884 | 0.7171 | 0.4650 |
| H51 | 0.5357 | 0.9155 | 0.4000 |
| H47 | 0.3640 | 1.0426 | 0.4342 |
| H550 | 0.2010 | 1.1248 | 0.4533 |
| H551 | 0.0459 | 1.1049 | 0.4708 |
| H53A | 0.5434 | 0.6098 | 0.3796 |
| H53B | 0.6443 | 0.6506 | 0.4370 |
| H44 | 0.9590 | 0.9156 | 0.4010 |
| H40 | 0.5387 | 0.7432 | 0.3119 |
| H46 | 0.6347 | 0.8402 | 0.1631 |
| H45 | 0.6370 | 1.0795 | 0.2743 |
| H52B | 0.8851 | 1.0006 | 0.1739 |
| H52A | 0.7895 | 0.9562 | 0.1157 |
| H38 | 0.4415 | 0.9538 | 0.1901 |
| H33O | 0.9838 | 0.8359 | 0.1739 |
| H36 | 0.5133 | 1.1183 | 0.1197 |
| H31 | 0.3740 | 1.1406 | 0.1748 |
| H78 | 0.2893 | 0.4626 | 0.8307 |
| H91 | 0.2300 | 0.7037 | 0.7933 |
| H79 | 0.4290 | 0.6296 | 0.8786 |
| H73A | 0.8131 | 0.6240 | 0.5975 |
| H73B | 0.6558 | 0.6475 | 0.6139 |
| H97 | 0.6926 | 0.2563 | 0.6062 |
| H90 | 0.5135 | 0.1579 | 0.6334 |
| H92 | 0.3254 | 0.4776 | 0.6699 |
| H89 | 0.4904 | 0.5936 | 0.6319 |
| H94B | 0.3235 | 0.1904 | 0.6915 |
| H94A | 0.2237 | 0.1976 | 0.6335 |
| H83 | −0.0976 | 0.4703 | 0.6701 |
| H86 | −0.0138 | 0.5707 | 0.7560 |
| H82 | 0.3324 | 0.3549 | 0.7591 |
| H98 | 0.1908 | 0.7806 | 0.8796 |
| H88 | 0.2352 | 0.5280 | 0.9067 |
| H100 | −0.0156 | 0.6845 | 0.8964 |
| H101 | 0.0795 | 0.6672 | 0.9544 |
| H77O | 0.4635 | 0.5569 | 0.7921 |
| H84O | 0.4937 | 0.8202 | 0.8949 |
| H93O | 0.3569 | 0.8249 | 0.9503 |
| H85O | −0.1149 | 0.5173 | 0.8950 |
| H117 | 0.2800 | 0.9658 | 0.8316 |
| H123 | 0.4233 | 1.1238 | 0.8797 |
| H111 | 0.2317 | 1.2108 | 0.7948 |
| H228 | 0.3143 | 0.7048 | 0.6931 |
| H128 | 0.2074 | 0.7050 | 0.6363 |
| H12A | 0.6658 | 0.8985 | 0.5209 |
| H12B | 0.5824 | 1.0343 | 0.5241 |
| H915 | 0.4621 | 0.8772 | 0.5316 |
| H909 | 0.6624 | 0.9895 | 0.6775 |
| H107 | 0.4780 | 0.8924 | 0.7134 |
| H910 | 0.3024 | 0.7608 | 0.5678 |
| H124 | −0.0101 | 1.0987 | 0.7537 |
| H120 | −0.0905 | 1.0129 | 0.6667 |
| H122 | 0.3164 | 0.8472 | 0.7576 |
| H116 | 0.2250 | 1.0292 | 0.9073 |
| H926 | −0.0153 | 1.1891 | 0.8983 |
| H826 | 0.0798 | 1.1653 | 0.9557 |
| H118 | 0.1903 | 1.2849 | 0.8822 |
| H902 | 0.4593 | 1.0560 | 0.7941 |
| H105 | 0.4954 | 1.3127 | 0.8984 |
| H112 | 0.3566 | 1.3240 | 0.9528 |
| H113 | −0.1207 | 1.0256 | 0.8942 |
| H130 | 0.0880 | 0.6513 | 0.1960 |
| H930 | 0.1989 | 0.5128 | 0.2411 |
| H131 | 0.3065 | 0.6289 | 0.2579 |
| H936 | −0.0527 | 0.7614 | 0.2616 |
| H137 | −0.0535 | 0.6049 | 0.2555 |
| H136 | 0.0202 | 0.6522 | 0.3427 |
| H935 | 0.1160 | 0.7743 | 0.3334 |
| H134 | 0.1753 | 0.5137 | 0.3200 |
| H135 | 0.2861 | 0.6352 | 0.3365 |
| H944 | 0.9296 | 0.9035 | 0.8114 |
| H143 | 0.9361 | 0.7508 | 0.8190 |
| H244 | 0.8750 | 0.7504 | 0.7303 |
| H144 | 0.7682 | 0.8708 | 0.7360 |
| H139 | 0.7802 | 0.8212 | 0.8719 |
| H742 | 0.7271 | 0.6158 | 0.7513 |
| H842 | 0.6099 | 0.7203 | 0.7306 |
| H541 | 0.6871 | 0.6572 | 0.8300 |
| H641 | 0.5726 | 0.7555 | 0.8089 |
| H952 | 0.0994 | 0.2669 | 0.3315 |
| H252 | −0.0039 | 0.1476 | 0.3381 |
| H150 | −0.0603 | 0.2607 | 0.2596 |
| H250 | −0.0651 | 0.1042 | 0.2518 |
| H151 | 0.1486 | 0.0063 | 0.3177 |
| H152 | 0.2600 | 0.1251 | 0.3397 |
| H460 | 0.1968 | 0.0115 | 0.2409 |
| H461 | 0.3000 | 0.1287 | 0.2626 |
| H149 | 0.0881 | 0.1498 | 0.1958 |
| H161 | 0.7059 | 0.1256 | 0.7481 |
| H160 | 0.5948 | 0.2388 | 0.7319 |
| H159 | 0.7564 | 0.3753 | 0.7372 |
| H259 | 0.8547 | 0.2500 | 0.7286 |
| H153 | 0.7784 | 0.3252 | 0.8732 |
| H958 | 0.9256 | 0.4012 | 0.8101 |
| H959 | 0.9261 | 0.2481 | 0.8168 |
| H957 | 0.6775 | 0.1597 | 0.8286 |
| H956 | 0.5646 | 0.2627 | 0.8110 |
| H620 | 0.2066 | 1.0481 | 0.0198 |
| H62 | 0.2205 | 0.9003 | −0.0057 |
| H640 | 0.0377 | 1.0016 | 0.0607 |
| H64 | 0.0037 | 0.9030 | 0.0061 |
| H63 | 0.0897 | 0.7441 | 0.0449 |
| H630 | 0.0231 | 0.8249 | 0.0931 |
| H61 | 0.2352 | 0.8932 | 0.1354 |
| H590 | 0.3226 | 1.0165 | 0.0923 |
| H59 | 0.3766 | 0.8979 | 0.0586 |
| H68 | 0.2264 | 0.3961 | 0.1333 |
| H710 | 0.1967 | 0.5506 | 0.0213 |
| H71 | 0.2110 | 0.4051 | −0.0068 |
| H700 | 0.0336 | 0.4977 | 0.0623 |

TABLE 15A-continued

Table of Fractional Atomic Coordinates for Compound Ih 1:2 Complex with L-Proline (Form N-1)

| Atom | X | Y | Z |
|---|---|---|---|
| H70 | −0.0021 | 0.4046 | 0.0062 |
| H72 | 0.0901 | 0.2437 | 0.0409 |
| H720 | 0.0195 | 0.3163 | 0.0900 |
| H670 | 0.3256 | 0.5143 | 0.0915 |
| H67 | 0.3726 | 0.3954 | 0.0559 |
| H666 | 0.8439 | 0.5395 | 0.9797 |
| H766 | 0.7706 | 0.4978 | 1.0292 |
| H665 | 0.8720 | 0.6797 | 1.0604 |
| H765 | 0.8229 | 0.7417 | 1.0042 |
| H767 | 0.6538 | 0.7982 | 1.0537 |
| H667 | 0.6468 | 0.6543 | 1.0723 |
| H168 | 0.6429 | 0.5849 | 0.9344 |
| H664 | 0.4798 | 0.6384 | 1.0063 |
| H764 | 0.5568 | 0.7339 | 0.9761 |
| H170 | 0.6545 | 1.0931 | 0.9372 |
| H673 | 0.7695 | 0.9914 | 1.0304 |
| H773 | 0.8485 | 1.0349 | 0.9826 |
| H672 | 0.8184 | 1.2380 | 1.0061 |
| H772 | 0.8655 | 1.1783 | 1.0629 |
| H671 | 0.6469 | 1.2971 | 1.0548 |
| H771 | 0.6369 | 1.1536 | 1.0734 |
| H669 | 0.5570 | 1.2393 | 0.9763 |
| H769 | 0.4876 | 1.1366 | 1.0054 |

Unit cell parameters for the 1:1 L-proline complex neat form N-1 (form 6), formula Ii are listed below in Table 16.

TABLE 16

Unit Cell Data for 1:1 L-Proline Complex (Ii)

| Form | T° | a(Å) | b(Å) | c(Å) | α° | β° | γ° | Z' | SG | $V_m$ | R | $D_{calc}$ |
|---|---|---|---|---|---|---|---|---|---|---|---|---|
| N-1 (Ii) | −40 | 11.441(1) | 10.235(1) | 45.358(1) | 90 | 90 | 90 | 2 | $P2_12_12_1$ | 664 | 0.08 | 1.311 |

T = temp (° C.) for crystallographic data

Z' = number of drug molecules per asymmetric unit $V_m$ = V (unit cell)/(Z drug molecules per cell)

R = residual index (I > 3sigma(I))

$D_{calc}$ = density of crystal calculated

SG = space group

Table 16A below sets forth the positional parameters for the 1:1 L-proline complex (Ii) neat form N-1 at T=−40° C.

TABLE 16A

Table of Fractional Atomic Coordinates for Compound Ii 1:1 Complex with L-Proline

| Atom | X | Y | Z |
|---|---|---|---|
| Cl1 | 0.4598 | −0.1973 | 0.4564 |
| C1 | 0.5901 | −0.2370 | 0.3766 |
| C2 | 0.4455 | −0.0618 | 0.3755 |
| C3 | 0.4764 | −0.1649 | 0.4212 |
| C4 | 0.5631 | −0.2563 | 0.4083 |
| C5 | 0.5270 | −0.1401 | 0.3597 |
| C6 | 0.4236 | −0.0847 | 0.4052 |
| C7 | 0.3350 | 0.0181 | 0.4193 |
| C8 | 0.4043 | 0.1572 | 0.4619 |
| C9 | 0.4038 | 0.1366 | 0.4305 |
| C10 | 0.4700 | 0.2275 | 0.4154 |
| O1 | 0.5531 | −0.2303 | 0.3104 |
| C11 | 0.6684 | −0.0473 | 0.3232 |
| C12 | 0.6871 | −0.1530 | 0.2745 |
| O2 | 0.6765 | 0.0755 | 0.3403 |
| C13 | 0.5634 | −0.2137 | 0.2780 |
| C14 | 0.5532 | −0.1047 | 0.3260 |
| C15 | 0.6982 | −0.0231 | 0.2901 |
| C16 | 0.5401 | −0.3394 | 0.2628 |
| O3 | 0.7021 | −0.1304 | 0.2442 |
| O4 | 0.8064 | 0.0378 | 0.2896 |
| O5 | 0.5831 | 0.4559 | 0.4668 |
| C17 | 0.5134 | 0.3474 | 0.4583 |
| C18 | 0.6039 | 0.5020 | 0.4977 |
| C19 | 0.6740 | 0.6076 | 0.4990 |
| O6 | 0.6178 | −0.4307 | 0.2703 |
| C20 | 0.4646 | 0.2450 | 0.4744 |
| C21 | 0.5212 | 0.3364 | 0.4270 |
| C12 | −0.1014 | −0.2193 | 0.4531 |
| O7 | 0.0403 | −0.2096 | 0.3126 |
| C22 | 0.0502 | −0.0977 | 0.3307 |
| C23 | −0.0026 | −0.1191 | 0.3614 |
| C24 | 0.1707 | −0.0312 | 0.3288 |
| C25 | 0.0641 | −0.1848 | 0.2832 |
| C26 | 0.1903 | −0.1171 | 0.2772 |
| C27 | 0.0159 | −0.2652 | 0.4010 |
| C28 | 0.0413 | −0.3076 | 0.2646 |
| O8 | 0.1732 | 0.0766 | 0.3473 |
| C29 | 0.0527 | −0.2262 | 0.3719 |
| C30 | −0.0488 | −0.1911 | 0.4174 |
| O9 | 0.2066 | −0.1046 | 0.2477 |
| C31 | −0.1057 | −0.0845 | 0.4057 |
| C32 | −0.0805 | −0.0464 | 0.3769 |
| C33 | −0.1758 | 0.0315 | 0.4210 |
| C34 | −0.0962 | 0.3657 | 0.4497 |
| C35 | 0.0119 | 0.1514 | 0.4289 |
| C36 | −0.1670 | 0.2596 | 0.4419 |
| O10 | 0.0892 | 0.4864 | 0.4561 |
| C37 | 0.0235 | 0.3777 | 0.4487 |
| C38 | 0.0796 | 0.2657 | 0.4373 |
| C39 | 0.2088 | 0.4743 | 0.4694 |
| C40 | 0.2378 | 0.6027 | 0.4670 |
| C41 | −0.1056 | 0.1472 | 0.4292 |
| O11 | 0.3103 | 0.0473 | 0.2955 |
| C42 | 0.1927 | −0.0117 | 0.2972 |
| O12 | 0.1209 | −0.4060 | 0.2699 |
| C43 | −0.1355 | 0.5267 | 0.3371 |
| C44 | −0.1317 | 0.4102 | 0.3168 |
| N1 | −0.2217 | 0.3229 | 0.3311 |
| C45 | −0.1578 | 0.4809 | 0.3661 |
| C46 | −0.2328 | 0.3526 | 0.3628 |
| O13 | 0.0687 | 0.4002 | 0.3090 |
| O14 | −0.0027 | 0.2411 | 0.3344 |

TABLE 16A-continued

Table of Fractional Atomic Coordinates for Compound Ii 1:1 Complex with L-Proline

| Atom | X | Y | Z |
|---|---|---|---|
| C47 | −0.0235 | 0.3422 | 0.3215 |
| C48 | 0.3738 | 0.4173 | 0.3220 |
| C49 | 0.3666 | 0.5397 | 0.3405 |
| C50 | 0.3232 | 0.5141 | 0.3706 |
| O15 | 0.5678 | 0.3983 | 0.3126 |
| O16 | 0.4793 | 0.2316 | 0.3356 |
| N2 | 0.2751 | 0.3408 | 0.3341 |
| C51 | 0.2568 | 0.3858 | 0.3637 |
| C52 | 0.4900 | 0.3392 | 0.3227 |
| C53 | 0.1894 | 0.5037 | 0.4979 |
| H1 | 0.2977 | −0.0348 | 0.4380 |
| H2 | 0.5158 | 0.5126 | 0.5088 |
| H3 | 0.6427 | 0.4151 | 0.5106 |
| H4 | 0.4640 | 0.2425 | 0.4980 |
| H5 | 0.3557 | 0.0952 | 0.4743 |
| H6 | 0.4028 | 0.0143 | 0.3656 |
| H7 | 0.4846 | −0.0412 | 0.3172 |
| H8 | 0.7354 | −0.1139 | 0.3309 |
| H9 | 0.6383 | 0.0438 | 0.2803 |
| H10 | 0.7509 | −0.2206 | 0.2829 |
| H11 | 0.4937 | −0.1547 | 0.2692 |
| H12 | 0.4535 | −0.3750 | 0.2689 |
| H13 | 0.5440 | −0.3256 | 0.2395 |
| H14 | 0.5987 | 0.1273 | 0.3371 |
| H15 | 0.5850 | −0.4862 | 0.2863 |
| H16 | 0.2740 | 0.0426 | 0.4038 |
| H17 | 0.7825 | −0.0885 | 0.2400 |
| H18 | 0.8274 | 0.0552 | 0.2680 |
| H19 | 0.4902 | 0.2088 | 0.3946 |
| H20 | 0.5540 | 0.4072 | 0.4143 |
| H21 | 0.6504 | −0.2925 | 0.3665 |
| H22 | 0.6030 | −0.3278 | 0.4194 |
| H23 | 0.2586 | −0.1789 | 0.2863 |
| H24 | 0.1267 | 0.0606 | 0.2892 |
| H25 | 0.2335 | −0.1001 | 0.3377 |
| H26 | 0.0060 | −0.0175 | 0.3198 |
| H27 | −0.0022 | −0.1194 | 0.2737 |
| H28 | −0.0459 | −0.3511 | 0.2701 |
| H29 | 0.0431 | −0.2942 | 0.2411 |
| H30 | 0.1118 | −0.2782 | 0.3606 |
| H31 | −0.1170 | 0.0351 | 0.3696 |
| H32 | 0.0467 | −0.3485 | 0.4096 |
| H33 | −0.2543 | 0.2691 | 0.4432 |
| H34 | −0.1353 | 0.4445 | 0.4589 |
| H35 | 0.0544 | 0.0664 | 0.4241 |
| H36 | 0.1640 | 0.2598 | 0.4365 |
| H37 | −0.2417 | 0.0673 | 0.4058 |
| H38 | −0.2171 | 0.0017 | 0.4412 |
| H39 | 0.2698 | −0.0400 | 0.2435 |
| H40 | 0.3320 | 0.0534 | 0.2734 |
| H41 | 0.1058 | 0.1381 | 0.3420 |
| H42 | 0.0874 | −0.4719 | 0.2852 |
| H43 | −0.1506 | 0.4388 | 0.2950 |
| H44 | −0.0541 | 0.5810 | 0.3377 |
| H45 | −0.2055 | 0.5941 | 0.3310 |
| H46 | −0.0797 | 0.4553 | 0.3782 |
| H47 | −0.2106 | 0.5460 | 0.3796 |
| H48 | −0.3210 | 0.3680 | 0.3662 |
| H49 | −0.1958 | 0.2728 | 0.3734 |
| H50 | −0.2972 | 0.3381 | 0.3195 |
| H51 | −0.1983 | 0.2279 | 0.3269 |
| H52 | 0.3544 | 0.4339 | 0.2980 |
| H53 | 0.2791 | 0.3273 | 0.3822 |
| H54 | 0.1634 | 0.4233 | 0.3683 |
| H55 | 0.4032 | 0.5053 | 0.3835 |
| H56 | 0.2799 | 0.6038 | 0.3764 |
| H57 | 0.4555 | 0.5795 | 0.3393 |
| H58 | 0.3097 | 0.6065 | 0.3283 |
| H59 | 0.2013 | 0.3456 | 0.3219 |
| H60 | 0.2977 | 0.2420 | 0.3345 |

Unit cell parameters for the 1:1 L-proline hemihydrate complex H.5-2 Ij are listed below in Table 17.

TABLE 17

Unit Cell Data for Compound I Complex with L-Proline Hemihydrate Form H.5-2

| Form | T° C. | a(Å) | b(Å) | c(Å) | α° | β° | γ° | Z' | SG | $V_m$ | R | $D_{calc}$ |
|---|---|---|---|---|---|---|---|---|---|---|---|---|
| H.5-2 | −40 | 11.539 | 10.199 | 23.183 | 103.96 | 97.16 | 90.25 | 4 | $P_1$ | 656 | .06 | 1.349 |

T = temp (° C.) for crystallographic data
Z' = number of drug molecules per asymmetric unit
$V_m$ = V (unit cell)/(Z drug molecules per cell)
R = residual index (I > 2sigma(I))
$D_{calc}$ = density of crystal calculated
SG = space group Table 18 below sets forth the positional parameters for the 1:1 L-proline hemihydrate form H.5-2 Ij.

TABLE 18

Table of Fractional Atomic Coordinates for Compound Ij 1:1 Complex with L-Proline Hemihydrate Form H.5-2 at T = −40° C.

| Atom | X | Y | Z |
|---|---|---|---|
| CL1 | −0.3207 | 0.2999 | 0.1007 |
| O2 | −0.0812 | 0.4445 | 0.3860 |
| O3 | 0.1266 | 0.3986 | 0.5119 |
| O4 | 0.0226 | 0.1123 | 0.3131 |
| O5 | 0.1988 | 0.2024 | 0.4116 |
| C6 | −0.0400 | 0.4518 | 0.4471 |
| C7 | 0.0829 | 0.3978 | 0.4505 |
| C8 | 0.0836 | 0.2539 | 0.4134 |
| O9 | 0.0185 | 0.6897 | 0.4693 |
| C10 | 0.0320 | 0.2460 | 0.3495 |
| C11 | −0.1475 | 0.3075 | 0.2867 |
| C12 | −0.0536 | 0.5937 | 0.4833 |
| C13 | −0.2858 | 0.1976 | 0.1996 |

TABLE 18-continued

Table of Fractional Atomic Coordinates for Compound Ij 1:1 Complex with L-Proline Hemihydrate Form H.5-2 at T = −40° C.

| Atom | X | Y | Z |
| --- | --- | --- | --- |
| O14 | −0.1314 | −0.4139 | 0.0970 |
| C15 | −0.0913 | 0.3083 | 0.3494 |
| C16 | −0.2316 | 0.2099 | 0.2582 |
| C17 | −0.1691 | 0.4011 | 0.2002 |
| C18 | −0.1786 | −0.0508 | 0.1507 |
| C19 | −0.3006 | −0.0480 | 0.1494 |
| C20 | −0.3629 | −0.1768 | 0.1287 |
| C21 | −0.1830 | −0.2916 | 0.1133 |
| C22 | −0.1179 | 0.4052 | 0.2576 |
| C23 | −0.1249 | −0.1696 | 0.1325 |
| C24 | −0.2541 | 0.3000 | 0.1727 |
| C25 | −0.3658 | 0.0787 | 0.1687 |
| C26 | −0.3038 | −0.2938 | 0.1114 |
| C27 | −0.0150 | −0.4216 | 0.0824 |
| C28 | −0.0248 | −0.4143 | 0.0214 |
| CL29 | 0.6985 | 0.3144 | 0.9332 |
| O30 | 0.9914 | 0.4113 | 0.6104 |
| O31 | 0.7834 | 0.1123 | 0.6447 |
| O32 | 0.8541 | 0.4766 | 0.7040 |
| O33 | 0.7408 | 0.2570 | 0.7376 |
| O34 | 0.9142 | 0.1720 | 0.5162 |
| O35 | 0.7084 | −0.1271 | 0.5485 |
| C36 | 0.7611 | 0.2500 | 0.6736 |
| O37 | 0.8359 | 0.9717 | 0.9453 |
| C38 | 0.7967 | 0.0998 | 0.5824 |
| C39 | 0.8661 | 0.3408 | 0.6732 |
| C40 | 0.8113 | −0.0517 | 0.5552 |
| C41 | 0.6608 | 0.3487 | 0.7637 |
| C42 | 0.8842 | 0.3295 | 0.6081 |
| C43 | 0.7928 | 0.2013 | 0.8324 |
| C44 | 0.6478 | 0.3693 | 0.8244 |
| C45 | 0.9041 | 0.1825 | 0.5787 |
| C46 | 0.7116 | 0.2945 | 0.8580 |
| C47 | 0.7693 | 0.8565 | 0.9247 |
| C48 | 0.6523 | 0.6699 | 0.9393 |
| C49 | 0.6372 | 0.6130 | 0.8784 |
| C50 | 0.6886 | 0.6798 | 0.8418 |
| C51 | 0.8079 | 0.1861 | 0.7731 |
| C52 | 0.7539 | 0.8018 | 0.8657 |
| C53 | 0.7171 | 0.7906 | 0.9638 |
| C54 | 0.8594 | 1.0293 | 1.0095 |
| C55 | 0.5690 | 0.4784 | 0.8512 |
| C56 | 0.9344 | 1.1572 | 1.0187 |
| CL57 | 0.1318 | 0.2860 | 0.9213 |
| O58 | 0.2325 | 0.1474 | 0.6392 |
| O59 | 0.3774 | 0.4788 | 0.7078 |
| O60 | 0.3769 | 0.1826 | 0.5107 |
| O61 | 0.5074 | 0.3673 | 0.6076 |
| C62 | 0.2155 | 0.2845 | 0.7366 |
| C63 | 0.2440 | 0.2856 | 0.6735 |
| C64 | 0.2590 | 0.1866 | 0.7641 |
| C65 | 0.3642 | 0.3439 | 0.6737 |
| C66 | 0.1310 | 0.6369 | 0.8752 |
| C67 | 0.3659 | 0.1865 | 0.5718 |
| C68 | 0.2203 | −0.0149 | 0.5444 |
| C69 | 0.2495 | 0.6414 | 0.8737 |
| C70 | 0.2339 | 0.1891 | 0.8206 |
| C71 | 0.2440 | 0.1366 | 0.5760 |
| C72 | 0.2691 | 0.8826 | 0.9099 |
| C73 | 0.3878 | 0.3310 | 0.6097 |
| C74 | 0.0797 | 0.7646 | 0.8952 |
| C75 | 0.1225 | 0.3883 | 0.8232 |
| O76 | 0.0935 | −0.0372 | 0.5272 |
| C77 | 0.1466 | 0.3834 | 0.7646 |
| C78 | 0.1643 | 0.2886 | 0.8500 |
| C79 | 0.3160 | 0.7598 | 0.8907 |
| O80 | 0.3243 | 1.0074 | 0.9263 |
| C81 | 0.0564 | 0.5089 | 0.8537 |
| C82 | 0.1501 | 0.8831 | 0.9123 |
| C83 | 0.4517 | 1.0168 | 0.9429 |
| C84 | 0.4736 | 1.0085 | 1.0039 |
| CL85 | 0.2353 | 0.2852 | 0.0943 |
| O86 | 0.4643 | 0.4578 | 0.3847 |
| O87 | 0.6924 | 0.1640 | 0.4142 |
| C88 | 0.4307 | 0.3235 | 0.3510 |
| O89 | 0.6471 | 0.3804 | 0.5135 |
| C90 | 0.5401 | 0.2370 | 0.3503 |
| O91 | 0.4314 | 0.6909 | 0.4760 |
| C92 | 0.5025 | 0.4655 | 0.4471 |
| C93 | 0.3782 | 0.3234 | 0.2879 |
| O94 | 0.3688 | −0.3850 | 0.0770 |
| C95 | 0.2412 | 0.2163 | 0.2011 |
| O96 | 0.5177 | 0.1054 | 0.3143 |
| C97 | 0.5871 | 0.2380 | 0.4145 |
| C98 | 0.5309 | 0.6092 | 0.4771 |
| C99 | 0.6100 | 0.3805 | 0.4525 |
| C100 | 0.3806 | 0.3946 | 0.1963 |
| C101 | 0.2856 | 0.2342 | 0.2611 |
| C102 | 0.3122 | −0.2671 | 0.0968 |
| C103 | 0.1491 | 0.1041 | 0.1716 |
| C104 | 0.2436 | −0.2032 | 0.0581 |
| C105 | 0.2886 | 0.3016 | 0.1694 |
| C106 | 0.3259 | −0.2129 | 0.1566 |
| C107 | 0.4243 | 0.4052 | 0.2556 |
| C108 | 0.1916 | −0.0835 | 0.0830 |
| C109 | 0.3595 | −0.4411 | 0.0145 |
| C110 | 0.2039 | −0.0262 | 0.1455 |
| C111 | 0.2741 | −0.0939 | 0.1807 |
| C112 | 0.4263 | −0.5693 | 0.0039 |
| O113 | 0.6465 | 0.6039 | 0.6797 |
| O114 | 0.7349 | 0.7473 | 0.6386 |
| N115 | 0.4575 | 0.7439 | 0.6955 |
| C116 | 0.6529 | 0.7073 | 0.6592 |
| C117 | 0.5581 | 0.9376 | 0.6856 |
| C118 | 0.4708 | 0.8468 | 0.7558 |
| C119 | 0.5406 | 0.7887 | 0.6584 |
| C120 | 0.5558 | 0.9548 | 0.7523 |
| O121 | 0.1830 | 0.6331 | 0.6898 |
| O122 | 0.2453 | 0.7852 | 0.6450 |
| N123 | −0.0372 | 0.6985 | 0.6789 |
| C124 | 0.0468 | 0.7797 | 0.6565 |
| C125 | 0.0382 | 0.9228 | 0.6945 |
| C126 | 0.1683 | 0.7269 | 0.6638 |
| C127 | 0.0337 | 0.8955 | 0.7569 |
| C128 | −0.0365 | 0.7591 | 0.7436 |
| N129 | −0.3701 | −0.1217 | 0.3442 |
| C130 | −0.1562 | −0.1273 | 0.3652 |
| O131 | −0.1554 | −0.0439 | 0.3345 |
| O132 | −0.0663 | −0.1700 | 0.3912 |
| C133 | −0.2876 | −0.3360 | 0.3362 |
| C134 | −0.2710 | −0.1891 | 0.3727 |
| C135 | −0.3924 | −0.1926 | 0.2793 |
| C136 | −0.3216 | −0.3192 | 0.2720 |
| O137 | 0.4232 | −0.1933 | 0.3831 |
| O138 | 0.3366 | −0.0501 | 0.3332 |
| C139 | 0.2187 | −0.2024 | 0.3678 |
| N140 | 0.1226 | −0.1310 | 0.3394 |
| C141 | 0.3337 | −0.1410 | 0.3604 |
| C142 | 0.1992 | −0.3502 | 0.3341 |
| C143 | 0.1599 | −0.3386 | 0.2693 |
| C144 | 0.0885 | −0.2109 | 0.2771 |
| O145 | 0.2926 | 0.5997 | 0.5452 |
| O146 | 0.5342 | −0.0128 | 0.4878 |
| H150 | −0.0975 | 0.3899 | 0.4641 |
| H151 | 0.1418 | 0.4590 | 0.4337 |
| H152 | 0.0313 | 0.1936 | 0.4337 |
| H154 | 0.0862 | 0.3044 | 0.3298 |
| H155 | −0.1430 | 0.6195 | 0.4745 |
| H156 | −0.0310 | 0.5943 | 0.5295 |
| H157 | −0.1495 | 0.2477 | 0.3663 |
| H158 | −0.2539 | 0.1367 | 0.2824 |
| H159 | −0.1435 | 0.4768 | 0.1772 |
| H160 | −0.1255 | 0.0440 | 0.1660 |
| H161 | −0.4573 | −0.1862 | 0.1271 |
| H162 | −0.0551 | 0.4859 | 0.2809 |
| H163 | −0.0294 | −0.1642 | 0.1321 |
| H164 | −0.4249 | 0.0580 | 0.1988 |
| H165 | −0.4172 | 0.0974 | 0.1293 |
| H166 | −0.3545 | −0.3888 | 0.0944 |
| H167 | 0.0443 | −0.3425 | 0.1127 |

TABLE 18-continued

Table of Fractional Atomic Coordinates for Compound Ij 1:1 Complex with L-Proline Hemihydrate Form H.5-2 at T = −40° C.

| Atom | X | Y | Z |
|---|---|---|---|
| H168 | 0.0247 | −0.5195 | 0.0867 |
| H169 | 0.0584 | −0.4150 | 0.0027 |
| H170 | −0.0829 | −0.4910 | −0.0091 |
| H171 | −0.0634 | −0.3139 | 0.0169 |
| H176 | 0.6840 | 0.2850 | 0.6494 |
| H177 | 0.7179 | 0.1342 | 0.5591 |
| H178 | 0.9431 | 0.3006 | 0.6953 |
| H179 | 0.8770 | −0.0884 | 0.5846 |
| H180 | 0.8408 | −0.0648 | 0.5117 |
| H181 | 0.6098 | 0.4044 | 0.7359 |
| H182 | 0.8091 | 0.3693 | 0.5861 |
| H183 | 0.8427 | 0.1385 | 0.8583 |
| H184 | 0.9803 | 0.1446 | 0.6000 |
| H185 | 0.6091 | 0.6187 | 0.9683 |
| H186 | 0.6794 | 0.6399 | 0.7942 |
| H187 | 0.8728 | 0.1192 | 0.7530 |
| H188 | 0.7902 | 0.8541 | 0.8361 |
| H189 | 0.7271 | 0.8353 | 1.0122 |
| H190 | 0.7735 | 1.0569 | 1.0277 |
| H191 | 0.8986 | 0.9597 | 1.0334 |
| H192 | 0.5005 | 0.4927 | 0.8176 |
| H193 | 0.5288 | 0.4505 | 0.8873 |
| H194 | 0.9545 | 1.2094 | 1.0658 |
| H195 | 1.0166 | 1.1315 | 1.0008 |
| H196 | 0.8915 | 1.2288 | 0.9952 |
| H200 | 0.1797 | 0.3464 | 0.6531 |
| H201 | 0.3128 | 0.1093 | 0.7423 |
| H202 | 0.4283 | 0.2823 | 0.6914 |
| H203 | 0.4309 | 0.1186 | 0.5873 |
| H204 | 0.2676 | −0.0437 | 0.5075 |
| H205 | 0.2503 | −0.0734 | 0.5778 |
| H206 | 0.2938 | 0.5478 | 0.8573 |
| H207 | 0.2667 | 0.1115 | 0.8435 |
| H208 | 0.1813 | 0.2008 | 0.5579 |
| H209 | 0.3311 | 0.3978 | 0.5902 |
| H210 | −0.0167 | 0.7728 | 0.8951 |
| H212 | 0.1131 | 0.4619 | 0.7424 |
| H213 | 0.4107 | 0.7527 | 0.8914 |
| H214 | 0.0235 | 0.4869 | 0.8923 |
| H215 | −0.0164 | 0.5268 | 0.8227 |
| H216 | 0.1131 | 0.9807 | 0.9295 |
| H217 | 0.5000 | 0.9375 | 0.9142 |
| H218 | 0.4930 | 1.1146 | 0.9386 |
| H219 | 0.5658 | 1.0153 | 1.0225 |
| H220 | 0.4299 | 1.0899 | 1.0326 |
| H221 | 0.4370 | 0.9127 | 1.0082 |
| H223 | 0.3659 | 0.2811 | 0.3724 |
| H225 | 0.6059 | 0.2835 | 0.3311 |
| H227 | 0.4295 | 0.4306 | 0.4673 |
| H229 | 0.5247 | 0.1893 | 0.4346 |
| H230 | 0.5953 | 0.6489 | 0.4536 |
| H231 | 0.5686 | 0.6221 | 0.5232 |
| H232 | 0.6812 | 0.4246 | 0.4357 |
| H233 | 0.4161 | 0.4554 | 0.1692 |
| H234 | 0.2450 | 0.1769 | 0.2870 |
| H235 | 0.0958 | 0.0890 | 0.2045 |
| H236 | 0.0943 | 0.1338 | 0.1355 |
| H237 | 0.2331 | −0.2409 | 0.0101 |
| H238 | 0.3791 | −0.2651 | 0.1858 |
| H239 | 0.4960 | 0.4787 | 0.2767 |
| H240 | 0.1390 | −0.0325 | 0.0529 |
| H241 | 0.2692 | −0.4672 | −0.0046 |
| H242 | 0.3958 | −0.3734 | −0.0080 |
| H243 | 0.2899 | −0.0523 | 0.2290 |
| H244 | 0.4221 | −0.6177 | −0.0443 |
| H245 | 0.5184 | −0.5490 | 0.0216 |
| H246 | 0.3917 | −0.6427 | 0.0251 |
| H248 | 0.4793 | 0.6449 | 0.7024 |
| H249 | 0.6424 | 0.9714 | 0.6756 |
| H250 | 0.4899 | 0.9910 | 0.6668 |
| H251 | 0.3871 | 0.8958 | 0.7636 |
| H252 | 0.4974 | 0.8010 | 0.7924 |
| H253 | 0.4998 | 0.7712 | 0.6119 |
| H254 | 0.6437 | 0.9322 | 0.7755 |
| H255 | 0.5346 | 1.0526 | 0.7757 |
| H257 | −0.1244 | 0.7021 | 0.6547 |
| H258 | 0.0245 | 0.7713 | 0.6086 |
| H259 | 0.1125 | 0.9882 | 0.6931 |
| H260 | −0.0412 | 0.9702 | 0.6791 |
| H261 | 0.1221 | 0.8814 | 0.7786 |
| H262 | −0.0061 | 0.9737 | 0.7872 |
| H263 | −0.1266 | 0.7806 | 0.7533 |
| H264 | 0.0003 | 0.6937 | 0.7698 |
| H265 | −0.4482 | −0.1282 | 0.3648 |
| H267 | −0.2055 | −0.3921 | 0.3406 |
| H268 | −0.3541 | −0.3919 | 0.3515 |
| H269 | −0.2776 | −0.1726 | 0.4197 |
| H270 | −0.4835 | −0.2219 | 0.2664 |
| H271 | −0.3651 | −0.1301 | 0.2520 |
| H272 | −0.2450 | −0.3036 | 0.2505 |
| H273 | −0.3737 | −0.4037 | 0.2429 |
| H275 | 0.2126 | −0.1876 | 0.4150 |
| H276 | 0.0471 | −0.1254 | 0.3631 |
| H277 | 0.2819 | −0.4071 | 0.3370 |
| H278 | 0.1354 | −0.4038 | 0.3515 |
| H279 | 0.2344 | −0.3225 | 0.2459 |
| H280 | 0.1069 | −0.4219 | 0.2420 |
| H281 | −0.0019 | −0.2405 | 0.2681 |
| H282 | 0.1098 | −0.1545 | 0.2449 |
| H4O | −0.0494 | 0.0591 | 0.3246 |
| H5O | 0.2411 | 0.2106 | 0.4570 |
| H3O | 0.1948 | 0.4772 | 0.5288 |
| H9O | −0.0304 | 0.7367 | 0.4370 |
| H91O | 0.4288 | 0.7378 | 0.4387 |
| H89O | 0.5701 | 0.3737 | 0.5359 |
| H87O | 0.7447 | 0.1972 | 0.4579 |
| H96O | 0.4441 | 0.0598 | 0.3281 |
| H32O | 0.7685 | 0.5088 | 0.6888 |
| H30 | 1.0223 | 0.3832 | 0.5666 |
| H34 | 0.9788 | 0.0971 | 0.5019 |
| H35O | 0.7109 | −0.1813 | 0.5836 |
| H60O | 0.4380 | 0.1072 | 0.4941 |
| H61 | 0.5322 | 0.4602 | 0.6402 |
| H59O | 0.2991 | 0.5325 | 0.6984 |
| H76 | 0.0757 | −0.1438 | 0.5063 |
| H29N | −0.3483 | −0.0232 | 0.3484 |
| H40N | 0.1520 | −0.0373 | 0.3393 |
| H15N | 0.3746 | 0.7405 | 0.6748 |
| H23N | −0.0113 | 0.6018 | 0.6728 |
| H946 | 0.4919 | −0.0828 | 0.4471 |
| H1W | 0.2742 | 0.6734 | 0.5848 |
| H846 | 0.6016 | −0.0665 | 0.5089 |
| H2W | 0.3486 | 0.6479 | 0.5212 |

Utilities and Combinations

A. Utilities

The compound of the present invention possesses activity as an inhibitor of the sodium dependent glucose transporters found in the intestine and kidney of mammals. Preferably, the compound of the invention is a selective inhibitor of renal SGLT2 activity, and therefore may be used in the treatment of diseases or disorders associated with SGLT2 activity.

Accordingly, the compound of the present invention can be administered to mammals, preferably humans, for the treatment of a variety of conditions and disorders, including, but not limited to, treating or delaying the progression or onset of diabetes (including Type I and Type II, impaired glucose tolerance, insulin resistance, and diabetic complications, such as nephropathy, retinopathy, neuropathy and cataracts), hyperglycemia, hyperinsulinemia, hypercholesterolemia, dyslipidemia, elevated blood levels of free fatty acids or glycerol, hyperlipidemia, hypertriglyceridemia, obesity, wound healing, tissue ischemia, atherosclerosis and hypertension. The compound of the present invention may also be utilized to increase the blood levels of high density lipoprotein (HDL).

In addition, the conditions, diseases, and maladies collectively referenced to as "Syndrome X" or Metabolic Syndrome as detailed in Johannsson, *J. Clin. Endocrinol. Metab.*, 82, 727-34 (1997), may be treated employing the compound of the present invention.

The crystalline compounds (S)-PG (SC-3) (Ia), (R)-PG (SD-3) (Ib), SA-1 (Ic), SB-1 (Id), SB-2 (Ie) 1:2 L-proline complex form 3 (Ih), 1:1 L-proline complex form 6 (Ii) 1:1 L-proline hemihydrate complex form H.5-2 (Ij) and 1:1.3 L-phenylalanine complex form 2 (Ik) may be administered in dosage forms and in dosages as disclosed in U.S. Pat. No. 6,515,117 the disclosure of which in its entirety is incorporated herein by reference.

B. Combinations

The present invention includes within its scope pharmaceutical compositions comprising, as an active ingredient, a therapeutically effective amount of a compound of formula I, including (S)-PG (form SC-3, Ia), (R)-PG (form SD-3, Ib), SA-1 (Ic), SB-1 (Id), SB-2 (Ie), 1:2 L-proline complex form 3 (Ih), 1:1 L-proline complex form 6 (Ii), 1:1 L-proline hemihydrate complex form H.5-2 (Ij), and 1:1.3 L-phenylalanine complex form 2 (Ik), alone or in combination with a pharmaceutical carrier or diluent. Optionally, the compound of the present invention can be utilized as an individual treatment, or utilized in combination with one or more other therapeutic agent(s).

Other "therapeutic agent(s)" suitable for combination with the compound of the present invention include, but are not limited to, known therapeutic agents useful in the treatment of the aforementioned disorders including: anti-diabetic agents; anti-hyperglycemic agents; hypolipidemic/lipid lowering agents; anti-obesity agents; anti-hypertensive agents and appetite suppressants.

Examples of suitable anti-diabetic agents for use in combination with the compound of the present invention include biguanides (e.g., metformin or phenformin), glucosidase inhibitors (e.g., acarbose or miglitol), insulins (including insulin secretagogues or insulin sensitizers), meglitinides (e.g., repaglinide), sulfonylureas (e.g., glimepiride, glyburide, gliclazide, chlorpropamide and glipizide), biguanide/glyburide combinations (e.g., Glucovance®), thiazolidinediones (e.g., troglitazone, rosiglitazone and pioglitazone), PPAR-alpha agonists, PPAR-gamma agonists, PPAR alpha/gamma dual agonists, glycogen phosphorylase inhibitors, inhibitors of fatty acid binding protein (aP2), glucagon-like peptide-1 (GLP-1) or other agonists of the GLP-1 receptor, and dipeptidyl peptidase IV (DPP4) inhibitors.

It is believed that the use of the compound of formula I in combination with at least one or more other antidiabetic agent(s) provides antihyperglycemic results greater than that possible from each of these medicaments alone and greater than the combined additive anti-hyperglycemic effects produced by these medicaments.

Other suitable thiazolidinediones include Mitsubishi's MCC-555 (disclosed in U.S. Pat. No. 5,594,016), Glaxo-Wellcome's faraglitazar (GI-262570), englitazone (CP-68722, Pfizer) or darglitazone (CP-86325, Pfizer, isaglitazone (MIT/J&J), reglitazar (JTT-501) (JPNT/P&U), rivoglitazone (R-119702) (Sankyo/WL), liraglutide (NN-2344) (Dr. Reddy/NN), or (Z)-1,4-bis-4-[(3,5-dioxo-1,2,4-oxadiazolidin-2-yl-methyl)]phenoxybut-2-ene (YM-440, Yamanouchi).

Examples of PPAR-alpha agonists, PPAR-gamma agonists and PPAR alpha/gamma dual agonists include muraglitazar, peliglitazar, tesaglitazar AR-H039242 Astra/Zeneca, GW-501516 (Glaxo-Wellcome), KRP297 (Kyorin Merck) as well as those disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes, 47, 1841-1847 (1998), WO 01/21602 and in U.S. Pat. No. 6,653,314, the disclosure of which is incorporated herein by reference, employing dosages as set out therein, which compounds designated as preferred are preferred for use herein.

Suitable aP2 inhibitors include those disclosed in U.S. application Ser. No. 09/391,053, filed Sep. 7, 1999, and in U.S. application Ser. No. 09/519,079, filed Mar. 6, 2000, employing dosages as set out herein.

Suitable DPP4 inhibitors include those disclosed in WO 99/38501, WO 99/46272, WO 99/67279 (PROBIODRUG), WO 99/67278 (PROBIODRUG), WO 99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) as disclosed by Hughes et al., Biochemistry, 38(36), 11597-11603, 1999, TSL-225 (tryptophyl-1,2,3,4-tetrahydroisoquinoline-3-carboxylic acid (disclosed by Yamada et al., Bioorg. & Med. Chem. Lett. 8 (1998) 1537-1540), 2-cyanopyrrolidides and 4-cyanopyrrolidides, as disclosed by Ashworth et al., Bioorg. & Med. Chem. Lett., Vol. 6, No. 22, pp. 1163-1166 and 2745-2748 (1996), the compounds disclosed in U.S. application Ser. No. 10/899,641, WO 01/68603 and U.S. Pat. No. 6,395,767, employing dosages as set out in the above references.

Other suitable meglitinides include nateglinide (Novartis) or KAD1229 (PF/Kissei).

Examples of suitable anti-hyperglycemic agents for use in combination with the compound of the present invention include glucagon-like peptide-1 (GLP-1) such as GLP-1(1-36) amide, GLP-1(7-36) amide, GLP-1(7-37) (as disclosed in U.S. Pat. No. 5,614,492), as well as exenatide (Amylin/Lilly), LY-315902 (Lilly), MK-0431 (Merck), liraglutide (NovoNordisk), ZP-10 (Zealand Pharmaceuticals A/S), CJC-1131 (Conjuchem Inc), and the compounds disclosed in WO 03/033671.

Examples of suitable hypolipidemic/lipid lowering agents for use in combination with the compound of the present invention include one or more MTP inhibitors, HMG CoA reductase inhibitors, squalene synthetase inhibitors, fabric acid derivatives, ACAT inhibitors, lipoxygenase inhibitors, cholesterol absorption inhibitors, ileal $Na^+$/bile acid co-transporter inhibitors, up-regulators of LDL receptor activity, bile acid sequestrants, cholesterol ester transfer protein (e.g., CETP inhibitors, such as torcetrapib (CP-529414, Pfizer) and JTT-705 (Akros Pharma)), PPAR agonists (as described above) and/or nicotinic acid and derivatives thereof.

MTP inhibitors which may be employed as described above include those disclosed in U.S. Pat. Nos. 5,595,872, 5,739,135, 5,712,279, 5,760,246, 5,827,875, 5,885,983 and 5,962,440.

The HMG CoA reductase inhibitors which may be employed in combination with one or more compound of formula I include mevastatin and related compounds, as disclosed in U.S. Pat. No. 3,983,140, lovastatin (mevinolin) and related compounds, as disclosed in U.S. Pat. No. 4,231,938, pravastatin and related compounds, such as disclosed in U.S. Pat. No. 4,346,227, simvastatin and related compounds, as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin, as disclosed in U.S. Pat. Nos. 5,006,530 and 5,177,080, atorvastatin, as disclosed in U.S. Pat. Nos. 4,681,893, 5,273,995, 5,385,929 and 5,686,104, atavastatin (Nissan/Sankyo's nisvastatin (NK-104)), as disclosed in U.S. Pat. No. 5,011,930, visastatin (Shionogi-Astra/Zeneca (ZD-4522)), as disclosed in U.S. Pat. No. 5,260,440, and related statin compounds disclosed in U.S. Pat. No. 5,753,675, pyrazole analogs of mevalonolactone derivatives, as disclosed in U.S. Pat. No. 4,613,610, indene analogs of mevalonolactone derivatives, as disclosed in PCT application WO 86/03488, 6-[2-(substituted-pyrrol-1-yl)-alkyl)pyran-2-ones and derivatives thereof, as disclosed in U.S. Pat. No. 4,647,576, Searle's SC-45355 (a 3-substituted pentanedioic acid derivative) dichloroacetate, imidazole analogs of mevalonolactone, as disclosed in PCT application WO 86/07054, 3-carboxy-2-hydroxy-propane-phosphonic acid derivatives, as disclosed in French Patent No. 2,596,393, 2,3-disubstituted pyrrole, furan and thiophene derivatives, as disclosed in European Patent Application No. 0221025, naphthyl analogs of mevalonolactone, as disclosed in U.S. Pat. No. 4,686,237, octahydronaphthalenes, such as disclosed in U.S. Pat. No. 4,499,289, keto analogs of mevinolin (lovastatin), as disclosed in European Patent Application No. 0142146 A2, and quinoline and pyridine derivatives, as disclosed in U.S. Pat. Nos. 5,506,219 and 5,691,322.

Preferred hypolipidemic agents are pravastatin, lovastatin, simvastatin, atorvastatin, fluvastatin, cerivastatin, atavastatin and ZD-4522.

In addition, phosphinic acid compounds useful in inhibiting HMG CoA reductase, such as those disclosed in GB 2205837, are suitable for use in combination with the compound of the present invention.

The squalene synthetase inhibitors suitable for use herein include, but are not limited to, α-phosphono-sulfonates disclosed in U.S. Pat. No. 5,712,396, those disclosed by Biller et al., J. Med. Chem., 1988, Vol. 31, No. 10, pp. 1869-1871, including isoprenoid (phosphinyl-methyl)phosphonates, as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C.D., Current Pharmaceutical Design, 2, 1-40 (1996).

In addition, other squalene synthetase inhibitors suitable for use herein include the terpenoid pyrophosphates disclosed by P. Ortiz de Montellano et al, J. Med. Chem., 1977, 20, 243-249, the farnesyl diphosphate analog A and presqualene pyrophosphate (PSQ-PP) analogs as disclosed by Corey and Volante, J. Am. Chem. Soc., 1976, 98, 1291-1293, phosphinylphosphonates reported by McClard, R. W. et al., J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40-43, 48-51, Summary.

The fabric acid derivatives which may be employed in combination the compound of formula I include fenofibrate, gemfibrozil, clofibrate, bezafibrate, ciprofibrate, clinofibrate and the like, probucol, and related compounds, as disclosed in U.S. Pat. No. 3,674,836, probucol and gemfibrozil being preferred, bile acid sequestrants, such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277, 082 and CL-283,546 (disubstituted urea derivatives), nicotinic acid, acipimox, acifran, neomycin, p-aminosalicylic acid, aspirin, poly(diallylmethylamine) derivatives, such as disclosed in U.S. Pat. No. 4,759,923, quaternary amine poly(diallyldimethylammonium chloride) and ionenes, such as disclosed in U.S. Pat. No. 4,027,009, and other known serum cholesterol lowering agents.

The ACAT inhibitor which may be employed in combination the compound of formula I include those disclosed in Drugs of the Future 24, 9-15 (1999), (Avasimibe); "The ACAT inhibitor, C1-1011 is effective in the prevention and regression of aortic fatty streak area in hamsters", Nicolosi et al., Atherosclerosis (Shannon, Irel). (1998), 137(1), 77-85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16-30; "RP 73163: a bioavailable alkylsulfinyl-diphenylimidazole ACAT inhibitor", Smith, C., et al, Bioorg. Med. Chem. Lett. (1996), 6(1), 47-50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al., Curr. Med. Chem. (1994), 1(3), 204-25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al., Chemtracts: Org. Chem. (1995), 8(6), 359-62, or TS-962 (Taisho Pharmaceutical Co. Ltd).

The hypolipidemic agent may be an up-regulator of LD2 receptor activity, such as 1(3H)-isobenzofuranone,3-(13-hydroxy-10-oxotetradecyl)-5,7-dimethoxy-(MD-700, Taisho Pharmaceutical Co. Ltd) and cholestan-3-ol-,4-(2-propenyl)-(3a,4a,5a)-(LY295427, Eli Lilly).

Examples of suitable cholesterol absorption inhibitor for use in combination with the compound of the invention include SCH48461 (Schering-Plough), as well as those disclosed in Atherosclerosis 115, 45-63 (1995) and J. Med. Chem. 41, 973 (1998).

Examples of suitable ileal $Na^+$/bile acid co-transporter inhibitors for use in combination with the compound of the invention include compounds as disclosed in Drugs of the Future, 24, 425-430 (1999).

The lipoxygenase inhibitors which may be employed in combination the compound of formula I include 15-lipoxygenase (15-LO) inhibitors, such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199-1206, and Cornicelli et al, "15-Lipoxygenase and its Inhibition: A Novel Therapeutic Target for Vascular Disease", Current Pharmaceutical Design, 1999, 5, 11-20.

Examples of suitable anti-hypertensive agents for use in combination with the compound of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-obesity agents for use in combination with the compound of the present invention include a beta 3 adrenergic agonist, a lipase inhibitor, a serotonin (and dopamine) reuptake inhibitor, a thyroid receptor beta drug, 5HT2C agonists, (such as Arena APD-356); MCHR1 antagonists such as Synaptic SNAP-7941 and Takeda T-226926, melanocortin receptor (MC4R) agonists, melanin-concentrating hormone receptor (MCHR) antagonists (such as Synaptic SNAP-7941 and Takeda T-226926), galanin receptor modulators, orexin antagonists, CCK agonists, NPY1 or NPYS antagonist, NPY2 and NPY4 modulators, corticotropin releasing factor agonists, histamine receptor-3 (H3) modulators, 11-beta-HSD-1 inhibitors, adinopectin receptor modulators, monoamine reuptake inhibitors or releasing agents, a ciliary neurotrophic factor (CNTF, such as AXOKINE® by Regeneron), BDNF (brain-derived neurotrophic factor), leptin and leptin receptor modulators, cannabinoid-1 receptor antagonists (such as SR-141716 (Sanofi) or SLV-319 (Solvay)), and/or an anorectic agent.

The beta 3 adrenergic agonists which may be optionally employed in combination with compound of the present invention include AJ9677 (Takeda/Dainippon), L750355 (Merck), or CP331648 (Pfizer,) or other known beta 3 agonists, as disclosed in U.S. Pat. Nos. 5,541,204, 5,770, 615, 5,491,134, 5,776,983 and 5,488,064.

Examples of lipase inhibitors which may be optionally employed in combination with compound of the present invention include orlistat or ATL-962 (Alizyme).

The serotonin (and dopamine) reuptake inhibitor (or serotonin receptor agonists) which may be optionally employed in combination with a compound of the present invention may be BVT-933 (Biovitrum), sibutramine, topiramate (Johnson & Johnson) or axokine (Regeneron).

Examples of thyroid receptor beta compounds which may be optionally employed in combination with the compound of the present invention include thyroid receptor ligands, such as those disclosed in WO 97/21993 (U. Cal SF), WO 99/00353 (KaroBio) and WO 00/039077 (KaroBio).

The monoamine reuptake inhibitors which may be optionally employed in combination with compound of the present invention include fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol.

The anorectic agent which may be optionally employed in combination with the compound of the present invention include topiramate (Johnson & Johnson), dexamphetamine, phentermine, phenylpropanolamine or mazindol.

The aforementioned patents and patent applications are incorporated herein by reference.

The above other therapeutic agents, when employed in combination with the compound of the present invention may be used, for example, in those amounts indicated in the Physicians' Desk Reference, as in the patents set out above or as otherwise determined by one of ordinary skill in the art.

What is claimed is:
1. A crystalline structure of a compound of formula I

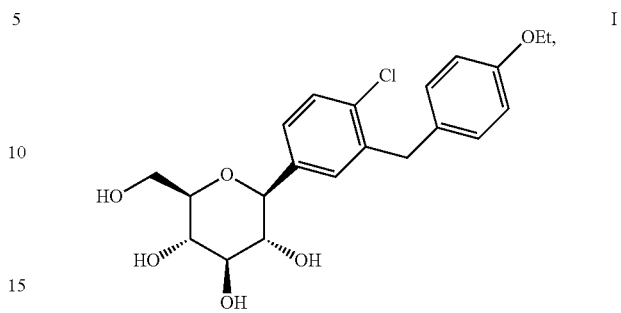

which is (R)-PG (form SD-3).

2. The crystalline structure according to claim 1, in substantially pure form.

3. The crystalline structure (R)-PG (form SD-3) according to claim 1 having the formula 1b

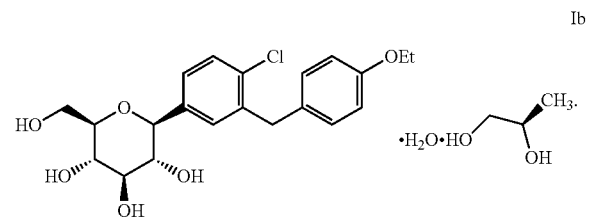

4. The crystalline structure according to claim 3 characterized by one or more of the following:
   a) a powder x-ray diffraction pattern comprising 2θ values (CuKα λ=1.5418 Å) of 3.9±0.1, 8.0±0.1, 8.7±0.1, 15.3±0.1, 15.6±0.1, 17.2±0.1, 19.2±0.1, 19.9±0.1 and 20.3±0.1, at room temperature;
   b) a solid state $^{13}$C NMR spectrum having substantially similar peak positions at 15.8, 17.6, 39.0, 60.9, 63.2, 67.4, 69.7, 77.3, 79.2, 79.8, 113.3, 123.6, 129.0, 130.4, 132.0, 135.6, 139.2 and 157.9 ppm, as determined on a 400 MHz spectrometer relative to TMS at zero;
   c) a differential scanning calorimetry thermogram having an endotherm in the range of about 43° C. to 60° C. or as shown in FIG. 8; or
   d) thermal gravimetric analysis curve with about 18.7% weight loss from about room temperature up to about 235° C. or as shown in FIG. 6.

5. A pharmaceutical composition comprising an effective amount of a crystal structure of a compound of formula I according to claim 1 and a pharmaceutically acceptable carrier or diluent.

6. The pharmaceutical composition according to claim 5 wherein the crystalline structure is in substantially pure form.

7. A pharmaceutical composition comprising an effective amount of the crystal structure according to claim 1 in combination with one or more therapeutic agents selected from the group consisting of an antidiabetic agent, a antihypertensive agent, an anti-atherosclerotic agent and a lipid-lowering agent.

* * * * *